US007604965B2

(12) United States Patent
McBride et al.

(10) Patent No.: US 7,604,965 B2
(45) Date of Patent: *Oct. 20, 2009

(54) THERMAL REACTION DEVICE AND METHOD FOR USING THE SAME

(75) Inventors: Lincoln McBride, Belmont, CA (US); Geoffrey Facer, San Francisco, CA (US); Marc Unger, San Mateo, CA (US); Michael Lucero, South San Francisco, CA (US); Hany Ramez Nassef, San Mateo, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/084,357

(22) Filed: Mar. 18, 2005

(65) Prior Publication Data

US 2005/0252773 A1 Nov. 17, 2005

Related U.S. Application Data

(63) Continuation-in-part of application No. 10/876,046, filed on Jun. 23, 2004, and a continuation-in-part of application No. 10/837,885, filed on May 2, 2004, which is a continuation-in-part of application No. 10/818,642, filed on Apr. 5, 2004.

(60) Provisional application No. 60/460,634, filed on Apr. 3, 2003.

(51) Int. Cl.
*C12Q 1/68* (2006.01)
*C12P 19/34* (2006.01)

(52) U.S. Cl. .......................... 435/91.2; 435/6; 435/91.1

(58) Field of Classification Search ........................ None
See application file for complete search history.

(56) References Cited

U.S. PATENT DOCUMENTS

| | | | |
|---|---|---|---|
| 2,656,508 A | 10/1953 | Coulter | |
| 3,560,754 A | 2/1971 | Kamentsky | |
| 3,570,515 A | 3/1971 | Kinner | |
| 3,747,628 A | 7/1973 | Holster et al. | |
| 3,839,176 A | 10/1974 | McCoy et al. | |
| 3,984,307 A | 10/1976 | Kamentsky et al. | |
| 4,046,159 A | 9/1977 | Pegourie | |
| 4,119,368 A | 10/1978 | Yamazaki | |
| 4,153,855 A | 5/1979 | Feingold | |
| 4,245,673 A | 1/1981 | Bouteille et al. | |
| 4,373,527 A | 2/1983 | Fischell | |
| 4,399,219 A | 8/1983 | Weaver | |
| 4,434,704 A | 3/1984 | Surjaatmadja | |
| 4,575,681 A | 3/1986 | Grosso et al. | |
| 4,581,624 A | 4/1986 | O'Connor | |
| 4,585,209 A | 4/1986 | Aine et al. | |
| 4,662,710 A | 5/1987 | ten Berge | |
| 4,675,300 A | 6/1987 | Zare et al. | |
| 4,786,165 A | 11/1988 | Yamamoto et al. | |
| 4,797,842 A | 1/1989 | Nackman et al. | |
| 4,876,504 A | 10/1989 | Blake et al. | |
| 4,898,582 A | 2/1990 | Faste | |
| 4,908,112 A | 3/1990 | Pace | |
| 4,936,465 A | 6/1990 | Zold | |
| 4,963,498 A | 10/1990 | Hillman et al. | |
| 4,992,312 A | 2/1991 | Frisch | |
| 5,032,381 A | 7/1991 | Bronstein et al. | |
| 5,085,562 A | 2/1992 | van Lintel | |
| 5,088,515 A | 2/1992 | Kamen | |
| 5,096,388 A | 3/1992 | Weinberg | |
| 5,100,627 A | 3/1992 | Buican et al. | |
| 5,126,022 A | 6/1992 | Soane et al. | |
| 5,126,115 A | 6/1992 | Fujita et al. | |
| 5,132,012 A | 7/1992 | Miura et al. | |
| 5,140,161 A | 8/1992 | Hillman et al. | |
| 5,164,558 A | 11/1992 | Huff et al. | |
| 5,164,598 A | 11/1992 | Hillman et al. | |
| 5,171,132 A | 12/1992 | Miyazaki et al. | |
| 5,224,843 A | 7/1993 | van Lintel | |
| 5,259,737 A | 11/1993 | Kamisuki et al. | |
| 5,265,327 A | 11/1993 | Faris et al. | |
| 5,271,724 A | 12/1993 | van Lintel | |
| 5,290,240 A | 3/1994 | Horres, Jr. | |
| 5,307,186 A | 4/1994 | Izumi et al. | |
| 5,336,062 A | 8/1994 | Richter | |
| 5,346,372 A | 9/1994 | Naruse et al. | |
| 5,375,979 A | 12/1994 | Trah | |
| 5,376,252 A | 12/1994 | Ekstrom | |
| 5,400,741 A | 3/1995 | DeTitta et al. | |
| 5,423,287 A | 6/1995 | Usami et al. | |
| 5,434,047 A | 7/1995 | Arnold et al. | |
| 5,434,049 A | 7/1995 | Okuno et al. | |
| 5,452,878 A | 9/1995 | Gravesen et al. | |
| 5,486,335 A | 1/1996 | Wilding et al. | |
| 5,487,003 A | 1/1996 | Iwasawa et al. | |
| 5,496,009 A | 3/1996 | Farrell et al. | |
| 5,498,392 A | 3/1996 | Wilding et al. | |

(Continued)

FOREIGN PATENT DOCUMENTS

EP 0 592 094 A2 4/1994

(Continued)

OTHER PUBLICATIONS

Vogelstein et al., "Digital PCR," PNAS, USA, Aug. 1999, vol. 96, pp. 9236-9241.*

(Continued)

*Primary Examiner*—Young J Kim
(74) *Attorney, Agent, or Firm*—Townsend and Townsend and Crew LLP

(57) ABSTRACT

An M×N matrix microfluidic device for performing a matrix of reactions, the device having a plurality of reaction cells in communication with one of either a sample inlet or a reagent inlet through a via formed within an elastomeric block of the device. Methods provided include a method for forming vias in parallel in an elastomeric layer of an elastomeric block of a microfluidic device, the method comprising using patterned photoresist masks and etching reagents to etch away regions or portions of an elastomeric layer of the elastomeric block.

21 Claims, 28 Drawing Sheets

U.S. PATENT DOCUMENTS

| | | | |
|---|---|---|---|
| 5,500,071 A | 3/1996 | Kalltenbach et al. |
| 5,512,131 A | 4/1996 | Kumar et al. |
| 5,525,464 A | 6/1996 | Drmanac et al. |
| 5,529,465 A | 6/1996 | Zengerle et al. |
| 5,558,998 A | 9/1996 | Hammond et al. |
| 5,571,410 A | 11/1996 | Swedberg et al. |
| 5,574,893 A | 11/1996 | Southgate et al. |
| 5,580,523 A | 12/1996 | Bard |
| 5,587,128 A | 12/1996 | Wilding et al. |
| 5,589,136 A | 12/1996 | Northrup et al. |
| 5,593,130 A | 1/1997 | Hansson et al. |
| 5,595,650 A | 1/1997 | Manz |
| 5,608,519 A | 3/1997 | Gourley |
| 5,632,876 A | 5/1997 | Zanzucchi et al. |
| 5,641,400 A | 6/1997 | Kaltenbach et al. |
| 5,642,015 A | 6/1997 | Whitehead et al. |
| 5,656,155 A | 8/1997 | Norcross et al. |
| 5,659,171 A | 8/1997 | Young et al. |
| 5,660,370 A | 8/1997 | Webster |
| 5,661,222 A | 8/1997 | Hare |
| 5,681,024 A | 10/1997 | Lisec et al. |
| 5,702,618 A | 12/1997 | Saaski et al. |
| 5,705,018 A | 1/1998 | Hartley |
| 5,716,852 A | 2/1998 | Yager et al. |
| 5,726,751 A | 3/1998 | Altendorf et al. |
| 5,750,015 A | 5/1998 | Soane et al. |
| 5,757,482 A | 5/1998 | Fuchs et al. |
| 5,759,014 A | 6/1998 | Van Lintel |
| 5,775,371 A | 7/1998 | Pan et al. |
| 5,779,868 A | 7/1998 | Parce et al. |
| 5,788,468 A | 8/1998 | Dewa et al. |
| 5,800,690 A | 9/1998 | Chow et al. |
| 5,807,522 A | 9/1998 | Brown et al. |
| 5,833,926 A | 11/1998 | Wurzel et al. |
| 5,836,750 A | 11/1998 | Cabuz |
| 5,837,200 A | 11/1998 | Diessel et al. |
| 5,842,787 A | 12/1998 | Kopf-Sill et al. |
| 5,852,495 A | 12/1998 | Parce |
| 5,854,684 A | 12/1998 | Stabile et al. |
| 5,856,174 A | 1/1999 | Lipshutz et al. |
| 5,858,187 A | 1/1999 | Ramsey et al. |
| 5,858,649 A | 1/1999 | Asgari et al. |
| 5,863,502 A | 1/1999 | Southgate et al. |
| 5,863,801 A | 1/1999 | Southgate et al. |
| 5,869,004 A | 2/1999 | Parce et al. |
| 5,875,817 A | 3/1999 | Carter |
| 5,876,187 A | 3/1999 | Afromowitz |
| 5,880,071 A | 3/1999 | Parce et al. |
| 5,904,824 A | 5/1999 | Oh |
| 5,932,799 A | 8/1999 | Moles |
| 5,942,443 A | 8/1999 | Parce et al. |
| 5,971,355 A | 10/1999 | Biegelsen et al. |
| 5,994,696 A | 11/1999 | Tai et al. |
| 5,997,961 A | 12/1999 | Feng et al. |
| 6,004,442 A | 12/1999 | Choulga et al. |
| 6,007,309 A | 12/1999 | Hartley |
| 6,042,709 A | 3/2000 | Parce et al. |
| 6,043,080 A | 3/2000 | Lipshutz et al. |
| 6,056,428 A | 5/2000 | Devoino et al. |
| 6,089,534 A | 7/2000 | Biegelsen et al. |
| 6,117,634 A | 9/2000 | Langmore et al. |
| 6,123,769 A | 9/2000 | Sanjoh |
| 6,126,899 A | 10/2000 | Woudenberg et al. |
| 6,132,685 A | 10/2000 | Kercso et al. |
| 6,143,496 A | 11/2000 | Brown et al. |
| 6,149,787 A | 11/2000 | Chow et al. |
| 6,149,870 A | 11/2000 | Parce et al. |
| 6,155,282 A | 12/2000 | Zachary et al. |
| 6,167,910 B1 | 1/2001 | Chow |
| 6,174,365 B1 | 1/2001 | Sanjoh |
| 6,182,020 B1 | 1/2001 | Fairbanks |
| 6,221,654 B1 | 4/2001 | Quake et al. |
| 6,235,175 B1 | 5/2001 | Dubrow et al. |
| 6,246,330 B1 | 6/2001 | Nielsen |
| 6,274,337 B1 | 8/2001 | Parce et al. |
| 6,296,673 B1 | 10/2001 | Santarsiero et al. |
| 6,321,791 B1 | 11/2001 | Chow |
| 6,329,209 B1 | 12/2001 | Wagner et al. |
| 6,345,502 B1 | 2/2002 | Tai et al. |
| 6,375,871 B1 | 4/2002 | Bentsen et al. |
| 6,408,878 B2 | 6/2002 | Unger et al. |
| 6,409,832 B2 | 6/2002 | Weigl et al. |
| 6,488,832 B2 | 12/2002 | Heller |
| 6,488,872 B1 | 12/2002 | Beebe et al. |
| 6,500,323 B1 | 12/2002 | Chow et al. |
| 6,508,988 B1 | 1/2003 | Van Dam et al. |
| 6,533,914 B1 | 3/2003 | Liu |
| 6,537,799 B2 | 3/2003 | Chow et al. |
| 6,540,895 B1 | 4/2003 | Quake et al. |
| 6,541,071 B1 | 4/2003 | Bookbinder et al. |
| 6,563,111 B1 | 5/2003 | Moon et al. |
| 6,569,382 B1 | 5/2003 | Edman et al. |
| 6,581,441 B1 | 6/2003 | Paul |
| 6,585,939 B1 | 7/2003 | Dapprich |
| 6,596,545 B1 | 7/2003 | Wagner et al. |
| 6,605,472 B1 | 8/2003 | Skinner et al. |
| 6,627,076 B2 | 9/2003 | Griffiths |
| 6,662,818 B2 | 12/2003 | Paul et al. |
| 6,664,104 B2 | 12/2003 | Pourahmadi et al. |
| 6,677,131 B2 | 1/2004 | Yuen |
| 6,689,473 B2 | 2/2004 | Guire et al. |
| 6,713,327 B2 | 3/2004 | Leedy |
| 6,716,378 B2 | 4/2004 | Yang et al. |
| 6,736,978 B1 | 5/2004 | Porter et al. |
| 6,749,814 B1 | 6/2004 | Bergh et al. |
| 6,752,922 B2 | 6/2004 | Huang et al. |
| 6,765,279 B2 | 7/2004 | Leedy |
| 6,767,706 B2 | 7/2004 | Quake et al. |
| 6,829,753 B2 | 12/2004 | Lee et al. |
| 6,833,242 B2 | 12/2004 | Quake et al. |
| 6,847,153 B1 | 1/2005 | Balizer |
| 6,866,785 B2 | 3/2005 | Zare et al. |
| 6,884,346 B2 | 4/2005 | Zare et al. |
| 6,885,982 B2 | 4/2005 | Harris et al. |
| 6,929,030 B2 | 8/2005 | Unger et al. |
| 6,960,437 B2 | 11/2005 | Enzelberger et al. |
| 6,977,145 B2 | 12/2005 | Fouillet et al. |
| 7,118,910 B2 | 10/2006 | Unger et al. |
| 2001/0027745 A1 | 10/2001 | Weigl et al. |
| 2001/0041357 A1 | 11/2001 | Fouillet et al. |
| 2002/0037499 A1 | 3/2002 | Quake et al. |
| 2002/0058332 A1 | 5/2002 | Quake et al. |
| 2002/0064885 A1 | 5/2002 | Bedingham et al. |
| 2002/0108097 A1 | 8/2002 | Harris et al. |
| 2002/0109114 A1 | 8/2002 | Driggs et al. |
| 2002/0127736 A1 | 9/2002 | Fu et al. |
| 2002/0148992 A1 | 10/2002 | Hayenga et al. |
| 2002/0158022 A1 | 10/2002 | Huang et al. |
| 2002/0164816 A1 | 11/2002 | Quake |
| 2002/0183996 A1 | 12/2002 | Lee et al. |
| 2002/0197603 A1 | 12/2002 | Chow et al. |
| 2003/0008308 A1 | 1/2003 | Enzelberger et al. |
| 2003/0049659 A1 | 3/2003 | Lapidus et al. |
| 2003/0134129 A1 | 7/2003 | Lammertink et al. |
| 2003/0138829 A1 | 7/2003 | Unger et al. |
| 2003/0143120 A1 | 7/2003 | Ruediger et al. |
| 2003/0175947 A1 | 9/2003 | Liu et al. |
| 2004/0072278 A1 | 4/2004 | Chou et al. |
| 2004/0096960 A1 | 5/2004 | Burd Mehta et al. |
| 2004/0115838 A1 | 6/2004 | Quake et al. |
| 2004/0141887 A1 | 7/2004 | Mainquist et al. |
| 2004/0209354 A1 | 10/2004 | Mathies et al. |
| 2004/0248167 A1 | 12/2004 | Quake et al. |
| 2005/0000900 A1 | 1/2005 | Huang et al. |

| | | | |
|---|---|---|---|
| 2005/0019792 A1 | 1/2005 | McBride et al. | |
| 2005/0037471 A1 | 2/2005 | Liu et al. | |
| 2005/0053952 A1 | 3/2005 | Hong et al. | |
| 2005/0065735 A1 | 3/2005 | Lee et al. | |
| 2005/0084421 A1 | 4/2005 | Unger et al. | |
| 2005/0123947 A1 | 6/2005 | Quake et al. | |
| 2005/0129581 A1 | 6/2005 | McBride et al. | |
| 2005/0145496 A1 | 7/2005 | Goodsaid et al. | |
| 2005/0164376 A1 | 7/2005 | Balagadde et al. | |
| 2005/0180891 A1 | 8/2005 | Webster et al. | |
| 2005/0197652 A1 | 9/2005 | Nat | |
| 2005/0221373 A1 | 10/2005 | Enzelberger et al. | |

FOREIGN PATENT DOCUMENTS

| | | |
|---|---|---|
| EP | 0 703 364 A1 | 3/1996 |
| EP | 0 706 004 A2 | 4/1996 |
| EP | 0 745 682 B1 | 12/1996 |
| EP | 0 778 351 B1 | 6/1997 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| EP | 1 065 378 A2 | 1/2001 |
| GB | 2 097 692 A | 11/1982 |
| GB | 2 155 152 A | 9/1985 |
| GB | 2 264 296 A | 8/1993 |
| GB | 2 264 496 A | 9/1993 |
| GB | 2 308 460 A | 6/1997 |
| WO | WO 91/13338 A2 | 9/1991 |
| WO | WO 91/15750 A1 | 10/1991 |
| WO | WO 94/05414 A1 | 3/1994 |
| WO | WO 95/33846 A1 | 12/1995 |
| WO | WO 95/33853 A1 | 12/1995 |
| WO | WO 97/02357 A1 | 1/1997 |
| WO | WO 97/38300 A1 | 10/1997 |
| WO | WO 98/07069 A1 | 2/1998 |
| WO | WO 98/08931 A1 | 3/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 00/00678 A1 | 1/2000 |
| WO | WO 00/43748 A1 | 7/2000 |
| WO | WO 00/60345 A1 | 10/2000 |
| WO | WO 01/01025 A2 | 1/2001 |
| WO | WO 01/06529 A1 | 1/2001 |
| WO | WO 01/06575 A1 | 1/2001 |
| WO | WO 01/09595 A2 | 2/2001 |
| WO | WO 01/32930 A1 | 5/2001 |
| WO | WO 01/94635 A2 | 12/2001 |
| WO | WO 02/60582 A2 | 8/2002 |
| WO | WO 02/82047 A2 | 10/2002 |
| WO | WO 03/037781 A1 | 5/2003 |

OTHER PUBLICATIONS

"Biochips," Nature Biotechnology, Vol. 18, Supplement 2000, pp. IT43-IT44, 2000.
"Chapter 9: Microfluidic Devices," Micromachined Transducers Sourcebook, pp. 779-882, 1998.
"Last Chance For Micromachines," The Economist Technology Quarterly, 8pages, Dec. 7, 2000.
"The Liver Chip," Technology Review, pp. 64-67, Mar. 2003.
Affholter, Joseph et al., "Engineering A Revolution," Chemistry in Britain, pp. 48-51, Apr. 1999.
Ahn, Chong H. et al., "Fluid Micropumps Based On Rotary Magnetic Actuators," Proceedings of 1995 IEEE Micro Electro Mechanical Systems Workshop (MEMS '95), Amsterdam, Netherlands, pp. 408-412, Jan. 29 - Feb. 2, 1995.
Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, James B. et al., "Silicon Micromechanical Devices," Scientific American, pp. cover, 44-55, Apr. 1983.
Armani, Deniz et al., "Re-Configurable Fluid Circuits by PDMS Elastomer Micromachining," IEEE Int. Conf. Micro Electro Mech. Syst. Tech. Digest, Vol. 12, pp. 222-227, 1999.
Arnold, Frances H., "Design By Directed Evolution," Accounts of Chemical Research, Vol. 31, No. 3, pp. 125-131, 1998.
Ballantyne, J. P. et al., "Selective Area Metallization By Electron-Beam Controlled Direct Metallic Deposition," J. Vac. Sci. Technol., Vol. 10, No. 6, pp. 1094-1097, Nov. 1973.
Bein, Thomas, "Efficient Assays For Combinatorial Methods For The Discovery Of Catalysts," Angew. Chem. Int. Ed., Vol. 38, No. 3, pp. 323-326, 1999.
Belgrader, Phillip et al., "Rapid Pathogen Detection Using A Microchip PCR Array Instrument," Clinical Chemistry, Vol. 44, No. 10, pp. 2191-2194, 1998.
Benard, W. L. et al., "A Titanium-Nickel Shape-Memory Alloy Actuated Micropump," Transducers '97, 1997 International Conference on Solid-State Sensors and Actuators, Chicago, Illinois, pp. 361-364, Jun. 16-19, 1997.
Black, Harvey, "Tiny Technology Promises Tremendous Profits," The Scientist, Vol. 15, No. 21, 4 pages, Oct. 29, 2001.
Bloomstein, T. M. et al., "Laser-Chemical Three-Dimensional Writing For Microelectromechanics And Application To Standard-Cell Microfluidics," J. Vac. Sci. Technol. B, Vol. 10, No. 6, pp. 2671-2674, Nov. 1992.
Bousse, Luc et al., "Electrokinetically Controlled Microfluidic Analysis Systems," Annu. Rev. Biophys. Biomol. Struct., Vol. 29, pp. 155-181, 2000.
Brechtel, R. et al., "Control Of The Electroosmotic Flow By Metal-Salt-Containing Buffers," Journal of Chromatography A, vol. 716, pp. 97-105, 1995.
Brush, Michael, "Automated Laboratories," The Scientist, vol. 13, No. 4, 10 pages, Feb. 15, 1999.
Bryzek, Janusz et al., "Micromachines On The March", IEEE Spectrum, vol. 31, No. 5, pp. 20-31, May 1994.
Buchaillot, Lionel et al., "Silicon Nitride Thin Films Young's Modulus Determination By An Optical Non Destructive Method," Jpn. J. Appl. Phys., vol. 36, Part 2, No. 6B, pp. L794-L797, Jun. 15, 1997.
Budowle, Bruce et al., "Analysis Of The VNTR Locus DIS80 By The PCR Followed By High-Resolution Page," Am. J. Hum. Genet., vol. 48, pp. 137-144, 1991.
Calkins, Kathryn, "Mycometrix: Rubber Chips," BioCentury, 2 pages, Oct. 16, 2000.
Chang, Jun Keun et al., "Functional Integration Of Serial Dilution And Capillary Electrophoresis On A PDMS Microchip," Biotechnology and Bioprocess Engineering, vol. 8, No. 4, pp. 233-239, 2003.
Chen, Chihchen et al., "Gray-Scale Photolithography Using Microfluidic Photomasks," PNAS, Vol. 100, No. 4, pp. 1499-1504, Feb. 18, 2003.
Chiu, Daniel T. et al., "Patterned Deposition Of Cells And Proteins Onto Surfaces By Using Three-Dimensional Microfluidic Systems," *PNAS*, vol. 97, No. 6, pp. 2408-2413, Mar. 14, 2000.
Chou, Hou-Pu et al., "A Microfabricated Device For Sizing And Sorting DNA Molecules," Proc. Natl. Acad. Sci., vol. 96, pp. 11-13, Jan. 1999.
Chou, Hou-Pu et al., "A Microfabricated Rotary Pump," Biomedical Microdevices, vol. 3, No. 4, pp. 323-330, 2001.
Chou, Hou-Pu et al., "Integrated Elastomer Fluidic Lab-On-A-Chip-Surface Patterning And DNA Diagnostics," Proceedings of the Solid State Actuator and Sensor Workshop, Hilton Head, South Carolina, 4 pages, 2000.
Chou, Hou-Pu, "Microfabricated Devices For Rapid DNA Diagnostics," Doctoral Thesis, California Institute of Technology, pp. i-xii and 1-106, May 30, 2000.
Chou, Hou-Pu et al., "Multiple Disease Diagnostics On A Single Chip," Biophysics Lab, Caltech, pp. 1-4, Mar. 1, 2000.
Crosland-Taylor, P. J., "A Device For Counting Small Particles Suspended In A Fluid Through A Tube," Nature, vol. 171, pp. 37-38, Jan. 3, 1953.
Davila, Herman Moreno, "Molecular And Functional Diversity Of Voltage-Gated Calcium Channels," Annals of the New York Academy of Sciences, vol. 868, pp. cover. 102-117, 1999.

Delamarche, Emmanuel et al., "Patterned Delivery Of Immunoglobulins To Surfaces Using Microfluidic Networks," Science, vol. 276, pp. 779-781, May 2, 1997.
Duffy, David C. et al., "Patterning Electroluminescent Materials With Feature Sizes As Small As 5pm Using Elastomeric Membranes As Masks For Dry Lift-Off," Advanced Materials, vol. 11, No. 7, pp. 546-552, 1999.
Duffy, David C. et al., "Rapid Prototyping Of Microfluidic Switches In Poly(dimethyl siloxine) And Their Actuation By Electro-Osmotic Flow," J. Micromech. Microeng., vol. 9, pp. 211-217, 1999.
Duffy, David C. et al., "Rapid Prototyping Of Microfluidic Systems In Poly(dimethylsiloxane)," Analytical Chemistry, vol. 70, No. 23, pp. 4974-4984, Dec. 1, 1998.
Effenhauser, Carlo S. et al., "Integrated Capillary Electrophoresis On Flexible Silicone Microdevices: Analysis Of DNA Restriction Fragments And Detection Of Single DNA Molecules On Microchips," Analytical Chemistry, vol. 69, No. 17, pp. 3451-3457, Sep. 1, 1997.
Effenhauser, Carlo S. et al., "Integrated Chip-Based Capillary Electrophoresis," Electrophoresis, vol. 18, pp. 2203-2213, 1997.
Eyal, Shulamit et al., "Velocity-Independent Microfluidic Flow Cytometry," Electrophoresis, vol. 23, pp. 2653-2657, 2002.
Fahrenberg, J. et al., "A Microvalve System Fabricated By Thermoplastic Molding," J. Micromech. Microeng., vol. 5, pp. 169-171, 1995.
Fettinger, J. C. et al., "Stacked Modules For Micro Flow Systems In Chemical Analysis: Concept and Studies Using An Enlarged Model," Sensors and Actuators B, vol. 17, pp. 19-25, 1993.
Fitzgerald, Deborah A., "Making Every Nanoliter Count," The Scientist, vol. 15, No. 21, 8 pages, Oct. 29, 2001.
Folch, A. et al., "Molding Of Deep Polydimethylsiloxane Microstructures For Microfluidics And Biological Applications," Journal of Biomechanical Engineering, vol. 121, pp. 28-34, Feb. 1999.
Fu, Anne Y. et al., "A Microfabricated Fluorescence-Activated Cell-Sorter," Nature Biotechnology, vol. 17, pp. 1109-1111, Nov. 1999.
Galambos, Paul et al., "Electrical And Fluidic Packaging Of Surface Micromachined Electro- Microfluidic Devices," 8 pages, No date.
Gao, Jun et al., "Integrated Microfluidic System Enabling Protein Digestion, Peptide Separation, And Protein Identification," Analytical Chemistry, vol. 73, No. 11, pp. 2648-2655, Jun. 1, 2001.
Garno, Jayne C. et al., "Production Of Periodic Arrays Of Protein Nanostructures Using Particle Lithography," Langmuir, vol. 18, No. 21, pp. 8186-8192, 2002.
Gass, V. et al., "Integrated Flow-Regulated Silicon Micropump," Sensors and Actuators A, vol. 43, pp. 335-338, 1994.
Gerlach, Torsten, "Pumping Gases By A Silicon Micro Pump With Dynamic Passive Valves," Transducers '97, 1997 International Conference on Solid-State Sensors and Actuators, Chicago, Illinois, pp. 357-360, Jun. 16-19, 1997.
Giusti, Alan et al., "Application Of Deoxyribonucleic Acid (DNA) Polymorphisms To The Analysis Of DNA Recovered From Sperm," Journal of Forensic Sciences, vol. 31, No. 2, pp. 409-417, Apr. 1986.
Goll, C. et al., "Microvalves With Bistable Buckled Polymer Diaphragms," J. Micromech. Microeng., vol. 6, pp. 77-79, 1996.
Gonzalez, Jesus E. et al., "Improved Indicators Of Cell Membrane Potential That Use Fluorescence Resonance Energy Transfer," Chemistry & Biology, vol. 4, No. 4, pp. 269-277, Apr. 1997.
Gravesen, Peter et al., "Microfluidics-A Review," J. Micromech. Microeng., vol. 3, pp. 168-192, 1993.
Greene, Chana, "Characterizing The Properties Of PDMS," pp. 1-11, Summer 2000.
Grover, William H. et al., "Monolithic Membrane Valves And Diaphragm Pumps For Practical Large-Scale Integration Into Glass Microfluidic Devices," Sensors and Actuators B, vol. 89, pp. 315-323, 2003.
Guerin, L. J. et al., "Simple And Low Cost Fabrication Of Embedded Micro-Channels By Using A New Thick-Film Photoplastic," Transducers '97, 1997 International Conference on Solid-State Sensors and Actuators, Chicago, Illinois, pp. 1419-1422, Jun. 18-19, 1997.
Hanes, Jozef, et al., "In Vitro Selection And Evolution Of Functional Proteins By Using Ribosome Display," Proc. Natl. Acad. Sci. USA, vol. 94, pp. 4937-4942, May 1997.

Hansen, Carl. L. et al., "A Robust And Scalable Microfluidic Metering Method That Allows Protein Crystal Growth By Free Interface Diffusion," PNAS, vol. 99, No. 26, pp. 16531-16536, Dec. 24, 2002.
Hansen, Carl L. et al., "Systematic Investigation Of Protein-Phase Behavior With A Microfluidic Formulator," PNAS Early Edition, 6 pages, 2004.
Harrison, D. Jed et al., "Micromachining A Miniaturized Capillary Electrophoresis-Based Chemical Analysis System On A Chip," Science, vol. 261, pp. 895-897, Aug. 13, 1993.
Hermanson, Greg T. et al., "Chapter 2 - Activation Methods," Immobilized Affinity Ligand Techniques, Academic Press, pp. 2 cover pp., 51-136, 1992.
Hicks, Jennifer, "Genetics And Drug Discovery Dominate Microarray Research," R&D Magazine, pp. 28-33, Feb. 1999.
Hoffmuller, Ulrich et al., 'In Vitro Evolution And Selection Of Proteins: Ribosome Display For Larger Libraries; Angew. Chem. Int. Ed., vol. 37, No. 23, pp. 3241-3243, 1998.
Hofmann, Oliver et al., "Modular Approach To Fabrication Of Three-Dimensional Microchannel Systems in PDMS—Application To Sheath Flow Microchips," Lab on a Chip, vol. 1, pp. 108-114, 2001.
Hong, Jong Wook et al., "A Nanoliter-Scale Nucleic Acid Processor With Parallel Architecture," Nature Biotechnology, vol. 22, No. 4, pp. 1-5, Apr. 2004.
Hornbeck, Larry J. et al., "Bistable Deformable Mirror Device," Spatial Light Modulators and Applications 1988 Technical Digest Series, Summaries of papers presented at the Spatial Light Modulators and Applications Topical Meeting, Optical Society of America, vol. 8, Postconference Edition, A215, pp. 107-110, Jun. 15-17, 1988.
Hosokawa, Kazuo et al., "A Microfluidic Device For Mixing Of Capillary-Driven Liquids," IEEJ Trans. SM, vol. 123, No. 1, pp. 23-24, 2003.
Hosokawa, Kazuo et al., "Handling Of Picoliter Liquid Samples In A Poly(dimethylsiloxane)-Based Microfluidic Device," Analytical Chemistry, vol. 71, No. 20, pp. 4781-4785, Oct. 15. 1999.
Ikuta, Koji et al., "Three Dimensional Micro Integrated Fluid Systems (MIFS) Fabricated By Stereo Lithography," IEEE, pp. 1-6, 1994.
Jacobson, Ken et al., "International Workshop On The Application Of Fluorescence Photobleaching Techniques To Problems In Cell Biology," Federation Proceedings, vol. 42, No. 1, pp. 72-79, Jan. 1983.
Jacobson, Stephen C. et al., "High-Speed Separations On A Microchip," Analytical Chemistry, vol. 66, No. 7, pp. 1114-1118, Apr. 1, 1994.
Jacobson, Stephen C. et al., "Microfluidic Devices For Electrokinetically Driven Parallel And Serial Mixing," Analytical Chemistry, vol. 71, No. 20, pp. 4455-4459, Oct. 15, 1999.
Jeffreys, Alec J. et al., "Hypervariable 'Minisatellite' Regions In Human DNA," Nature, vol. 314, pp. 67-73, Mar. 7, 1985.
Jerman, Hal, "Electrically-Activated, Normally-Closed Diaphragm Valves," Transducers '91, 1991 International Conference on Solid-State Sensors and Actuators, pp. cover, 1045-1048, 1991.
Jermutus, Lutz, et al., "Recent Advances In Producing And Selecting Functional Proteins By Using Cell-Free Translation," Current Opinion in Biotechnology, vol. 9, pp. 534-548, 1998.
Jo, Byung-Ho et al., "Fabrication Of Three-Dimensional Microfluidic Systems By Stacking Molded Polydimethylsiloxane (PDMS) Layers" SPIE, vol. 3877, pp. 222-229. Sep. 1999.
Jo, Byung-Ho et al., "Three-Dimensional Micro-Channel Fabrication In Polydimethylsiloxane (PDMS) Elastomer," Journal of Microelectromechanical Systems, vol. 9, No. 1, pp. 76-81, Mar. 2000.
Ju, Li-Ya et al., "Application Of Silver Staining To The Rapid Typing Of The Polymorphism Of HLA-DQ Alleles By Enzymatic Amplification and Allele-Specific Restriction Fragment Length Polymorphism," Electrophoresis, vol. 12, pp. 270-273, 1991.
Juarez-MARTINEZ, G. et al., "High-Throughput Screens For Postgenomics: Studies Of Protein Crystallization Using Microsystems Technology," Analytical Chemistry, vol. 74, No. 14, pp. 3505-3510, Jul. 15, 2002.
Jung, D. R. et al., "Chemical And Physical Interactions At Metal/Self-Assembled Organic Monolayer Interfaces," pp. 1-54, 1994.

Kagan, C. R., "Organic-Inorganic Hybrid Materials As Semiconducting Channels In Thin-Film Field-Effect Transistors," Science, vol. 286, pp. 945-947, Oct. 29, 1999.

Kanter, Evan et al., "Analysis Of Restriction Fragment Length Polymorphisms In Deoxyribonucleic Acid (DNA) Recovered From Dried Bloodstains," Journal of Forensic Sciences, vol. 31, No. 2, pp. 403-408, Apr. 1986.

Kapur, Ravi et al., "Fabrication And Selective Surface Modification Of 3-Dimensionally Textured Biomedical Polymers From Etched Silicon Substrates," Journal of Biomedical Materials Research, vol. 33, pp. 205-216, 1996.

Kenis, Paul J. A. et al., "Microfabrication Inside Capillaries Using Multiphase Laminar Flow Patterning," Science, vol. 285, pp. 83-85, Jul. 2, 1999.

Khoo, Melvin et al., "A Novel Micromachined Magnetic Membrane Microfluid Pump," pp. 1-4, no date.

Kim, Enoch et al., "Micromolding In Capillaries: Applications In Materials Science," J. Am. Chem. Soc., vol. 118, No. 24, pp. 5722-5731, 1996.

Kim, Enoch et al., "Polymer Microstructures Formed By Moulding In Capillaries," Nature, vol. 376, pp. 581-584, Aug. 17, 1995.

Kirk-Othmer, "Concise Encyclopedia of Chemical Technology," John Wiley & Sons, 5 pages, no date.

Kopp, Martin U. et al., "Chemical Amplification: Continuous-Flow PCR On A Chip," Science, vol. 280, pp. 1046-1048, May 15, 1998.

Kuhn, Lawrence et al., "Silicon Charge Electrode Array For Ink Jet Printing," IEEE Transactions on Electron Devices, vol. ED-25, No. 10, pp. 1257-1260, Oct. 1978.

Kumar, Amit et al., "Features Of Gold Having Micrometer To Centimeter Dimensions Can Be Formed Through A Combination Of Stamping With An Elastomeric Stamp And An Alkanethiol 'Ink' Followed By Chemical Etching," Appl. Phys. Lett., vol. 63, No. 14, pp. 2002-2004, Oct. 4, 1993.

Kumar, Amit et al.. "Patterning Self-Assembled Monolayers: Applications In Materials Science," Langmuir, vol. 10, pp. 1498-1511, 1994.

Lagally, Eric T. et al., "Fully Integrated PCR-Capillary Electrophoresis Microsystem For DNA Analysis," Lab On A Chip, vol. 1, pp. 102-107, 2001.

Lagally, Eric T. et al., "Monolithic Integrated Microfluidic DNA Amplification And Capillary Electrophoresis Analysis System." Sensors and Actuators B, vol. 63, pp. 138-146, 2000.

Lagally, E. T. et al., "Single-Molecule DNA Amplification And Analysis In An Integrated Microfluidic Device," Analytical Chemistry, vol. 73, No. 3, pp. 565-570, Feb. 1, 2001.

Lammerink, T.S.J. et al., "Modular Concept For Fluid Handling Systems," IEEE pp. 389-394, 1996.

Levine, Leanna M. et al., "Measurement Of Specific Protease Activity Utilizing Fluorescence Polarization," Analytical Biochemistry, vol. 247, pp. 83-88, 1997.

Li, Paul C. H. et al., "Transport, Manipulation, And Reaction of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source For Mass Spectrometry," Analytical Chemistry, vol. 72, No. 2, pp. 367-375, Jan. 15, 2000.

Lin, L. Y. et al., "Free-Space Micromachined Optical Switches For Optical Networking," IEEE Journal of Selected Topics in Quantum Electronics, vol. 5, No. 1, pp. 4-9, Jan. 1999.

Liu, Jian et al., "A Nanoliter Rotary Device For Polymerase Chain Reaction," Electrophoresis, vol. 23, pp. 1531-1536, 2002.

Llopis, Juan et al., "Ligand-Dependent Interactions Of Coactivators Steroid Receptor Coactivator-1 And Peroxisome Proliferator-Activated Receptor Binding Protein With Nuclear Hormone Receptors Can Be Imaged In Live Cells And Are Required For Transcription," PNAS, vol. 97, No. 8, pp. 4363-4368, Apr. 11, 2000.

Lötters, J C et al., "The Mechanical Properties Of The Rubber Elastic Polymer Polydimethylsiloxane For Sensor Applications," J. Micromech. Microeng., vol. 7, pp. 145-147, 1997.

Lucy, Charles a. et al., "Characterization Of The Cationic Surfactant Induced Reversal Of Electroosmotic Flow In Capillary Electrophoresis," Anal. Chem., vol. 68, pp. 300-305, 1996.

Mahajan, Nupam P. et al., "Novel Mutant Green Fluorescent Protein Protease Substrates Reveal The Activation Of Specific Caspases During Apoptosis," Chemistry & Biology, vol. 6. No. 6, pp. 401- 409, Jun. 1999.

Maluf, N., "An Introduction To Microelectromechanical Systems Engineering," Artech House Publishers, Boston London, pp. 42-45. Dec. 1999.

Manz, a. et al., "Micromachining Of Monocrystalline Silicon And Glass For Chemical Analysis Systems," Trends in Analytical Chemistry, vol. 10, No. 5, pp. 144-149, 1991.

Marshall, SID, "Fundamental Changes Ahead For Lab Instrumentation," R&D Magazine, 5 pages, Feb. 1999.

Marsili, Ray, "Lab-On-A-Chip Poised to Revolutionize Sample Prep," R&D Magazine, 5 pages, Feb. 1999.

McDonald, J. Cooper et al., "Fabrication of Microfluidic Systems In Poly(dimethylsiloxane)," Electrophoresis, vol. 21, pp. 27-40, 2000.

McDonald, J. Cooper et al., °Poly(dimethyisiloxane) As A Material"For Fabricating Microfluidic Devices," Accounts of Chemical Research, vol. 35, No. 7, pp. 491-499, 2002.

Moldavan, Andrew, "Photo-Electric Technique For The Counting Of Microscopical Cells," Science, vol. 80, No. 2069, pp. 188-189, Aug. 24, 1934.

Muller, Richard S. et al., "Surface-Micromachined Microoptical Elements And Systems," Proceedings of the IEEE, vol. 86, No. 8, pp. 1705-1720, Aug. 1998.

Murray, Vincent et al., "Detection Of Polymorphisms Using Thermal Cycling With A Single Oligonucleotide On A DNA Sequencing Gel," Human Mutation, vol. 2, pp. 118-122, 1993.

Nagai, Yasuo et al., "A Fluorescent Indicator For Visualizing cAMP-Induced Phosphorylation In Vivo," Nature Biotechnology, vol. 18, pp. 313-316, Mar. 2000.

Nakamura, Yusuke et al., "Variable Number Of Tanden Repeat (VNTR) Markers For Human Gene Mapping," Science, vol. 235, pp. 1616-1622, Mar. 27, 1987.

Ng, Jessamine M. K. et al., "Components For Integrated Poly(Dimethylsiloxane) Microfluidic Systems," Electrophoresis, vol. 23, pp. 3461-3473, 2002.

Oleschuk, Richard D. et al., "Analytical Microdevices For Mass Spectrometry," Trends In Analytical Chemistry, vol. 19, No. 6., pp. 379-388, 2000.

Olsson, Anders et al., "Simulation Studies Of Diffuser And Nozzle Elements For Valve-Less Micropumps," Transducers '97, 1997 International Conference on Solid-State Sensors and Actuators, Chicago, Illinois, pp. 1039-1042, Jun. 16-19, 1997.

Parker, Gregory J. et al., "Development Of High Throughput Screening Assays Using Fluorescence Polarization: Nuclear Receptor-Ligand-Binding And Kinase/Phophatase Assays," Journal of Biomolecular Screening, vol. 5, No. 2, pp. 77-88, 2000.

Pethig, Ronald et al., "Applications Of Dielectrophoresis In Biotechnology," Tibtech, vol. 15, pp. 426-432, Oct. 1997.

Qin, Dong et al., "Elastomeric Light Valves," Adv. Mater., vol. 9, No. 5, pp. 407-410, 1997.

Qin, Dong et al., "Photolithography With Transparent Reflective Photomasks," J. Vac. Sci. Technol. B, vol. 16, No. 1, pp. 98-103, Jan. 1998.

Quake, Stephen R. et al., "From Micro-To Nanofabrication With Soft Materials," Science, vol. 290, pp. 1536-1540, Nov. 24, 2000.

Rapp, R. et al., "LIGA Micropump For Gases And Liquids," Sensors and Actuators A, vol. 40, pp. 57- 61, Jan. 1994.

Roberts, Richard W. et al., "RNA-Peptide Fusions For The In Vitro Selection Of Peptides And Proteins," Proc. Natl. Acad. Sci. USA, vol. 94, pp. 12297-12302, Nov. 1997.

Rouhi, Maureen, "Sizing, Sorting DNA One Piece At A Time," C&EN, pp. 5-6, Jan. 11, 1999.

Roylance, Lynn Michelle et al., "A Batch-Fabricated Silicon Accelerometer," IEEE Transactions on Electron Devices, vol. ED-26, No. 12, pp. 1911-1917, Dec. 1979.

Sandia National Laboratories, "Electro Microfluidic Dual In-Line Package (EMDIP)," 2 pages, no date.

Sanjoh, Akira et al., "Spatiotemporal Protein Crystal Growth Studies Using Microfluidic Silicon Devices," Journal of Crystal Growth, vol. 196, pp. 691-702, 1999.

Sasserath, J. et al., "Rapid Prototyping And Development Of Microfluidic And BioMEMS Devices," IVD Technology, 12 pages, Jun. 2002.

Schasfoort, Richard B. M. et al., "Field-Effect Flow Control For Microfabricated Fluidic Networks," Science, vol. 286, pp. 942-945, Oct. 29, 1999.

Schueller, Olivier J. A. et al., "Fabrication Of Glassy Carbon Microstructures By Soft Lithography," Sensors and Actuators A, vol. 72, pp. 126-139, 1999.

Seethala, Ramakrishna et al., "A Fluorescence Polarization Competition Immunoassay For Tyrosine Kinases," Analytical Biochemistry, vol. 255, pp. 257-262, 1998.

Shoji, Shuichi, "Fluids For Sensor Systems," Topics in Current Chemistry, vol. 194, pp. 163-188, 1998.

Shoji, Shuichi et al., "Smallest Dead volume Microvalves For Integrated Chemical Analyzing Systems," Transducers '91, 1991 International Conference on Solid-State Sensors and Actuators, San Francisco, California, pp. cover, 1052-1055, 1991.

Smits, J.G., "Piezoelectric Micropump With Three Valves Working Peristaltically," Sensors and Actuators, vol. A21-A23, pp. 203-206, 1990.

Sohn, L. L. et al., "Capacitance Cytometry: Measuring Biological Cells One By One," PNAS, vol. 97, No. 20, pp. 10687-10690, Sep. 26, 2000.

Takahashi, Akiyuki et al., "Measurement Of Intracellular Calcium," Physiological Reviews, vol. 79, No. 4, pp. 1089-1125, Oct. 1999.

Tatari, Zohreh et al., "HLA-Cw Allele Analysis By PCR-Restriction Fragment Length Polymorphism: Study Of Known And Additional Alleies," Proc. Natl. Acad. Sci. Usa, vol. 92, pp. 8803-8807, Sep. 1995.

Tawfik, Dan S. et al., "Man-Made Cell-Like Compartments For Molecular Evolution," Nature Biotechnology, vol. 16, pp. 652-656, Jul. 1998.

Thompson, L. F. et al., "Introduction To Microlithography," 185th Meeting of the American Chemical Society, Seattle, WA, pp. 2 cover pages, 1-13, Mar. 20-25, 1983.

Thorsen, Todd et al., "Dynamic Pattern Formation In A Vesicle-Generating Microfluidic Device," Physical Review Letters, vol. 86, No..18, pp. 4163-4166, Apr. 30, 2001.

Thorsen, Todd et al., "Microfluidic Large-Scale Integration," Science, vol. 298, No. 5593, pp. 580-584, Oct. 18, 2002.

Tufte, O. N. et al., "Silicon Diffused-Element Piezoresistive Diaphragms," Journal of Applied Physics, vol. 33, No. 11, pp. 3322-3327, Nov. 1962.

Ullmann's Encyclopedia of Industrial Chemistry, Sections 6 to 6.3, Topic: Carbon Black, Sixth Edition, 7 pages, 1999.

Unger, Marc A. et al., "Monolithic Microfabricated Valves And Pumps By Multilayer Soft Lithography," Science, vol. 288, pp. 113-116, Apr. 7, 2000.

Van De Pol, F.C.M. et al., "A Thermo-Pneumatic Actuation Principle For A Microminiature Pump And Other Micromechanical Devices," Sensors and Actuators, vol. 17, Nos. 1-2, pp. 139-143, May 3, 1989.

Van De Pol, F.C.M. et al., "Micro Liquid Handling Devices—A Review," Micro Systems Technologies, vol. 90, pp. 799-805, 1990.

Van Den Berg, A. et al., "Micro Total Analysis Systems," Proceedings of The μTAS '94 Workshop, University of Twente, The Netherlands, 17 pages., Nov. 21-22, 1994.

Van Der Woerd, Mark et al., "Lab-On-A-Chip Based Protein Crystallization," National Aeronautics and Space Administration and Caliper, pp. 1-27, Oct. 25, 2001.

Van Der Woerd, Mark et al., "The Promise Of Macromolecular Crystallization In Microfluidic Chips," Journal of Structural Biology, vol. 142, pp. 180-187, 2003.

Van Dilla, M. A. et al., "Cell Microfluormetry: A Method For Rapid Fluorescence Measurement," Science, vol. 163, pp. 1213-1214, Mar. 14, 1969.

Velev, Orlin D., "On-Chip Manipulation Of Free Droplets," Nature, vol. 426, pp. 515-516, Dec. 4, 2003.

Verpoorte, Elisabeth M. J. et al., "Three-Dimensional Micro Flow Manifolds For Miniaturized Chemical Analysis Systems," J. Micromech. Microeng., vol. 7, pp. 246-256, 1994.

Vieider, Christian et al., "A Pneumatically Actuated Micro Valve With A Silicon Rubber Membrane For Integration With Fluid Handling Systems," Transducers '95, 8th International Conference on Solid- State Sensors and Actuators and Eurosensors Ix, Stockholm, Sweden, pp. 284-286, Jun. 25-29, 1995.

Vogelstein, Bert et al., "Digital PCR," Proc. Natl. Acad. Sci. Usa, Vol. 96, pp. 9236-9241, Aug. 1999.

Washizu, Masao et al., "Molecular Dielectrophoresis Of Biopolymers," IEEE Transactions on Industry Applications, vol. 30, No. 4, pp. 835-843, Jul. 1994.

Whelen, A. Christian et al., "The Role Of Nucleic Acid Amplification And Detection In The Clinical Microbiology Laboratory," Annu. Rev. Microbiol., vol. 50, pp. 349-373, 1996.

Whitesides, George M. et al., "Flexible Methods for Microfluidics," Physics Today, pp. 42-48, Jun. 2001.

Whitesides, George M. et al., "Soft Lithography In Biology And Biochemistry," Annu. Rev. Biomed. Eng., vol. 3, pp. 335-373, 2001.

Wilbur, James L. et al., "Lithographic Molding: A Convenient Route To Structures With Sub- Micrometer Dimensions," Adv. Mater., vol. 7, No. 7, pp. 649-652, 1995.

Wu, Hongkai et al.; "Fabrication Of Complex Three-Dimensional Microchannel Systems In PDMS," J. Am. Chem. Soc., vol. 125, No. 2, pp. 554-559, 2003.

Xia, Younan et al., "Complex Optical Surfaces Formed By Replica Molding Against Elastomeric Masters," Science, vol. 273, pp. 347-349, Jul. 19, 1996.

Xia, Younan et al., "Micromolding Of Polymers In Capillaries: Applications In Microfabrication," Chem. Mater., vol. 8, No. 7, pp. 1559-1566, 1996.

Xia, Younan et al., "Reduction In The Size Of Features Of Patterned SAMs Generated By Microcontact Printing With Mechanical Compression Of The Stamp," Adv. Mater., vol. 7, No. 5, pp. 471-473, 1995.

Xia, Younan et al., "Soft Lithography," Angew. Chem. Int. Ed., vol. 37, pp. 551-575, 1998.

Xu, Bing et al., "Making Negative Poisson's Ratio Microstructures By Soft Lithography," Adv. Mater., vol. 11, No. 14, pp. 1186-1189, 1999.

Xu, Xiang et al., "Detection Of Programmed Cell Death Using Fluorescence Energy Transfer," Nucleic Acids Research, vol. 26, No. 8, pp. 2034-2035, 1998.

Yang, Xing et al., "A Low Power MEMS Silicone/Parylene Valve," Solid-State Sensor and Actuator Workshop, Hilton Head Island, South Carolina, 4 pp., Jun. 7-11, 1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Young, a. M. et al., "Contoured Elastic-Membrane Microvalves For Microfluidic Network Integration," Journal of Biomechanical Engineering, vol. 121, pp. 2-6, Feb. 1999.

Zaccolo, Manuela et al., "A Genetically Encoded, Fluorescent Indicator For Cyclic AMP In Living Cells," Nature Cell Biology, vol. 2, pp. 25-29, Jan. 2000.

Zengerle, R. et al., "A Micro Membrane Pump With Electrostatic Actuation," Micro Electro Mechanical Systems '92, Travemünde, Germany, pp. 19-24, Feb. 4-7, 1992.

Zengerle, R. et al., "Performance Simulation Of Microminiaturized Membrane Pumps," 7th International Conference on Solid-State Sensors and Actuators, Yokohama, Japan, pp. 2 cover pages, 106-109, Jun. 7-10, 1993.

Zhao, Zhan, et al., "An Integrated Biochip Design And Fabrication," Proceedings of SPIE. vol. 4936, pp. 321-326, 2002.

Zheng, Bo et al., "A Droplet-Based, Composite PDMS/Glass Capillary Microfluidic System For Evaluating Protein Crystallization Conditions By Microbatch And Vapor-Diffusion Methods With On-Chip X-Ray Diffraction," Angew. Chem., pp. 1-4, 2004.

Anderson, Janelle R. et al., "Fabrication Of Topologically Complex Three-Dimensional Microfluidic Systems In PDMS By Rapid Prototyping," Analytical Chemistry, vol. 72, No. 14, pp. 3158-3164, Jul. 15, 2000.

Ashkin, A. et al., "Optical Trapping And Manipulation Of Single Cells Using Infrared Laser Beams," Nature, vol. 330, No. 24, pp. 769-771, Dec. 31, 1987.

Ashkin, A. et al., "Optical Trapping And Manipulation Of Viruses And Bacteria," Science, vol. 235, pp. 1517-1520, Mar. 20, 1987.

Barron, Annelise E. et al., "Capillary Electrophoresis Of DNA In Uncross-Linked Polymer Solutions," Journal of Chromatography A, vol. 652, pp. 3-16, 1993.

Barron, Annelise E. et al., "DNA Separations By Slab Gel And Capillary Electrophoresis—Theory And Practice," Separation and Purification Methods, vol. 24, No. 1, pp. 1-118, 1995.

Barron, Annelise E. et al., "The Use Of Coated And Uncoated Capillaries For The Electrophoretic Separation Of DNA In Dilute Polymer-Solutions," Electrophoresis, vol. 16, pp. 64-74, 1995.

Blanch, Harvey W. et al., Biochemical Engineering, pp. 2 cover pages and 305, 1996.

Blankenstein, Gert et al., "Modular Concept Of A Laboratory On A Chip For Chemical And Biochemical Analysis," Biosensors & Bioelectronics, vol. 13, Nos. 3-4, pp. 427-438, 1998.

Buican, Tudor N. et al., "Automated Single-Cell Manipulation And Sorting By Light Trapping," Applied Optics, vol. 26, No. 24, pp. 5311-5316, Dec. 15, 1987.

Burbaum, Jonathan J. et al., "New Technologies For High-Throughput Screening," Current Opinion in Chemical Biology, vol. 1, pp. 72-78, 1997.

CAI, Weiwen, et al., "High-Resolution Restriction Maps Of Bacterial Artificial Chromosomes Construted By Optical Mapping," Proc. Natl. Acad. Sci. USA, vol. 95, pp. 3390-3395, Mar. 1998.

Castro, Alonso et al., "Fluorescence Detection And Size Measurement Of Single DNA Molecules," Analytical Chemistry, vol. 65, No. 7, pp. 849-852, Apr. 1, 1993.

Chan, Jason H. et al., "Microfabricated Polymer Devices For Automated Sample Delivery Of Peptides For Analysis By Electrospray Ionization Tandem Mass Spectrometry," Analytical Chemistry, vol. 71, No. 20, pp. 4437-4444, Oct. 15, 1999.

Chiang, Yuh-Min et al., "Characterizing The Process Of Cast Molding Microfluidic Systems," SPIE vol. 3877, pp. 303-311, Sep. 1999.

Chiu, Chi-Sung et al., "Single Molecule Measurements Calibrate Green Fluorescent Protein Surface Densities On Transparent Beads For Use With 'Knock-In' Animals And Other Expression Systems," Journal of Neuroscience Methods, vol. 105, pp. 55-63, 2001.

Costerton, J. William et al., "Microbial Biofilms," Annu. Rev. Microbiol., vol. 49, pp. 711-745, 1995.

Cowen, S. et al., "An On-Chip Miniature Liquid Chromatography System: Design, Construction And Characterization," Micro Total Analysis Systems, Proceedings of the µTAS '94 Workshop, University of Twente, The Netherlands, pp. 2 cover pages and 295-298, 1995.

Delisa, Matthew P. et al., "Mapping Stress-Induced Changes In Autoinducer A1-2 Production In Chemostat-Cultivated *Escherichia coli* K-12," Journal of Bacteriology, vol. 183, No. 9, pp. 2918-2928, May 2001.

Dharmatilleke, Saman et al., "Three-Dimensional Silicone Device Fabrication And Interconnection Scheme For Microfluidic Applications Using Sacrificial Wax Layers," Micro-Electro-Mechanical Systems (MEMS), vol. 2, pp. 413-418, 2000.

Effenhauser, Carlo S., "Integrated Chip-Based Microcolumn Separation Systems," Topics in Current Chemistry, vol. 194, pp. cover, 52-82, 1998.

Effenhauser, Carlo S. et al., "Miniaturizing A Whole Analytical Laboratory Down To Chip Size," American Laboratory, vol. 26, No. 14, pp. cover, 15, 16, 18, 1994.

Ericson, Christer et al., "Electroomosis- And Pressure-Driven Chromatography In Chips Using Continuous Beds," Analytical Chemistry, vol. 72, No. 1, pp. 81-87, Jan. 1, 2000.

Felix, Arthur M. et al., "Pegylated IV—Enhanced Biological Activity Of Site-Directed Pegylated GRF Analogs," International Journal of Peptide & Protein Research, vol. 46, pp. 253-264, 1995.

Felix, Arthur M., "Site-Specific Poly(ethylene glycol)ylation Of Peptides," Poly(Ethylene Glycol) Chemistry and Biological Applications ACS Symposium Series 680, pp. 2 cover pages, 218-238, 1997.

Fiedler, Stefan et al., "Dielectrophoretic Sorting Of Particles And Cells In A Microsystem," Analytical Chemistry, vol. 70, No. 9, pp. 1909-1915, May 1, 1998.

Figeys, Daniel et al., "An Integrated Microfluidics-Tandem Mass Spectrometry System For Automated Protein Analysis," Analytical Chemistry, vol. 70, No. 18, pp. 3728-3734, Sep. 15, 1998.

Figeys, Daniel et al., "Nanoflow Solvent Gradient Delivery From A Microfabricated Device For Protein Identifications By Electrospray Ionization Mass Spectrometry," Analytical Chemistry, vol. 70, No. 18, pp. 3721-3727, Sep. 15, 1998.

Folch, A. et al., "Molding Of Deep Polydimethylsiloxane Microstructures For Microfluidics And Biological Applications," Journal of Biomechanical Engineering, vol. 121, pp. 28-34, Feb. 1999.

Fu, Anne Y. et al., "An Integrated Microfabricated Cell Sorter," Analytical Chemistry, vol. 74, No. 11, pp. 2451-2457, Jun. 1, 2002.

Fulwyler, M. J., "Electronic Separation Of Biological Cells By Volume," Science, pp. 910-911, Nov. 1965.

Geng, Xindu et al., "Retention Model For Proteins In Reversed-Phase Liquid Chromatography," Journal of Chromatography, vol. 296, pp. 15-30, 1984.

Gombotz, W. R. et al., "Pegylation: A Tool To Enhance Protein Delivery," Abstracts of Papers, American Chemical Society, vol. 217, Part 2, 2 pages, Mar. 21-25, 1999.

Goodwin, Peter M. et al., "Rapid Sizing Of Individual Fluorescently Stained DNA Fragments By Flow Cytometry," Nucleic Acids Research, vol. 21, No. 4, pp. 803-806, 1993.

Guerra, Patricia I. et al., "PEGylation Prevents The N-Terminal Degradation Of Megakaryocyte Growth And Development Factor," Pharmaceutical Research, vol. 15, No. 12, pp. 1822-1827, 1998.

Hancock, Robert E. W., "A Brief On Bacterial Biofilms," Nature Genetics, vol. 29, p. 360, Dec. 2001.

Harrison, D. Jed et al., "Integration Of Analytical Systems Incorporating Chemical Reactions And Electrphoretic Separation," Micro Total Analysis Systems, Proceedings of the µTAS '94 Workshop, University of Twente, The Netherlands, pp. 2 cover pages and 105-111, 1995.

Henion, Jack et al., "Capillary Electrophoresis/Mass Spectrometry: From One Meter Capillaries To Chip-Based Devices," 2 pages, 1999.

Heo, Jinseok et al., "A Microfluidic Bioreactor Based On Hydrogel-Entrapped *E coli*. Cell Viability, Lysis, And Intracellular Enzyme Reactions," Analytical Chemistry, vol. 75, No. 1, pp. 22-26, Jan. 1, 2003.

Herbert, D., "Continuous Culture Of Bacteria," The Journal of General Microbiology, vol. 15, pp. 2 cover pages and iv, 1956.

Herbert, D. et al., "The Continuous Culture Of Bacteria; A Theoretical And Experimental Study," J. Gen. Microbiol., vol. 14, pp. 601-622, 1956.

Hopfgartner, Gerard et al., "Exact Mass Measurement Of Product Ions For The Structural Elucidation Of Drug Metabolites With A Tandem Quadrupole Orthogonal-Acceleration Time-Of-Flight Mass Spectrometer," Journal of The American Society for Mass Spectrometry, vol. 10, pp. cover, 1305-1314, Dec. 1999.

Horn, Howard, "Lab Chips Sector: Microtechnologies Are Changing Healthcare And More," Life Sciences, pp. 19-21, Mar. 20, 2001.

Hosokawa, Kazuo et al., "Droplet-Based Nano/Picoliter Mixer Using Hydrophobic Microcapillary Vent," 1999 IEEE International Conference on Micro Electro Mechanical Systems, Technical Digest, pp. 388-393, 1999.

Ingraham, John L. et al., Growth Of The Bacterial Cell, pp. 3 cover pages and 230, 1983.

Jacobson, Stephen C. et al., "Open Channel Electrochromatography On A Microchip," Analytical Chemistry, vol. 66, No. 14, pp. 2369-2373, Jul. 15, 1994.

Jannasch, H.W. et al., "Experimental Bacterial Ecology Studied In Continuous Culture," Advances in Microbial Physiology, vol. 11, pp. cover and 165-212, 1974.

Kamentsky, Louis A. et al., "Spectrophotometer: New Instrument For Ultrarapid Cell Analysis," Science, vol. 150, pp. 630-631, Oct. 29, 1965.

Kawano, Yasushi et al., "Rapid Isolation And Identification Of Staphylococcal Exoproteins By Reverse Phase Capillary High Performance Liquid Chromatography-Electrospray Ionization Mass Spectrometry," FEMS Microbiology Letters, vol. 189, pp. 103-108, 2000.

Keller, Richard A. et al., "Single-Molecule Fluorescence Analysis In Solution," Applied Spectroscopy, vol. 50, No. 7, pp. 12A-30A, Jul. 1996.

Kodera, Yoh et al., "Pegylation Of Proteins And Bioactive Substances For Medical And Technical Applications," Prog. Polym. Sci., vol. 23, pp. 1233-1271, 1998.

Lane, P. G., "Analysis Of A Continuous-Culture Technique For The Selection Of Mutants Tolerant To Extreme Environmental Stress," Biotechnology and Bioengineering, vol. 65, No. 4, pp. 397-406, Nov. 20, 1999.

Lawrence, J. R. et al., "Optical Sectioning Of Microbial Biofilms," Journal of Bacteriology, vol. 173, No. 20, pp. 6558-6567, Oct. 1991.

Lazar, Iulia M. et al., "Novel Microfabricated Device For Electrokinetically Induced Pressure Flow And Electrospray Ionization Mass Spectrometry," Journal of Chromatography A, vol. 892, pp. 195-201, 2000.

Lee, L. Stanford et al., "Prolonged Circulating Lives Of Single-Chain Fv Proteins Conjugated With Polyethylene Glycol: A Comparison Of Conjugation Chemistries And Compounds," Bioconjugate Chem., vol. 10, pp. 973-981, 1999.

Lessard, Guillaume A. et al., "A Scanning Apertureless Fluorescence Microscope," 8 pages, 1999.

Li, Jianjun et al., "Integration Of Microfabricated Devices To Capillary Electrophoresis-Electrospray Mass Spectrometry Using A Low Dead Volume Connection: Application To Rapid Analyses Of Proteolytic Digests," Analytical Chemistry, vol. 71, No. 15, pp. 3036-3045, Aug. 1, 1999.

Liu, Hanghui et al., "Development Of Multichannel Devices With An Array Of Electrospray Tips For High-Throughput Mass Spectrometry," Analytical Chemistry, vol. 72, No. 14, pp. 3303-3310, Jul. 15, 2000.

Marešová, H. et al., "A Chemostat Culture As A Tool For The Improvement Of A Recombinant E. coli Strain Over-Producing Penicillin G Acylase," Biotechnology And Bioengineering, vol. 75, No. 1, pp. 46-52, Oct. 5, 2001.

Mastrangelo, C. H. et al., "Vacuum-Sealed Silicon Micromachined Incandescent Light Source," IEDM, pp. 503-506, 1989.

Maule, John, "Pulsed-Field Gel Electrophoresis," Molecular Biotechnology, vol. 9, pp. 107-126, 1998.

Menchen, Steve et al., "Flowable Networks As DNA Sequencing Media In Capillary Columns," Electrophoresis, vol. 17, pp. 1451-1459, 1996.

Monod, Jacques, "The Growth Of Bacterial Cultures," Annual Review of Microbiology, vol. III, pp. cover and 371-394, 1949.

New Objective, Inc., "What Is Electrospray," wwww.newobjective.com/electrospray/electrospray.html, 4 pages, 1999.

Nielsen, Jens et al., Bioreaction Engineering Principles, Second Edition, pp. 2 cover pages and 42-45, 2003.

Novick, Aaron et al., "Description Of The Chemostat," Science, vol. 112, pp. 715-716, Dec. 15, 1950.

Novick, Aaron et al., "Experiments With The Chemostat On Spontaneous Mutations Of Bacteria," Proc. N.A.S., vol. 36, pp. 708-719, 1950.

O'Reilly, Marie-Anne J. et al., "The Technique Of Pulsed Field Gel Electrophoresis And Its Impact On Molecular Immunology," Journal of Immunological Methods, vol. 131, pp. 1-13, 1990.

Petty, Jeffrey T. et al., "Characterization Of DNA Size Determination Of Small Fragments By Flow Cytometry," Anal. Chem., vol. 67, pp. 1755-1761, 1995.

Poplawski, M. E. et al., "A Simple Packaging Process For Chemical Sensors," Solid-State Sensor and Actuator Workshop, Hilton Head, South Carolina, pp. 25-28, Jun. 13-16, 1994.

Protana website, "NanoES Products," www.protana.com/products/default.asp, 3 pages, Sep. 19, 2000.

Qu, Mingbo et al., "Toxicity And Biodegradation Of Formaldehyde In Anaerobic Methanogenic Culture," Biotechnology and Bioengineering, vol. 55, No. 5, pp. 727-736, Sep. 5, 1997.

Rotman, Boris, "A Simplified Device For Continuous Growth Of Micoorganisms," Journal of Bacteriology, vol. 70, pp. 485-486, 1955.

Samad, Akhtar et al., "Optical Mapping: A Novel, Single-Molecule Approach To Genomic Analysis," Genome Research, pp. 1-4, 1995.

Schwartz, David C. et al., "Optical Mapping Approaches To Molecular Genomics," Current Opinion in Biotechnology, vol. 8, pp. 70-74, 1997.

Shevchenko, Andrej et al., "Rapid 'de Novo' Peptide Sequencing By A Combination Of Nanoelectrospray, Isotopic Labeling And A Quadrupole/Time-Of-Flight Mass Spectrometer," Rapid Communications in Mass Spectrometry, vol. 11, pp. 1015-1024, 1997.

Shinohara, Jun et al., "A High Pressure-Resistance Micropump Using Active And Normally-Closed Valves," IEEE, pp. 86-91, 2000.

Shuler, Michael L. et al., "Chapter 6—How Cells Grow," Bioprocess Engineering Basic Concepts, Second Edition, pp. 2 cover pages and 155-200, 2002.

Sklar, Larry A. et al., Sample Handling For Kinetics And Molecular Assembly In Flow Cytometry, SPIE, vol. 3256, pp. 144-153, 1998.

Spicer, C. C., "The Theory Of Bacterial Constant Growth Apparatus," Biometrics, pp. 225-230, Jun. 1955.

Stemmer, Willem P. C. et al., "Rapid Evolution Of A Protein in vitro By DNA Shuffling," Nature, vol. 370, pp. 389-390, Aug. 4, 1994.

Sussman, Norman L. et al., "The Predictive Nature Of High-Throughput Toxicity Screening Using A Human Hepatocyte Cell Line," Cell Notes, Issue 3, pp. 7-10, 2002.

Swart, Remco et al., "Recent Progress In Open Tubular Liquid Chromatography," Trends in Analytical Chemistry, vol. 16, No. 6, pp. 332-342, 1997.

Sweet, Richard G., "Chapter 9—Flow Sorters For Biologic Cells," Cytometry and Sorting, John Wiley & Sons, pp. 5 cover pages and 177-189, 1979.

Taylor, Anne M. et al., "Microfluidic Multicompartment Device For Neuroscience Research," Langmuir, vol. 19, pp. 1551-1556, 2003.

Terry, Stephen C. et al., "A Gas Chromatographic Air Analyzer Fabricated On A Silicon Wafer," IEEE Transactions on Electron Devices, vol. ED-26, No. 12, pp. 1880-1886, Dec. 1979.

Todd, Paul et al., "Chapter 12—Cell Electrophoresis," Flow Cytometry and Sorting, John Wiley & Sons, pp. 5 cover pages and 217-229, 1979.

Unger, M., et al., "Single-Molecule Fluorescence Observed With Mercury Lamp Illumination," Biotechniques, vol. 27, No. 5, pp. 1008-1014, Nov. 1999.

Vahey, Paul G. et al., "Development Of A Positive Pressure Driven Micro-Fabricated Liquid Chromatographic Analyzer Through Rapid-Prototyping With Poly(dimethylsiloxane) Optimizing Chromatographic Efficiency With Sub-Nanoliter Injections," Talanta, vol. 51, pp. 1205-1212, 2000.

Veronese, F. M. et al., "Influence Of PEGylation On The Release Of Low And High Molecular-Weight Proteins From PVA Matrices," Journal of Bioactive and Compatible Polymers, vol. 14, pp. 315-330, Jul. 1999.

Veronese, Francesco M., "Peptide And Protein PEGylation: A Review Of Problems And Solutions," Biomaterials, vol. 22, pp. 405-417, 2001.

Volkmuth, W. D. et al., "DNA Electrophoresis in Microlithographic Arrays," Nature, vol. 358, pp. 600-602, Aug. 13, 1992.

Ward, Keith B. et al., "Automatic Prepartion Of Protein Crystals Using Laboratory Robotics And Automated Visual Inspection," Journal of Crystal Growth, vol. 90, pp. 325-339, 1988.

Webster, J. R. et al., "Monolithic Capillary Gel Electrophoresis Stage With On-Chip Detector," IEEE, pp. 491-496, 1996.

Weigl, Bernhard H., "Microfluidics-Based Lab-On-A-Chip Systems," IVD Technology Magazine, 8 pages, Nov./Dec. 2000.

Wiebe, Marilyn G. et al., "Evolution Of A Recombinant (Gucoamylase-Producing) Strain Of Fusarium venenatum A3/5 In Chemostat Culture," Biotechnology and Bioengineering, vol. 73, No. 2, pp. 146-156, Apr. 20, 2001.

Wilm, Matthias, et al., "Femtomole Sequencing Of Proteins From Polyacrylamide Gels By Nano-Electrospray Mass Spectrometry," Nature, vol. 379, pp. 466-469, Feb. 1, 1996.

Wu, Chunhung et al., "Viscosity-Adjustable Block Copolymer For DNA Separation By Capillary Electrophoresis," Electrophoresis, vol. 19, pp. 231-241, 1998.

Xu, Jingdong et al., "Room-Temperature Imprinting Method For Plastic Microchannel Fabrication," Analytical Chemistry, vol. 72, No. 8, pp. 1930-1933, Apr. 15, 2000.

Xue, Qifeng et al., "Integrated Multichannel Microchip Electrospray Ionization Mass Spectrometry: Analysis Of Peptides From On-Chip Tryptic Digestion of Melittin," Rapid Communications In Mass Spectrometry, vol. 11, 1253-1256, 1997.

Xue, Qifeng et al., "Multichannel Microchip Electrospray Mass Spectrometry," Analytical Chemistry, vol. 69, No. 33, pp. 426-430, Feb. 1, 1997.

Yang, T. J. et al., "An Apertureless Near-Field Microscope For Fluorescence Imaging," Applied Physics Letters, vol. 76, No. 3, pp. 378-380, Jan. 17, 2000.

Yokobayashi, Yohei et al., "Evolutionary Design Of Genetic Circuits And Cell-Cell Communications," Advances in Complex Systems, vol. 6, No. 1, pp. 37-45, 2003.

Zalipsky, Samuel, "Chemistry Of Polyethyelene Glycol Conjugates With Biologically Active Molecules," Advanced Drug Delivery Reviews, vol. 16, pp. 157-182, 1995.

Zhang, B. et al., "Microfabricated Devices For Capillary Electrophoresis-Electrospray Mass Spectrometry," Analytical Chemistry, vol. 71, No. 15, pp. 3258-3264, Aug. 1, 1999.

Zdeblick, Mark J. et al., "A Microminiature Electric-To-Fluidic Valve," Tranducers '87, Proceedings of the 4th International Conference on Solid-State Sensors and Actuators, reprinted in Micromechanics and MEMS Classic and Seminal Papers to 1990, pp. 2 cover pages, 437-439, Jun. 1987.

Office Action in pending U.S. Appl. No. 10/819,088, mailed Nov. 6, 2007.

Office Action in pending U.S. Appl. No. 10/819,088, mailed May 3, 2006.

Office Action in pending U.S. Appl. No. 10/819,088, mailed Nov. 18, 2005.

Office Action in pending U.S. Appl. No. 10/818,642, mailed Oct. 31, 2007.

Office Action in pending U.S. Appl. No. 10/818,642, mailed Apr. 6, 2007.

Office Action in pending U.S. Appl. No. 10/818,642, mailed Aug. 11, 2006.

Office Action in pending U.S. Appl. No. 10/837,885, mailed Oct. 17, 2007.

Office Action in pending U.S. Appl. No. 10/837,885, mailed Feb. 7, 2007.

Office Action in pending U.S. Appl. No. 10/837,885, mailed Aug. 14, 2006.

Office Action in pending U.S. Appl. No. 10/876,046, mailed Mar. 9, 2007.

Office Action in pending U.S. Appl. No. 10/876,046, mailed Aug. 10, 2006.

Herbert, D., "Continuous Culture Of Bacteria: Principles And Applications," Chemistry and Industry, p. 381, Mar. 29, 1958.

Lin, Yuehe et al., "Laser Micromachined Isoelectric Focusing Device On Polymer Substrate For Electrospray Mass Spectrometry," SPIE, vol. 3877, pp. 28-35, Sep. 1999.

Schomburg, W. K. et al., "Fabrication Of Polymer Microcomponents With The AMANDA-Process," New Materials and Directions, Eurosensors Xii, pp. 711-714, Sep. 13-16, 1998.

Thorsen, Todd, "Microfluidic Technologies For High-Throughput Screening Applications," California Institute of Technology, 180 pp., Sep. 23, 2002.

Supplementary European Search Report, European Patent Application No. 04758896.7, 3 pages, Jul. 3, 2006.

Office Action, European Patent Application No. 04758896.7, 3 pages, Jul. 16, 2008.

Applicants' Amendment, U.S. Appl. No. 10/819,088, 7 pages, Feb. 21, 2006.

Applicants' Amendment, U.S. Appl. No. 10/819,088, 5 pages, Aug. 3, 2006.

Applicants' Amendment, U.S. Appl. No. 10/819,088, 32 pages, May 6, 2008.

Office Action, U.S. Appl. No. 10/819,088, 6 pages, Feb. 26, 2009.

Applicants' Amendment, U.S. Appl. No. 10/818,642, 9 pages, Jan. 11, 2007.

Applicants' Amendment, U.S. Appl. No. 10/818,642, 11 pages, Oct. 8, 2007.

Applicants' Amendment, U.S. Appl. No. 10/818,642, 36 pages, Apr. 30, 2008.

Applicants' Amendment, U.S. Appl. No. 10/818,642, 5 pages, Jul. 24, 2008.

Applicants' Amendment, U.S. Appl. No. 10/837,885, 9 pages, Nov. 14, 2006.

Applicants' Amendment, U.S. Appl. No. 10/837,885, 9 pages, Aug. 7, 2007.

Applicants' Amendment, U.S. Appl. No. 10/837,885, 17 pages, Apr. 17, 2008.

Applicants' Amendment, U.S. Appl. No. 10/876,046, 9 pages, Dec. 11, 2006.

Applicants' Amendment, U.S. Appl. No. 10/876,046, 8 pages, Sep. 10, 2007.

Office Action, U.S. Appl. No. 10/876,046, 13 pages, Nov. 12, 2008.

Office Action, U.S. Appl. No. 11/929,436, 9 pages, Feb. 2, 2009.

* cited by examiner

Green Only
Fig. 18a

Red and Green

Fig 18b

THERMAL REACTION DEVICE AND METHOD FOR USING THE SAME

PRIORITY CLAIM

This non-provisional patent application is a continuation-in-part application claiming priority to U.S. non-provisional continuation-in-part patent application Ser. No. 10/876,046, which claims priority to U.S. non-provisional continuation-in-part patent application Ser. No. 10/837,835, filed on May 2, 2004, which claims priority to U.S. non-provisional application Ser. No. 10/818,642, filed on Apr. 5, 2004, which claims priority under 35 U.S.C. § 119(e) to U.S. provisional patent application Ser. No. 60/460,634, filed on Apr. 3, 2003, by Unger et al., all of which are incorporated by reference in their entirety for all purposes and the specific purposes describe therein and herein.

CROSS-REFERENCE TO RELATED APPLICATIONS

This application relates to U.S. non-provisional application 11/043,895, filed on Feb. 14, 2005, which is incorporated by reference in its entirety for all purposes.

BACKGROUND

Recently, there have been concerted efforts to develop and manufacture microfluidic systems to perform various chemical and biochemical analyses and syntheses, both for preparative and analytical applications. The goal to make such devices arises because of the significant benefits that can be realized from miniaturization with respect to analyses and syntheses conducted on a macro scale. Such benefits include a substantial reduction in time, cost and the space requirements for the devices utilized to conduct the analysis or synthesis. Additionally, microfluidic devices have the potential to be adapted for use with automated systems, thereby providing the additional benefits of further cost reductions and decreased operator errors because of the reduction in human involvement. Microfluidic devices have been proposed for use in a variety of applications, including, for instance, capillary electrophoresis, gas chromatography and cell separations.

However, realization of these benefits has often been thwarted because of various complications associated with the microfluidic devices that have thus far been manufactured. For instance, many of the current microfluidic devices are manufactured from silica-based substrates; these materials are difficult and complicated to machine and devices made from such materials are fragile. Furthermore, transport of fluid through many existing microfluidic devices requires regulation of complicated electrical fields to transport fluids in a controlled fashion through the device.

Thus, in view of the foregoing benefits that can be achieved with microfluidic devices but the current limitations of existing devices, there remains a need for microfluidic devices designed for use in conducting a variety of chemical and biochemical analyses. Because of its importance in modern biochemistry, there is a particular need for devices that can be utilized to conduct a variety of nucleic acid amplification reactions, while having sufficient versatility for use in other types of analyses as well.

Devices with the ability to conduct nucleic acid amplifications would have diverse utilities. For example, such devices could be used as an analytical tool to determine whether a particular target nucleic acid of interest is present or absent in a sample. Thus, the devices could be utilized to test for the presence of particular pathogens (e.g., viruses, bacteria or fungi), and for identification purposes (e.g., paternity and forensic applications). Such devices could also be utilized to detect or characterize specific nucleic acids previously correlated with particular diseases or genetic disorders. When used as analytical tools, the devices could also be utilized to conduct genotyping analyses and gene expression analyses (e.g., differential gene expression studies). Alternatively, the devices can be used in a preparative fashion to amplify sufficient nucleic acid for further analysis such as sequencing of amplified product, cell-typing, DNA fingerprinting and the like. Amplified products can also be used in various genetic engineering applications, such as insertion into a vector that can then be used to transform cells for the production of a desired protein product.

SUMMARY

A variety of devices and methods for conducting microfluidic analyses are provided herein, including devices that can be utilized to conduct thermal cycling reactions such as nucleic acid amplification reactions. The devices differ from conventional microfluidic devices in that they include elastomeric components; in some instances, much or all of the device is composed of elastomeric material.

Certain devices are designed to conduct thermal cycling reactions (e.g., PCR) with devices that include one or more elastomeric valves to regulate solution flow through the device. Thus, methods for conducting amplification reactions with devices of this design are also provided.

Some of the devices include blind flow channels which include a region that functions as a reaction site. Certain such devices include a flow channel formed within an elastomeric material, and a plurality of blind flow channels in fluid communication with the flow channel, with a region of each blind flow channel defining a reaction site. The devices can also include one or more control channels overlaying and intersecting each of the blind flow channels, wherein an elastomeric membrane separates the one or more control channels from the blind flow channels at each intersection. The elastomeric membrane in such devices is disposed to be deflected into or withdrawn from the blind flow channel in response to an actuation force. The devices can optionally further include a plurality of guard channels formed within the elastomeric material and overlaying the flow channel and/or one or more of the reaction sites. The guard channels are designed to have fluid flow therethrough to reduce evaporation from the flow channels and reaction sites of the device. Additionally, the devices can optionally include one or more reagents deposited within each of the reaction sites.

In certain devices, the flow channel is one of a plurality of flow channels, each of the flow channels in fluid communication with multiple blind flow channels which branch therefrom. Of devices of this design, in some instances the plurality of flow channels are interconnected with one another such that fluid can be introduced into each of the reaction sites via a single inlet. In other devices, however, the plurality of flow channels are isolated from each other such that fluid introduced into one flow channel cannot flow to another flow channel, and each flow channel comprises an inlet at one or both ends into which fluid can be introduced.

Other devices include an array of reaction sites having a density of at least 50 sites/cm$^2$, with the reaction sites typically formed within an elastomeric material. Other devices have even higher densities such as at least 250, 500 or 1000 sites/cm$^2$, for example.

Still other device include a reaction site formed within an elastomeric substrate, at which a reagent for conducting a reaction is non-covalently immobilized. The reagent can be one or more reagents for conducting essentially any type of reaction. The reagent in some devices includes one reagents for conducting a nucleic acid amplification reaction. Thus, in some devices the reagent comprises a primer, polymerase and one or more nucleotides. In other devices, the reagent is a nucleic acid template.

A variety of matrix or array-based devices are also provided. Certain of these devices include: (i) a first plurality of flow channels formed in an elastomeric substrate, (ii) a second plurality of flow channels formed in the elastomeric substrate that intersect the first plurality of flow channels to define an array of reaction sites, (iii) a plurality of isolation valves disposed within the first and second plurality of flow channels that can be actuated to isolate solution within each of the reaction sites from solution at other reaction sites, and (iv) a plurality of guard channels overlaying one or more of the flow channels and/or one or more of the reaction sites to prevent evaporation of solution therefrom.

The foregoing devices can be utilized to conduct a number of different types of reactions, including those involving temperature regulation (e.g., thermocycling of nucleic acid analyses). Methods conducted with certain blind channel type devices involve providing a microfluidic device that comprises a flow channel formed within an elastomeric material; and a plurality of blind flow channels in fluid communication with the flow channel, with an end region of each blind flow channel defining a reaction site. At least one reagent is introduced into each of the reaction sites, and then a reaction is detected at one or more of the reaction sites. The method can optionally include heating the at least one reagent within the reaction site. Thus, for example, a method can involve introducing the components for a nucleic acid amplification reaction and then thermocycling the components to form amplified product.

Other methods involve providing a microfluidic device comprising one or more reaction sites, each reaction site comprising a first reagent for conducting an analysis that is non-covalently deposited on an elastomeric substrate. A second reagent is then introduced into the one or more reaction sites, whereby the first and second reagents mix to form a reaction mixture. A reaction between the first and second reagents at one or more of the reaction sites is subsequently detected.

Still other methods involve providing a microfluidic device comprising an array of reaction sites formed within a substrate and having a density of at least 50 sites/cm$^2$. At least one reagent is introduced into each of the reaction sites. A reaction at one or more of the reaction sites is then detected.

Yet other methods involve providing a microfluidic device comprising at least one reaction site which is formed within an elastomeric substrate and a plurality of guard channels also formed within the elastomeric substrate. At least one reagent is introduced into each of the reaction sites and then heated within the reaction sites. A fluid is flowed through the guard channels before or during heating to reduce evaporation from the at least one reaction site. A reaction within the at least one reaction site is subsequently detected.

Additional devices designed to reduce evaporation of fluid from the device are also provided. In general, such devices comprise a cavity that is part of a microfluidic network formed in an elastomeric substrate; and a plurality of guard channels overlaying the cavity and separated from the cavity by an elastomeric membrane. The guard channel in such devices is sized (i) to allow solution flow therethrough, and (ii) such that there is not a substantial reduction in solution flow in, out or through the cavity due to deflection of the membrane(s) upon application of an actuation force to the guard channels. Other such devices include (i) one or more flow channels and/or one or more reaction sites; and (ii) a plurality of guard channels overlaying the microfluidic system and separated therefrom by elastomer, wherein the spacing between guard channels is between 1 µm to 1 mm. In other devices the spacing is between 5 µm and 500 µm, in other devices between 10 µm and 100 µm, and in still other devices between 40 µm and 75 µm.

In other embodiments of the invention provide for a microfluidic device have one or more sample channels having a plurality of valves in communication therewith, wherein each sample channel, when filled with a sample, can be partitioned into sub-samples for conducting analysis, such as amplification, for example, but not limited to PCR, including TAQMAN™, and endpoint PCR, and isothermal amplification techniques, such as INVADER™. Such microfluidic devices may have some sample channels devoted to partition and analyze known control samples, while other sample channels may be used to partition and analyze one or more test samples. The arrangement of the separate sample channels may be interdigitated or laid out as plots among the device surface, the latter being preferred for optimizing conditions for conducting analysis on a routine basis. One advantage of partitioning a sample is to reduce the apparent concentration of a high background of wild type sample containing a low, such as one, two, three, four, five, or six orders of magnitude lower concentration of a mutant sample than the wild type sample. For example, when analyzing a sample containing a high concentration of wild-type DNA that contains a very small, several orders of magnitude, such as $10^{-3}$ less copies than the wild type. By partitioning the sample many fold, such as by 100, 1,000, 10,000, 100,000, or 1,000,000 fold, the ratio in each partition between wild type and mutant DNA is changed from the original ratio such that the likelihood of background PCR product that would be produced relative the amount of PCR product produced from the target mutant is minimized to yield a valid signal indicating the presence of the mutant DNA target in the particular partitioned chamber. There may also be benefits afforded by conducting the reaction in very small volumes that are obtainable in certain embodiments of the present invention, in that by conducting the reaction in a small volume raises the concentration of target to the volume of the total reaction.

In another embodiment, the invention provides a method for analyzing the presence of a specific gene, for example but not limited to an oncogene point mutation in a patient suspected of having a tumor if the tumor releases genetic material into the body, in particular, the blood stream, even though other non-oncogenic genetic material may be present in the blood stream in great excess, including one, two, three, four, five, and six orders of magnitude greater excess than the target oncogenic target genetic material. For example, in the K-ras point mutation at codon 12 occurs in about 70 to 95% of the cells of this cancer, wherein some or all of the cells may release genetic material containing the K-ras point mutation at codon 12 which can be detected by the methods described herein using the devices herein. In yet another embodiment, a sample may contain whole cells that when analyzed, for example but not limited to, by PCR, the cells lyse and make their genetic material available for amplification. Other oncogenic point mutations and genetic diseases that produce amplifiable genetic material in low quantities relative to the background genetic material normally present Compositions for conducting nucleic acid analyses in reaction sites of certain microfluidic devices are also provided. Certain such compositions include one or more of the following: an agent that blocks protein binding sites on an elastomeric material and a detergent. The blocking agent is typically selected from the group consisting of a protein (e.g., gelatin or albumin, such as bovine serum albumin (BSA)). The detergent can be SDS or Triton, for example

BRIEF DESCRIPTION OF THE DRAWINGS

FIG. 3C is an enlarged view of a region of the device shown in FIG. 3B, and illustrates the orientation of the guard flow channels in this particular design.

FIGS. 18a and 18b depict images of a partitioning microfluidic devices after a thermocycling reaction was performed. FIG. 18a depicts a two color image, and FIG. 18b depicts the remaining signal after subtraction of the control red signal.

DETAILED DESCRIPTION

I. Definitions

Figure 1A:
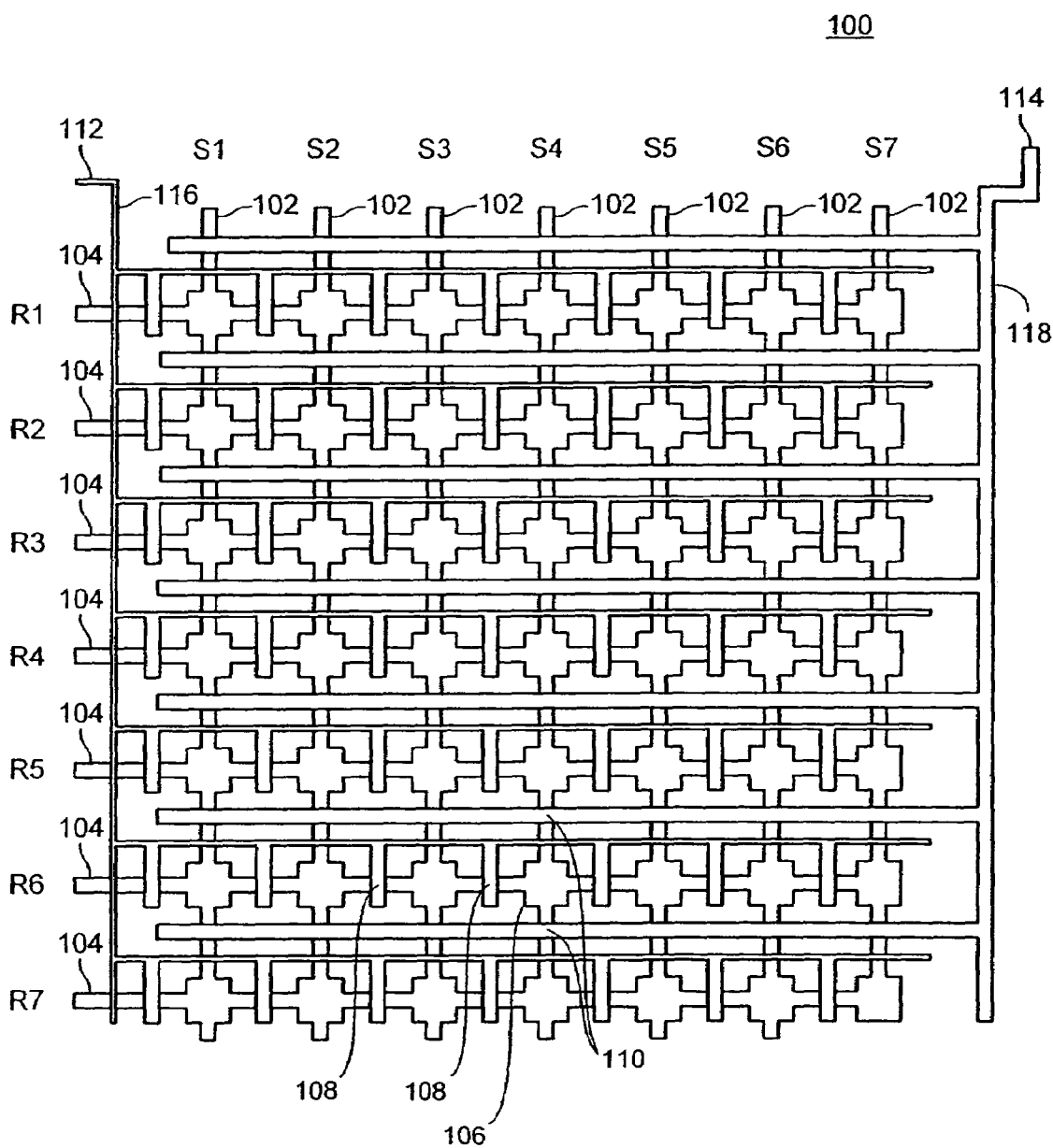
FIG. 1A is a schematic representation of an exemplary device with a matrix design of intersecting vertical and horizontal flow channels.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

A "flow channel" refers generally to a flow path through which a solution can flow.

The term "valve" unless otherwise indicted refers to a configuration in which a flow channel and a control channel intersect and are separated by an elastomeric membrane that can be deflected into or retracted from the flow channel in response to an actuation force.

A "blind channel" or a "dead-end channel" refers to a flow channel which has an entrance but not a separate exit. Accordingly, solution flow in and out of the blind channel occurs at the same location. The process of filling one or more blind channels is sometimes simply referred to as "blind fill."

An "isolated reaction site" generally refers to a reaction site that is not in fluid communication with other reactions sites present on the device. When used with respect to a blind channel, the isolated reaction site is the region at the end of the blind channel that can be blocked off by a valve associated with the blind channel.

A "via" refers to a channel formed in an elastomeric device to provide fluid access between an external port of the device and one or more flow channels. Thus, a via can serve as a sample input or output, for example.

The term "elastomer" and "elastomeric" has its general meaning as used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 1 Pa-1 TPa, in other instances between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application.

Some of the microfluidic devices described herein are fabricated from an elastomeric polymer such as GE RTV 615 (formulation), a vinyl-silane crosslinked (type) silicone elastomer (family). However, the present microfluidic systems are not limited to this one formulation, type or even this family of polymer; rather, nearly any elastomeric polymer is suitable. Given the tremendous diversity of polymer chemistries, precursors, synthetic methods, reaction conditions, and potential additives, there are a large number of possible elastomer systems that can be used to make monolithic elastomeric microvalves and pumps. The choice of materials typically depends upon the particular material properties (e.g., solvent resistance, stiffness, gas permeability, and/or temperature stability) required for the application being conducted. Additional details regarding the type of elastomeric materials that can be used in the manufacture of the components of the microfluidic devices disclosed herein are set forth in Unger et al. (2000) Science 288:113-116, and PCT Publications WO 02/43615, and WO 01/01025, which are incorporated herein by reference in their entirety for all purposes.

The terms "nucleic acid," "polynucleotide," and "oligonucleotide" are used herein to include a polymeric form of nucleotides of any length, including, but not limited to, ribonucleotides or deoxyribonucleotides. There is no intended distinction in length between these terms. Further, these terms refer only to the primary structure of the molecule. Thus, in certain embodiments these terms can include triple-, double- and single-stranded DNA, as well as triple-, double- and single-stranded RNA. They also include modifications, such as by methylation and/or by capping, and unmodified forms of the polynucleotide. More particularly, the terms "nucleic acid," "polynucleotide," and "oligonucleotide," include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. The label attached to the probe can include any of a variety of different labels known in the art that can be detected by chemical or physical means, for example. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Probes can vary significantly in size. Some probes are relatively short. Generally, probes are at least 7 to 15 nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

A "primer" is a single-stranded polynucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically is at least 7 nucleotides long and, more typically range from 10 to 30 nucleotides in length. Other primers can be somewhat longer such as 30 to 50 nucleotides long. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes. The term "primer pair" means a set of primers including a 5' "upstream primer" that hybridizes with the complement of the 5' end of the DNA sequence to be amplified and a 3' "downstream primer" that hybridizes with the 3' end of the sequence to be amplified.

A primer that is "perfectly complementary" has a sequence fully complementary across the entire length of the primer and has no mismatches. The primer is typically perfectly complementary to a portion (subsequence) of a target sequence. A "mismatch" refers to a site at which the nucleotide in the primer and the nucleotide in the target nucleic acid with which it is aligned are not complementary. The term "substantially complementary" when used in reference to a primer means that a primer is not perfectly complementary to its target sequence; instead, the primer is only sufficiently complementary to hybridize selectively to its respective strand at the desired primer-binding site.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14-25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

The term "label" refers to a molecule or an aspect of a molecule that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, enzymes linked to nucleic acid probes and enzyme substrates. The term "detectably labeled" means that an agent has been conjugated with a label or that an agent has some inherent characteristic (e.g., size, shape or color) that allows it to be detected without having to be conjugated to a separate label.

A "polymorphic marker" or "polymorphic site" is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

A "reagent" refers broadly to any agent used in a reaction. A reagent can include a single agent which itself can be monitored (e.g., a substance that is monitored as it is heated) or a mixture of two or more agents. A reagent may be living (e.g., a cell) or non-living. Exemplary reagents for a nucleic acid amplification reaction include, but are not limited to, buffer, metal ions, polymerase, primers, template nucleic acid, nucleotides, labels, dyes, nucleases and the like. Reagents for enzyme reactions include, for example, substrates, cofactors, coupling enzymes, buffer, metal ions, inhibitors and activators. Reagents for cell-based reactions include, but are not limited to, cells, cell specific dyes and ligands (e.g., agonists and antagonists) that bind to cellular receptors.

A "ligand" is any molecule for which there exists another molecule (i.e., an "antiligand") that specifically or non-specifically binds to the ligand, owing to recognition of some portion of the ligand by the antiligand.

II. Overview

A number of different microfluidic devices (also sometimes referred to as chips) having unique flow channel architectures are provided herein, as well as methods for using such devices to conduct a variety of high throughput analyses. The devices are designed for use in analyses requiring temperature control, especially analyses involving thermocycling (e.g., nucleic acid amplification reactions). The microfluidic devices incorporate certain design features that: give the devices a significantly smaller footprint than many conventional microfluidic devices, enable the devices to be readily integrated with other instrumentation and provide for automated analysis.

Some of the microfluidic devices utilize a design typically referred to herein as "blind channel" or "blind fill" are characterized in part by having a plurality of blind channels, which, as indicated in the definition section, are flow channels having a dead end or isolated end such that solution can only enter and exit the blind channel at one end (i.e., there is not a separate inlet and outlet for the blind channel). These devices require only a single valve for each blind channel to isolate a region of the blind channel to form an isolated reaction site. During manufacture of this type of device, one or more reagents for conducting an analysis are deposited at the reaction sites, thereby resulting in a significant reduction in the number of input and outputs. Additionally, the blind channels are connected to an interconnected network of channels such that all the reaction sites can be filled from a single, or limited number, of sample inputs. Because of the reduction in complexity in inputs and outputs and the use of only a single valve to isolate each reaction site, the space available for reaction sites is increased. Thus, the features of these devices means that each device can include a large number of reaction sites (e.g., up to tens of thousands) and can achieve high reaction site densities (e.g., over 1,000-4,000 reaction sites/cm$^2$). Individually and collectively, these features also directly translate into a significant reduction in the size of these devices compared to traditional microfluidic devices.

Other microfluidic devices that are disclosed herein utilize a matrix design. In general, microfluidic devices of this type utilize a plurality of intersecting horizontal and vertical flow channels to define an array of reaction sites at the points of intersection. Thus, devices of this design also have an array or reaction sites; however, there is a larger number of sample inputs and corresponding outputs to accommodate the larger number of samples with this design. A valve system referred to as a switchable flow array architecture enables solution be flowed selectively through just the horizontal or flow channels, thus allowing for switchable isolation of various flow channels in the matrix. Hence, whereas the blind channel devices are designed to conduct a large number of analyses under different conditions with a limited number of samples, the matrix devices are constructed to analyze a large number of sample under a limited number of conditions. Still other devices are hybrids of these two general design types.

The microfluidic devices that are described are further characterized in part by utilizing various components such as flow channels, control channels, valves and/or pumps from elastomeric materials. In some instances, essentially the entire device is made of elastomeric material. Consequently, such devices differ significantly in form and function from the majority of conventional microfluidic devices that are formed from silicon-based material.

The design of the devices enables them to be utilized in combination with a number of different heating systems. Thus, the devices are useful in conducting diverse analyses that require temperature control. Additionally, those microfluidic devices for use in heating applications can incorporate a further design feature to minimize evaporation of sample from the reaction sites. Devices of this type in general include a number of guard channels formed within the elastomeric device through which water can be flowed to increase the water vapor pressure within the elastomeric material from which the device is formed, thereby reducing evaporation of sample from the reaction sites.

In another embodiment, a temperature cycling device may be used to control the temperature of the microfluidic devices. Preferably, the microfluidic device would be adapted to make thermal contact with the microfluidic device. Where the microfluidic device is supported by a substrate material, such as a glass slide or the bottom of a carrier plate, such as a plastic carrier, a window may be formed in a region of the carrier or slide such that the microfluidic device, preferably a device having an elastomeric block, may directly contact the heating/cooling block of the temperature cycling device. In a preferred embodiment, the heating/cooling block has grooves therein in communication with a vacuum source for applying a suction force to the microfluidic device, preferably the portion wherein the reactions are taking place. Alternatively, a rigid thermally conductive plate may be bonded to the microfluidic device that then mates with the heating and cooling block for efficient thermal conduction resulting.

The array format of certain of the devices means the devices can achieve high throughput. Collectively, the high throughput and temperature control capabilities make the devices useful for performing large numbers of nucleic acid amplifications (e.g., polymerase chain reaction—PCR). Such reactions will be discussed at length herein as illustrative of the utility of the devices, especially of their use in any reaction requiring temperature control. However, it should be understood that the devices are not limited to these particular applications. The devices can be utilized in a wide variety of other types of analyses or reactions. Examples include analyses of protein-ligand interactions and interactions between cells and various compounds. Further examples are provided infra.

III. General Structure of Microfluidic Devices

A. Pumps and Valves

The microfluidic devices disclosed herein are typically constructed at least in part from elastomeric materials and constructed by single and multilayer soft lithography (MSL) techniques and/or sacrificial-layer encapsulation methods (see, e.g., Unger et al. (2000) Science 288:113-116, and PCT Publication WO 01/01025, both of which are incorporated by reference herein in their entirety for all purposes). Utilizing such methods, microfluidic devices can be designed in which solution flow through flow channels of the device is controlled, at least in part, with one or more control channels that are separated from the flow channel by an elastomeric membrane or segment. This membrane or segment can be deflected into or retracted from the flow channel with which a control channel is associated by applying an actuation force to the control channels. By controlling the degree to which the membrane is deflected into or retracted out from the flow channel, solution flow can be slowed or entirely blocked through the flow channel. Using combinations of control and flow channels of this type, one can prepare a variety of different types of valves and pumps for regulating solution flow as described in extensive detail in Unger et al. (2000) Science 288:113-116, and PCT Publication WO/02/43615 and WO 01/01025.

The devices provided herein incorporate such pumps and valves to isolate selectively a reaction site at which reagents are allowed to react. The reaction sites can be located at any of a number of different locations within the device. For example, in some matrix-type devices, the reaction site is located at the intersection of a set of flow channels. In blind channel devices, the reaction site is located at the end of the blind channel.

If the device is to be utilized in temperature control reactions (e.g., thermocycling reactions), then, as described in greater detail infra, the elastomeric device is typically fixed to a support (e.g., a glass slide). The resulting structure can then be placed on a temperature control plate, for example, to control the temperature at the various reaction sites. In the case of thermocycling reactions, the device can be placed on any of a number of thermocycling plates.

Because the devices are made of elastomeric materials that are relatively optically transparent, reactions can be readily monitored using a variety of different detection systems at essentially any location on the microfluidic device. Most typically, however, detection occurs at the reaction site itself (e.g., within a region that includes an intersection of flow channels or at the blind end of a flow channel). The fact that the device is manufactured from substantially transparent materials also means that certain detection systems can be utilized with the current devices that are not usable with traditional silicon-based microfluidic devices. Detection can be achieved using detectors that are incorporated into the device or that are separate from the device but aligned with the region of the device to be detected.

B. Guard Channels

To reduce evaporation of sample and reagents from the elastomeric microfluidic devices that are provided herein, a plurality of guard channels can be formed in the devices. The guard channels are similar to the control channels in that typically they are formed in a layer of elastomer that overlays the flow channels and/or reaction site. Hence, like control channels, the guard channels are separated from the underlying flow channels and/or reaction sites by a membrane or segment of elastomeric material. Unlike control channels, however, the guard channels are considerably smaller in cross-sectional area. In general, a membrane with smaller area will deflect less than a membrane with larger area under the same applied pressure. The guard channels are designed to be pressurized to allow solution (typically water) to be flowed into the guard channel. Water vapor originating from the guard channel can diffuse into the pores of the elastomer adjacent a flow channel or reaction site, thus increasing the water vapor concentration adjacent the flow channel or reaction site and reducing evaporation of solution therefrom.

In general, the guard channels are sufficiently small such that when pressurized the membrane that separates the guard channel from the underlying flow channel or reaction site does not substantially restrict solution flow in, out, or through the flow channel or reaction site which the guard channel overlays. When used in this context, the term "substantially restrict" or other similar terms means that solution flow is not reduced in, out or through the flow channel or reaction site by more than 40%, typically less than 30%, usually less than 20%, and in some instances less than 10%, as compared to solution flow in, to or through the flow channel or reaction site under the same conditions, when the guard channel is not pressurized to achieve solution flow therethrough. Usually this means that the guard channels have a cross-sectional area of between 100 µm$^2$ and 50,000 µm$^2$, or any integral or non-integral cross-sectional area therebetween. Thus, for example, in some instances, the cross-sectional area is less than 50,000 µm, in other instances less than 10,000 µm$^2$, in still other instances less than 10,00 µm$^2$, and in yet other instances less than 100 µm. The guard channels can have any of a variety of shapes including, but not limited to, circular, elliptical, square, rectangular, hexagonal and octahedral shapes.

The guard channels are designed to reduce the evaporation of sample and reagents from the device during the time and under the conditions that it takes to conduct a thermocycling reaction to less than 50%, in other instance less than 45%, 40%, 35%, 30%, 25%, 20%, 15%, 10%, 5% or 1%. Thus, for example, a typical PCR reaction involving 40 cycles can be conducted within 120 minutes. The guard channel system is designed to reduce evaporation during approximately this time frame to the foregoing set of limits. To achieve this level of evaporation reduction, the guard channels are typically present at a density of at least 10 lines/cm$^2$ to 1000 lines/cm$^2$, or any integral density level therebetween. More specifically, the guard channels are generally at least 25 lines/cm$^2$, in other instances at least 50 lines/cm$^2$, in still other instances at least 100 lines/cm$^2$, and in yet other instances at least 500 lines/cm$^2$. To achieve this level of evaporation reduction, the guard channels are typically present at a spacing between 1 mm to 1 µm as measured from the outer edge of one line to the nearest outer edge of adjacent line, or any integral density level therebetween. More specifically, the guard channels are generally spaced between 500 µm to 5 µm, in other instances between 100 µm to 10 µm, in still other instances between 75 µm to 40 µm. Thus, the spacing is typically at least 1 µm, but is less than 1 mm, in other instances less than 500 µm, in still other instances less than 400 µm, in yet other instances less than 300 µm, in other instances less than 200 µm, and in still other instances less than 100 µm, 50 µm or 25 µm.

The guard channels can be formed as a separate network of channels or can be smaller channels that branch off of the control channels. The guard channels can extend across the device or only a particular region or regions of the device. Typically, the guard channels are placed adjacent and over flow channels and reaction sites as these are the primary locations at which evaporation is the primary concern. Exemplary locations of guard channels on certain matrix devices are illustrated in FIG. 1C, and on certain blind channel devices in FIGS. 3B and 3C, and discussed in greater detail infra.

The solution flowed through the guard channel includes any substance that can reduce evaporation of water. The substance can be one that increases the water vapor concentration adjacent a flow line and/or reaction site, or one that while not increasing the water vapor concentration nonetheless blocks evaporation of water from the flow line and/or reaction site (blocking agent). Thus, one option is to utilize essentially any aqueous solution in which case suitable solutions include, but are not limited to, water and buffered solution (e.g., TaqMan buffer solution, and phosphate buffered saline). Suitable blocking agents include, for example, mineral oil.

Guard channels are typically formed in the elastomer utilizing the MSL techniques and/or sacrificial-layer encapsulation methods cited above.

The following sections describe in greater detail a number of specific configurations that can be utilized to conduct a variety of analyses, including analyses requiring temperature control (e.g., nucleic acid amplification reactions). It should be understood, however, that these configurations are exemplary and that modifications of these systems will be apparent to those skilled in the art.

IV. Matrix Design

A. General

Devices utilizing the matrix design generally have a plurality of vertical and horizontal flow channel that intersect to form an array of junctions. Because a different sample and reagent (or set of reagents) can be introduced into each of the flow channels, a large number of samples can be tested against a relatively large number of reaction conditions in a high throughput format. Thus, for example, if a different sample is introduced into each of M different vertical flow channels and a different reagent (or set of reagents) is introduced into each of N horizontal flow channels, then M×N different reactions can be conducted at the same time. Typically, matrix devices include valves that allow for switchable isolation of the vertical and horizontal flow channels. Said differently, the valves are positioned to allow selective flow just through the vertical flow channels or just through the horizontal flow channels. Because devices of this type allow flexibility with respect to the selection of the type and number of samples, as well as the number and type of reagents, these devices are well-suited for conducting analyses in which one wants to screen a large number of samples against a relatively large number of reaction conditions. The matrix devices can optionally incorporate guard channels to help prevent evaporation of sample and reactants.

Figure 21:
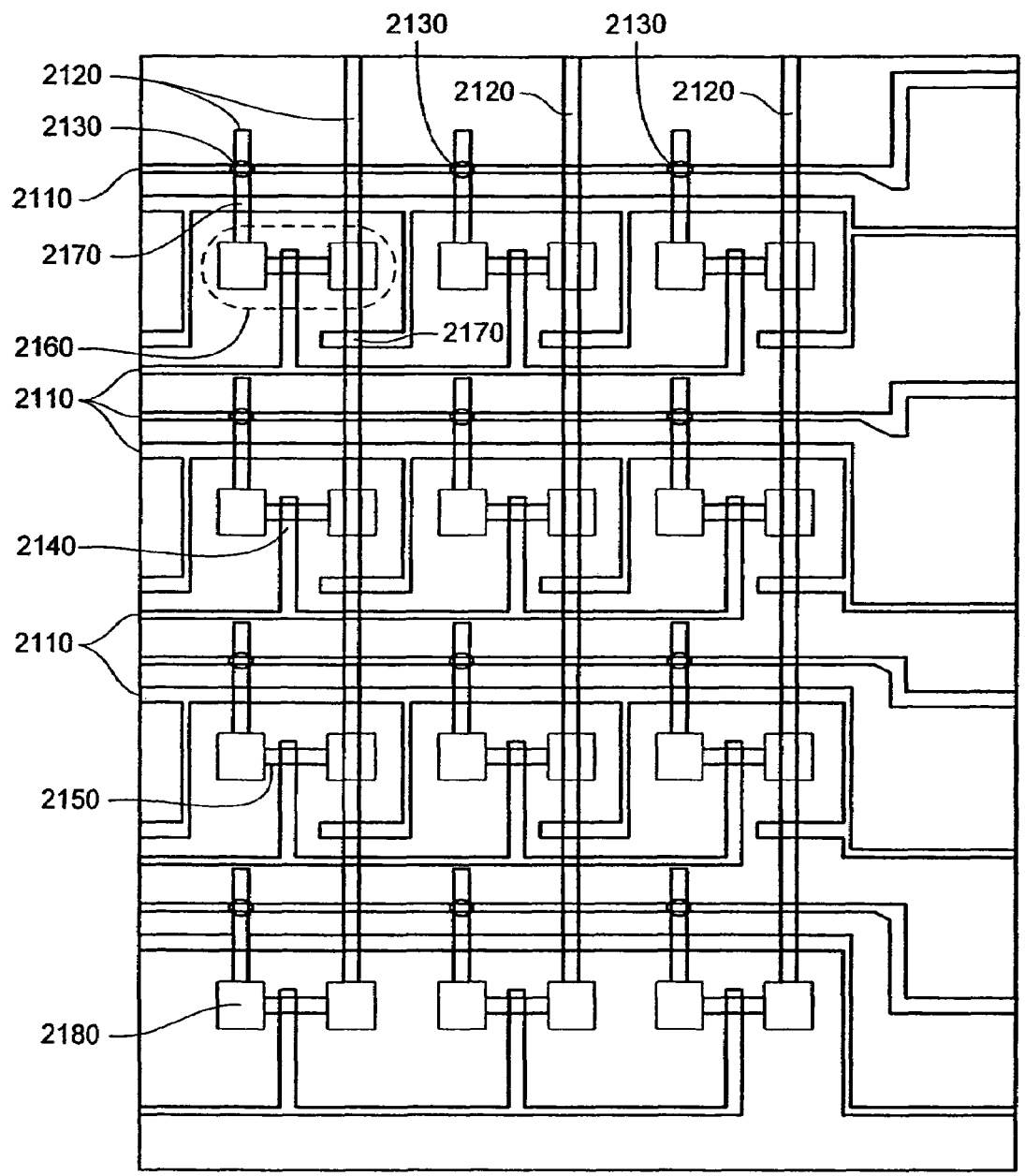
FIG. 21 depicts an exemplary matrix microfluidic device plan view.

The invention provides for high-density matrix designs that utilize fluid communication vias between layers of the microfluidic device to weave control lines and fluid lines through the device. For example, by having a fluid line in each layer of a two layer elastomeric block, higher density reaction cell arrangements are possible. FIG. 21 depicts an exemplary matrix design wherein a first elastomeric layer (1st layer) and a second elastomeric layer (2d layer) each having fluid channels formed therein. For example, a reagent fluid channel in the first layer is connected to a reagent fluid channel in the second layer through a via, while the second layer also has sample channels therein, the sample channels and the reagent channels terminating in sample and reagent chambers, respectively. The sample and reagent chambers are in fluid communication with each other through an interface channel that has an interface valve associated therewith to control fluid communication between each of the chambers of a reaction cell. In use, the interface is first closed, then reagent is introduced into the reagent channel from the reagent inlet and sample is introduced into the sample channel through the sample inlet, containment valves are then closed to isolate each reaction cell from other reaction cells. Once the reaction cells are isolated, the interface valve is opened to cause the sample chamber and the reagent chamber to be in fluid communication with each other so that a desired reaction may take place.

Accordingly, a preferred aspect of the invention provides for a microfluidic device for reacting M number of different samples with N number of different reagents comprising: a plurality of reaction cells, each reaction cell comprising a sample chamber and a reagent chamber, the sample chamber and the reagent chamber being in fluid communication through an interface channel having an interface valve associated therewith for controlling fluid communication between the sample chamber and the reagent chamber; a plurality of sample inlets each in fluid communication with the sample chambers; a plurality of reagent inlets each in fluid communication with the reagent chambers; wherein one of the sample inlets or reagent inlets is in fluid communication with one of the sample chambers or one of the reagent chambers, respectively, through a via. Certain embodiments include having the reaction cells be formed within an elastomeric block formed from a plurality of layers bonded together and the interface valve is deflectable membrane; having the sample inlets be in communication with the sample chamber through a sample channel and the reagent inlet is in fluid communication with the reagent chamber through a reagent channel, a portion of the sample channel and a portion of the reagent channel being oriented about parallel to each other and each having a containment valve associated therewith for controlling fluid communication therethrough; having the valve associated with the sample channel and the valve associated with the reagent channel are in operable communication with each other through a common containment control channel; having the containment common control channel located along a line about normal to one of the sample channel or the reagent channel Another aspect of the invention provides for a method for making a feature in an elastomeric block comprising the steps of: providing a first elastomeric layer; applying a photoresist layer upon a surface of the first elastomeric layer; applying a light pattern to the photoresist layer to form a pattern of reacted photoresist material; removing unreacted photoresist material leaving the pattern of reacted photoresist upon the surface of the first elastomeric layer; applying an etching reagent to the first elastomeric surface to etch the surface of the first elastomeric layer not covered by the pattern of reacted photoresist material thereby removing regions of the first elastomeric layer not covered by the pattern of reacted photoresist and leaving a pattern of the elastomeric layer corresponding to the pattern of reacted photoresist material. In certain preferred embodiments of the method include having a step of removing the pattern of reacted photoresist material; having the removing is caused by applying an adhesive tape to the surface of the elastomeric layer and the pattern of reacted photoresist material, then separating the adhesive tape from the elastomeric layer while some or all of the pattern of reacted photoresist material is removed from the surface of the elastomeric layer; having the photo resist be SU8; having the etching reagent comprises tetrabutylammoniumfluoride-trihydrate; having the feature be a via; having the elastomeric block comprise a plurality of elastomeric layers bonded together, wherein two or more elastomeric layers have recesses formed therein and one recess of one elastomeric layer is in communication with a recess of another elastomeric layer through the via.

The microfluidic devices of the present invention may be further integrated into the carrier devices described in copending and co-owned U.S. patent application Ser. No. 60/557,715 by Unger filed on Mar. 29, 2004, which is herein incorporated for all purposes. The carrier of Unger provides on-board continuous fluid pressure to maintain valve closure away from a source of fluid pressure, e.g., house air pressure. Unger further provides for an automated system for charging and actuating the valves of the present invention as described therein.

B. Exemplar Designs and Uses

FIG. 1A provides an illustration of one exemplary matrix device. This device 100 comprises seven vertical flow channels 102 and seven horizontal flow channels 104 that intersect to form an array of 49 different intersections or reaction sites 106. This particular device thus enables seven samples to be reacted with seven different reagents or sets of reagents. Column valves 110 that regulate solution flow in the vertical direction can be controlled by control channels 118 that can all be actuated at a single inlet 114.

Similarly, row valves 108 regulate solution flow in the horizontal direction; these are controlled by control channels 116 that are actuated by a single control inlet 112. As shown in FIG. 1A, the control channels 116 that regulate the row valves 108 vary in width depending upon location. When a control channel 116 crosses a vertical flow channel 102, the control channel 116 is sufficiently narrow that when it is actuated it does not deflect into the vertical flow channel 102 to reduce substantially solution flow therethrough. However, the width of the control channel 116 is increased when it overlays one of the horizontal flow channels 104; this makes the membrane of the control channel sufficiently large to block solution flow through the horizontal flow channel 104.

In operation, reagents R1-R7 are introduced into their respective horizontal flow channels 104 and samples S1-S7 are injected into their respective vertical flow channels 102. The reagents in each horizontal flow channel 104 thus mix with the samples in each of the vertical flow channels 102 at the intersections 106, which in this particular device are in the shape of a well or chamber. Thus, in the specific case of a nucleic acid amplification reaction, for example, the reagents necessary for the amplification reaction are introduced into each of the horizontal flow channels 104. Different nucleic acid templates are introduced into the vertical flow channels 102. In certain analyses, the primer introduced as part of the reagent mixture that is introduced into each of the horizontal flow channels 104 might differ between flow channels. This allows each nucleic acid template to be reacted with a number of different primers.

Figure 1B:
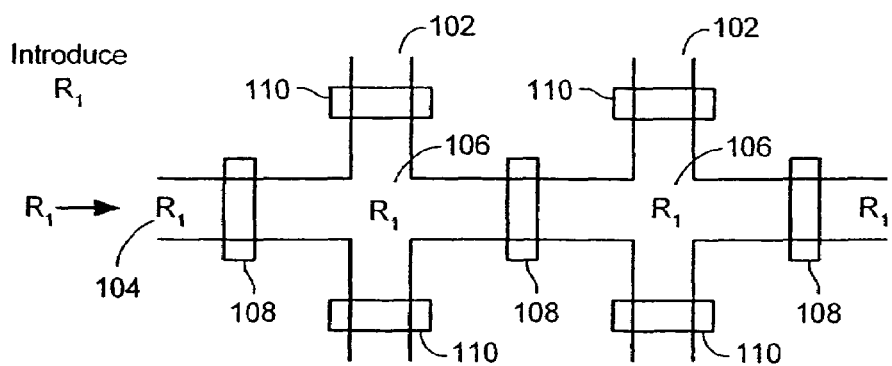
FIGS. 1B-E show enlarged views of a portion of the device shown in FIG. 1A and illustrates its operation.
Figure 1C:
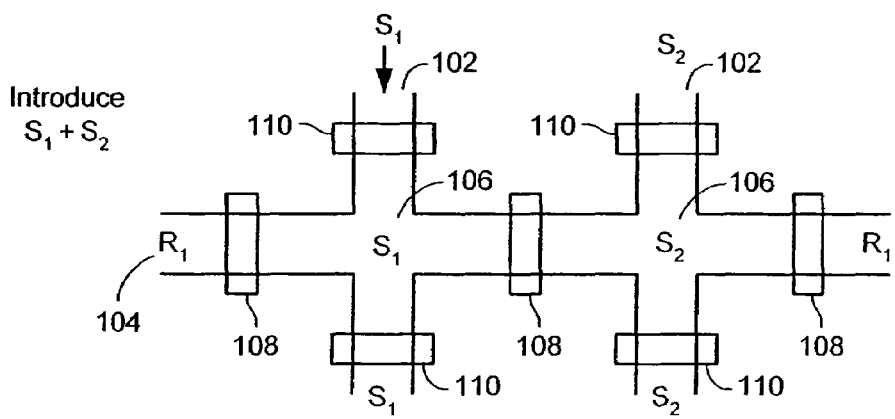

FIGS. 1B-E show enlarged plan views of adjacent reaction sites in the device depicted in FIG. 1A to illustrate more specifically how the device operates during an analysis. For the purposes of clarity, the intersections 106 are not shown in the form of reaction wells and control channels 116, 118 have been omitted, with just the column and row valves 110, 108 being shown (rectangular boxes). As shown in FIG. 1B, an analysis is commenced by closing column valves 110 and opening row valves 108 to allow solution flow through horizontal flow channel 104 while blocking flow through vertical flow channels 102. Reagent R1 is then introduced into horizontal flow channel 104 and flowed completely through the length of the horizontal flow channel 104 such that all the reaction sites 106 are filled. Solution flow through horizontal channel 104 can be achieved by an external pump, but more typically is achieved by incorporating a peristaltic pump into the elastomeric device itself as described in detail in Unger et al. (2000) Science 288:113-116, and PCT Publication WO 01/01025, for example.

Figure 1D:
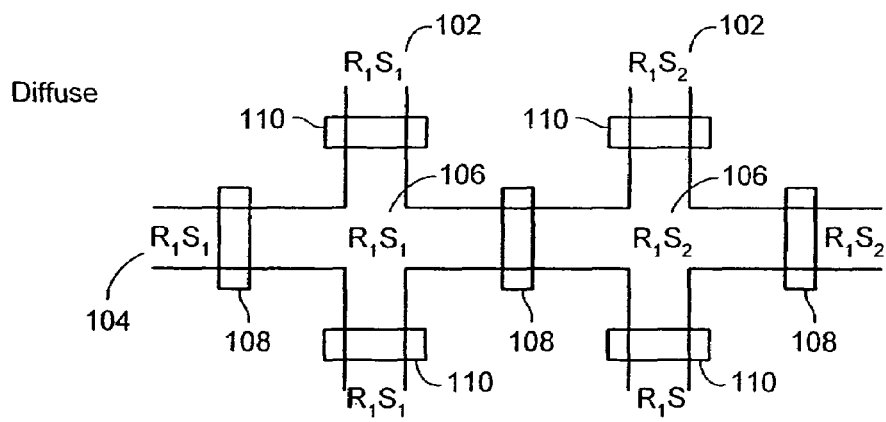
Figure 1E:
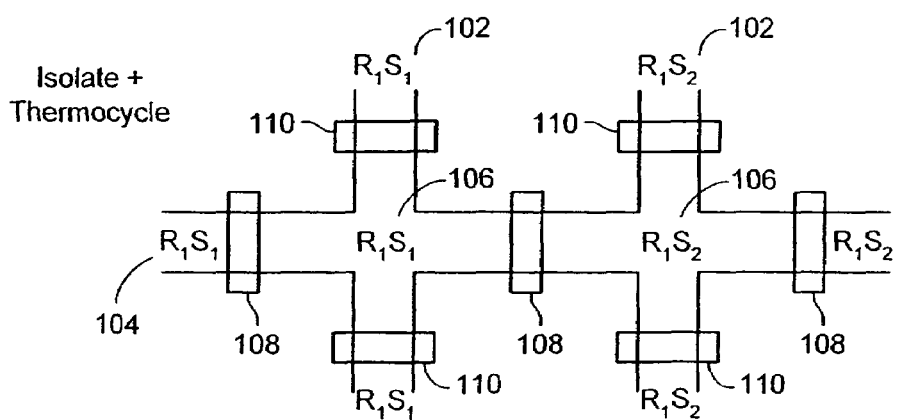

Once R1 has been introduced, row valves 108 are closed and column valves 102 opened (see FIG. 1C). This allows samples S1 and S2 to be introduced into vertical flow channels 102 and to flow through their respective flow channels. As the samples flow through the vertical flow channels 102, they expel R1 from the reaction sites 106, thus leaving sample at reaction sites 106. Then, as shown in FIG. 1D, row valves 108 are opened to allow S1 and S2 to diffuse and mix with R1. Thus, a mixture of sample and reactant (R1S1 and R1S2) is obtained in the region of each intersection or reaction site 106. After allowing a sufficient time for S1 and S2 to diffuse with R1, all row and column valves 108, 110 are closed to isolate S1 and S2 within the region of their respective reaction sites 106 and to prevent intermixing of S1 and S2 (see FIG. 1E). The mixtures are then allowed to react and the reactions detected by monitoring the intersection 106 or the cross-shaped region that includes the intersection 106. For analyses requiring heating (e.g., thermocycling during amplification reactions), the device is placed on a heater and heated while the samples remain isolated.

Figure 1F:
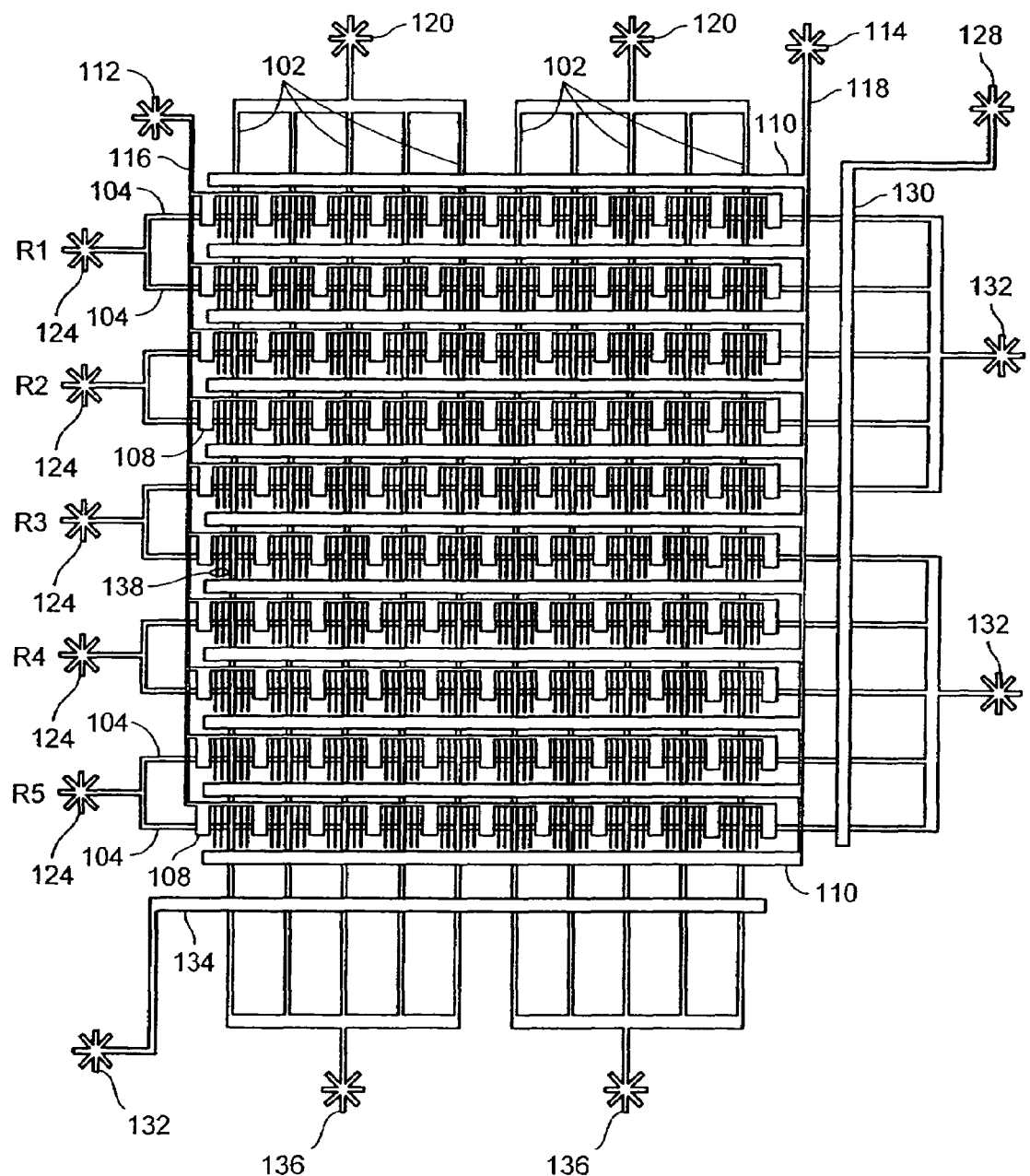
FIG. 1F is a schematic representation of another exemplary matrix design device that utilizes guard channels to reduce sample evaporation.

A modified version of the device shown in FIG. 1A is shown in FIG. 1F. The general structure bears many similarities with that depicted in FIG. 1A, and common elements in both figures share the same reference numbers. The device 150 illustrated in FIG. 1F differs in that pairs of horizontal flow channels 104 are joined to a common inlet 124. This essentially enables duplicate sets of reagents to be introduced into two adjacent flow channels with just a single injection into inlet 124. The use of a common inlet is further extended with respect to the vertical flow channels 102. In this particular example, each sample is introduced into five vertical flow channels 102 with a single injection into sample inlet 120. Thus, with this particular device, there are essentially ten replicate reactions for each particular combination of sample and reagent. Of course, the number of replicate reactions can be varied as desired by altering the number of vertical and/or horizontal flow channels 102, 104 that are joined to a common inlet 120, 124.

The device shown in FIG. 1F also includes a separate control channel inlet 128 that regulates control channel 130 that can be used to govern solution flow toward outlets 132 and another control channel inlet 132 that regulates control channel 134 that regulates solution flow to outlets 136. Additionally, device 150 incorporates guard channels 138. In this particular design, the guard channels 138 are formed as part of control channels 116. As indicated supra, the guard channels 138 are smaller than the row valves 108; consequently, the membranes of the guard channels 138 are not deflected into the underlying horizontal flow channels 104 such that solution flow is disrupted.

Finally, the design shown in FIG. 1F differs in that reaction does not occur in wells at the intersection of the horizontal and vertical flow lines, but in the intersection itself.

V. Blind Channel Designs

A. General

Devices utilizing a blind channel design have certain features. First, the devices include one or more flow channels from which one or more blind channels branch. As indicated above, the end region of such channels can serve as a reaction site. A valve formed by an overlaying flow channel can be actuated to isolate the reaction site at the end of the blind channel. The valves provide a mechanism for switchably isolating the reaction sites.

Second, the flow channel network in communication with the blind channels is configured such that all or most of the reaction sites can be filled with a single or a limited number of inlets (e.g., less than 5 or less than 10). The ability to fill a blind flow channel is made possible because the devices are made from elastomeric material. The elastomeric material is sufficiently porous such that air within the flow channels and blind channels can escape through these pores as solution is introduced into the channels. The lack of porosity of materials utilized in other microfluidic devices precludes use of the blind channel design because air in a blind channel has no way to escape as solution is injected.

A third characteristic is that one or more reagents are non-covalently deposited on a base layer of elastomer during manufacture (see infra for further details on the fabrication process) within the reaction sites. The reagent(s) are non-covalently attached because the reagents are designed to become dissolved when sample is introduced into the reaction site. To maximize the number of analyses, a different reactant or set of reactants is deposited at each of the different reaction sites.

Certain blind channel devices are designed such that the reaction sites are arranged in the form of an array.

Thus, in those blind channel devices designed for conducting nucleic acid amplification reactions, for example, one or more of the reagents required for conducting the extension reaction are deposited at each of the reaction sites during manufacture of the device. Such reagents include, for example, all or some of the following: primers, polymerase, nucleotides, cofactors, metal ions, buffers, intercalating dyes and the like. To maximize high throughput analysis, different primers selected to amplify different regions of DNA are deposited at each reaction site. Consequently, when a nucleic acid template is introduced into the reaction sites via inlet, a large number of extension reactions can be performed at different segments of the template. Thermocycling necessary for an amplification reaction can be accomplished by placing the device on a thermocycling plate and cycling the device between the various required temperatures.

The reagents can be immobilized in a variety of ways. For example, in some instances one or more of the reagents are non-covalently deposited at the reaction site, whereas in other instances one or more of the reagents is covalently attached to the substrate at the reaction site. If covalently attached, the reagents can be linked to the substrate via a linker. A variety of linker types can be utilized such as photochemical/photolabile linkers, themolabile linkers, and linkers that can be cleaved enzymatically. Some linkers are bifunctional (i.e., the linker contains a functional group at each end that is reactive with groups located on the element to which the linker is to be attached); the finctional groups at each end can be the same or different. Examples of suitable linkers that can be used in some assays include straight or branched-chain carbon linkers, heterocyclic linkers and peptide linkers. A variety of types of linkers are available from Pierce Chemical Company in Rockford, Ill. and are described in EPA 188,256; U.S. Pat. Nos. 4,671,958; 4,659,839; 4,414,148; 4,669,784; 4,680,338, 4,569,789 and 4,589,071, and by Eggenweiler, H. M, Pharmaceutical Agent Discovery Today 1998, 3, 552. NVOC (6 nitroveratryloxycarbonyl) linkers and other NVOC-related linkers are examples of suitable photochemical linkers (see, e.g., WO 90/15070 and WO 92/10092). Peptides that have protease cleavage sites are discussed, for example, in US 5,382,513.

B. Exemplary Designs and Uses

Figure 2:
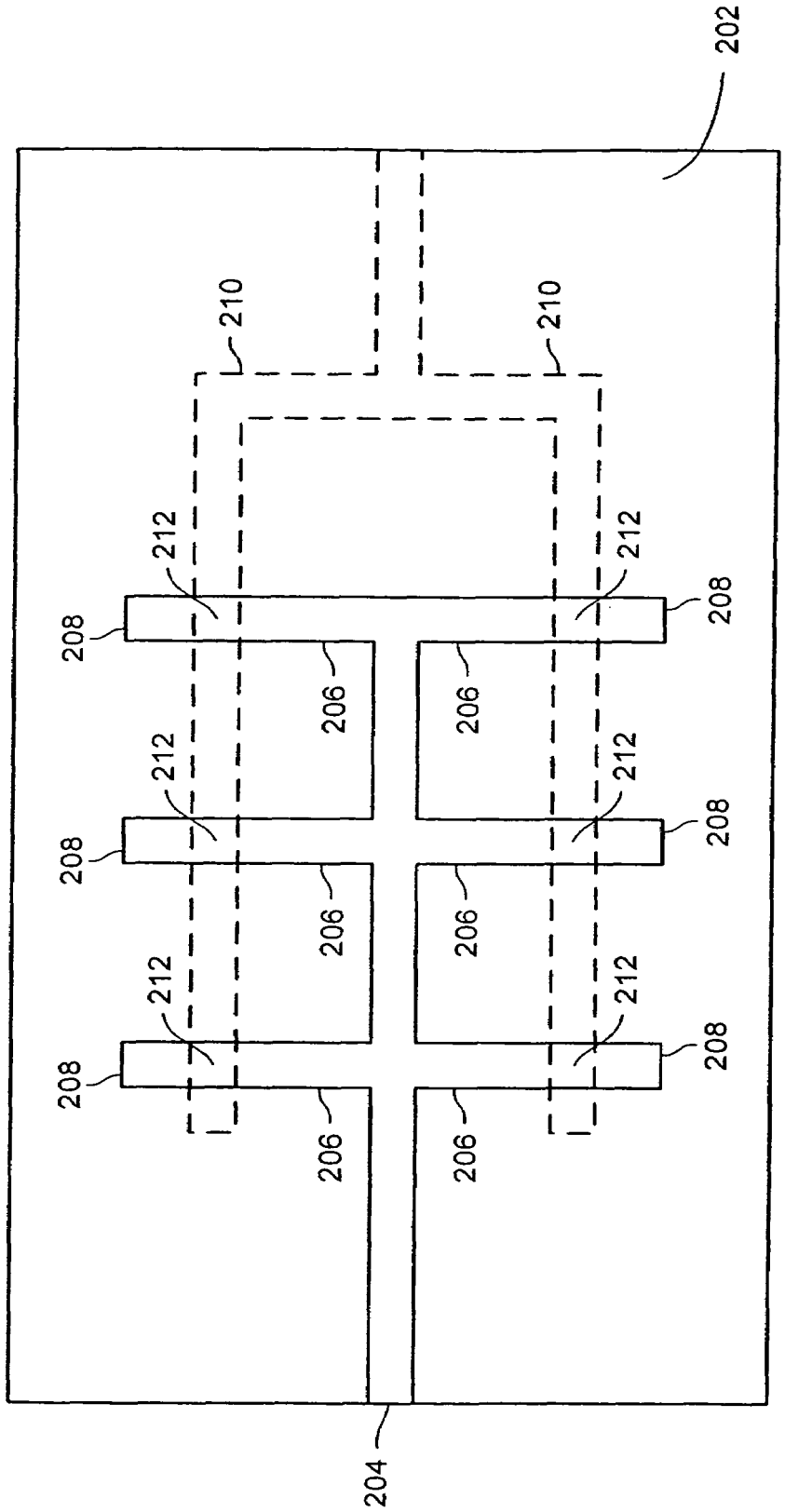
FIG. 2 is a plan view of an exemplary blind channel device.

FIG. 2 is a simplified plan view of one exemplary device utilizing the blind channel design. The device 200 includes a flow channel 204 and a set of branch flow channels 206 branching therefrom that are formed in an elastomeric substrate 202. Each branch flow channel 206 terminates in a reaction site 208, thereby forming an array of reaction sites. Overlaying the branch flow channels 206 is a control channel 210 that is separated from the branch flow channels 206 by membranes 212. Actuation of control channel 210 causes membranes 212 to deflect into the branch flow channels 206

(i.e., to function as a valve), thus enabling each of the reaction sites 208 to be isolated from the other reaction sites.

Operation of such a device involves injecting a test sample into flow channel 204 with solution subsequently flowing into each of branch channels 206. Once the sample has filled each branch channel 206, control channel 210 is actuated to cause activation of valves/membranes 212 to deflect into branch channels 206, thereby sealing off each of reaction sites 208. As the sample flows into and remains in reaction sites 208, it dissolves reagents previously spotted at each of the reaction sites 208. Once dissolved, the reagents can react with the sample. Valves 212 prevent the dissolved reagents at each reaction site 208 from intermixing by diffusion. Reaction between sample and reagents are then detected, typically within reaction site 208. Reactions can optionally be heated as described in the temperature control section infra.

Figure 3A:
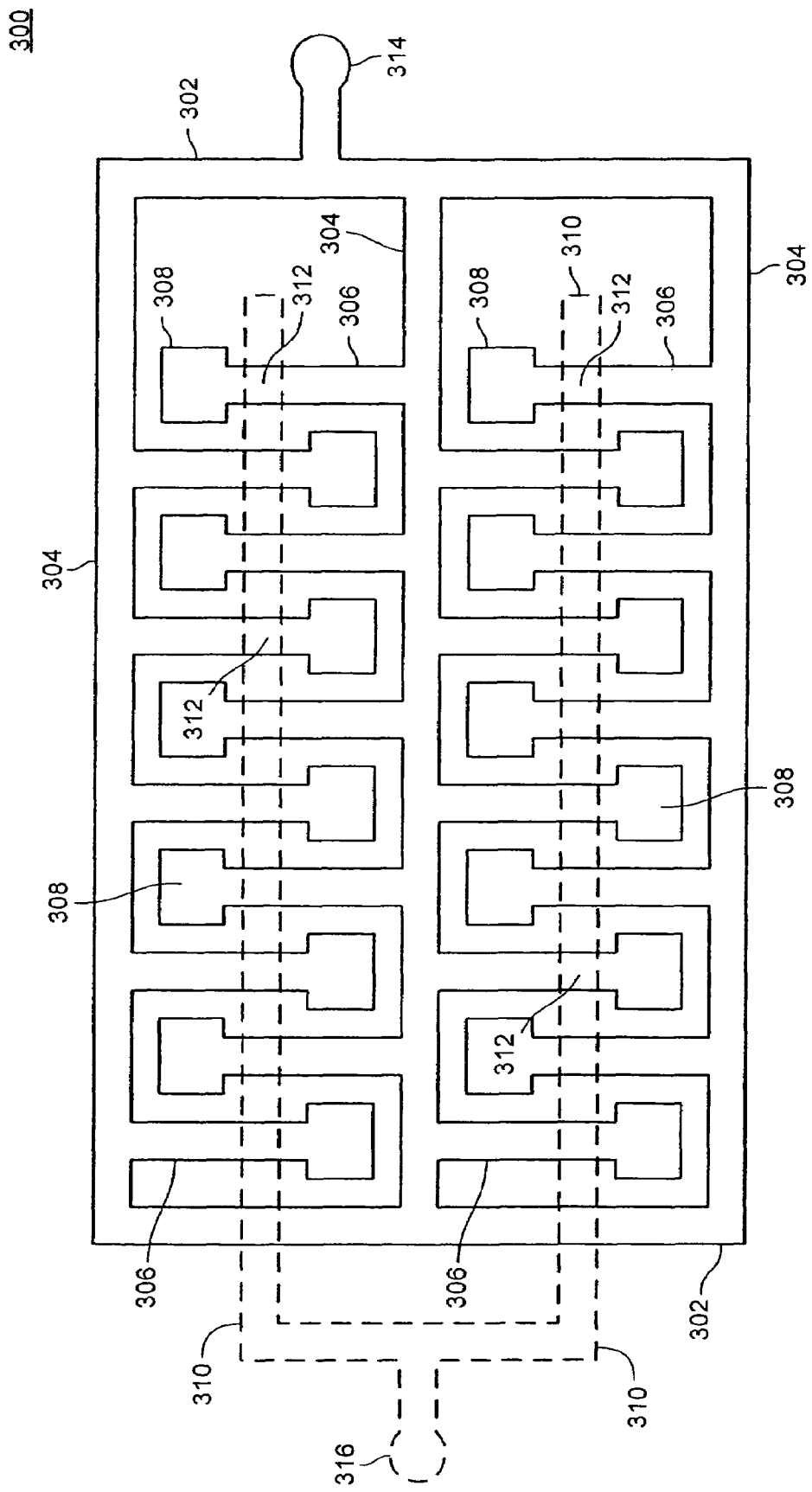
FIG. 3A is a plan view of another exemplary blind channel device.

FIG. 3A illustrates an example of a somewhat more complex blind flow channel design. In this particular design 300, each of a set of horizontal flow channels 304 are connected at their ends to two vertical flow channels 302. A plurality of branch flow channels 306 extend from each of the horizontal flow channels 304. The branch flow channels 304 in this particular design are interleaved such that the branch channel 306 attached to any given horizontal flow channel 304 is positioned between two branch channels 306 joined to an immediately adjacent horizontal flow channel 304, or positioned between a branch flow channel 306 joined to an immediately adjacent flow channel 304 and one of the vertical flow channels 302. As with the design depicted in FIG. 3A, each branch flow channel 306 terminates in a reaction site 308. Also consistent with the design shown in FIG. 3A, a control channel 310 overlays each of the branch channels and is separated from the underlying branch channel by membrane 312. The control channel is actuated at port 316. The vertical and horizontal flow channels 302, 304 are interconnected such that injection of sample into inlet 314 allows solution to flow throughout the horizontal and vertical flow channel network and ultimately into each of the reaction sites 308 via the branch flow channels 306.

Hence, in operation, sample is injected into inlet to introduce solution into each of the reaction sites. Once the reaction sites are filled, valves/membranes are actuated to trap solution within the reaction sites by pressurizing the control channels at port. Reagents previously deposited in the reaction sites become resuspended within the reaction sites, thereby allowing reaction between the deposited reagents and sample within each reaction site. Reactions within the reaction sites are monitored by a detector. Again, reactions can optionally be controllably heated according to the methods set forth in the temperature control section below.

Figure 3B:
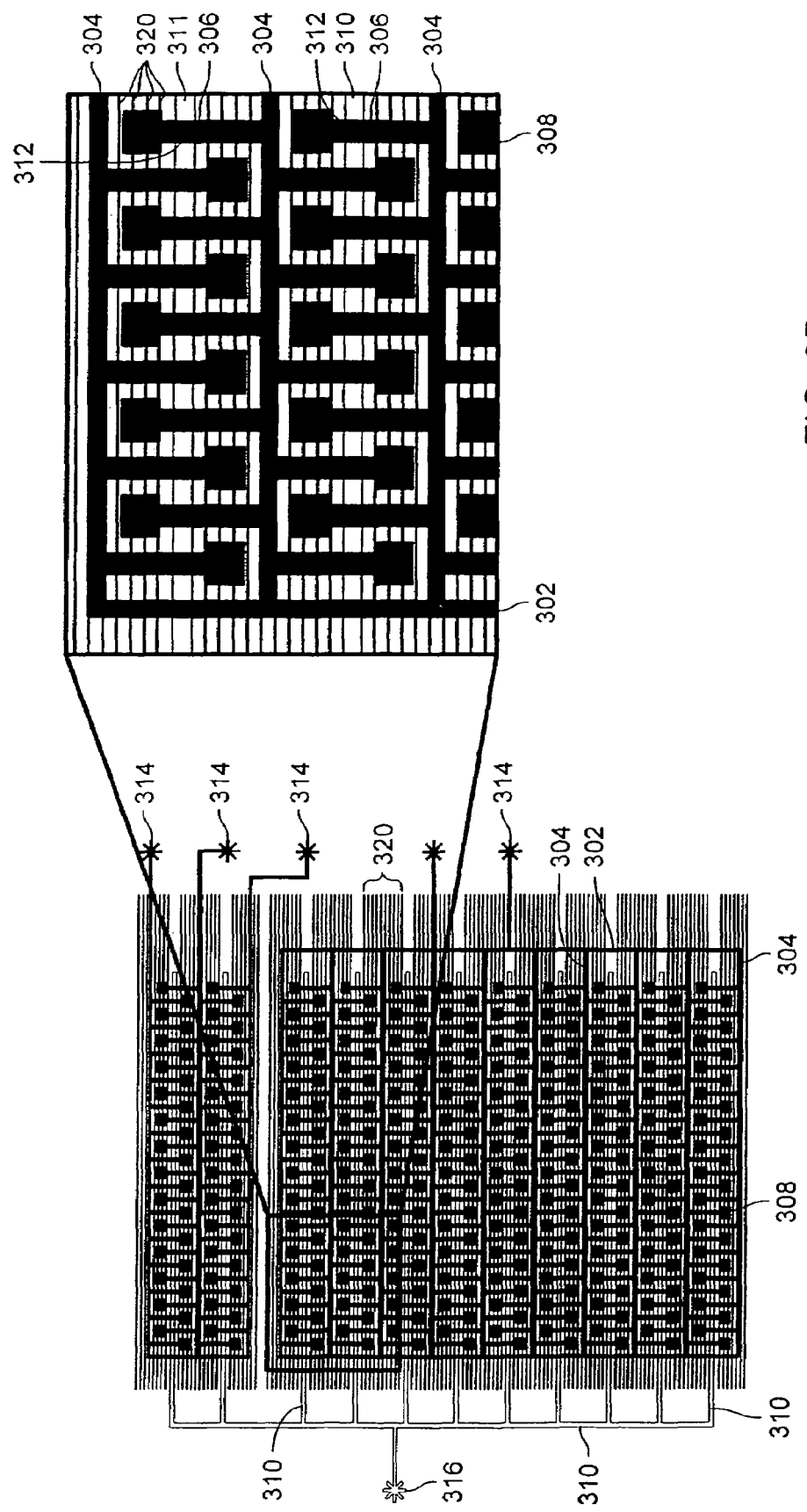
FIG. 3B is a schematic representation of a more complex blind channel device based upon the unit of the general design depicted in FIG. 3A.

An even more complicated version of the general design illustrated in FIG. 3A is shown in FIG. 3B. The device shown in FIG. 3B is one in which the unit organization of the horizontal and branch flow channels 302 shown in FIG. 3A is repeated multiple times. The device shown in FIG. 3B further illustrates the inclusion of guard channels 320 in those devices to be utilized in applications that involve heating (e.g., thermocycling). An exemplary orientation of the guard channels 320 with respect to the flow channels 304 and branch channels 306 is shown in the enlarged view depicted in FIG. 3C. The guard channels 320 overlay the branch flow channels 306 and reaction sites 308. As discussed above, water is flowed through the guard channels 320 during heating of the device 300 to increase the local concentration of water in the device, thereby reducing evaporation of water from solution in the flow channels 306 and reaction sites 308.

The features of blind channel devices discussed at the outset of this section minimizes the footprint of the device and enable a large number of reaction sites to be formed on the device and for high densities to be obtained. For example, devices of this type having 2500 reaction sites can readily be manufactured to fit on a standard microscope slides (25 mm×75 mm). The foregoing features also enable very high densities of reaction sites to be obtained with devices utilizing the blind channel design. For example, densities of at least 50, 60, 70, 80, 90 or 100 reaction sites/cm$^2$ or any integral density value therebetween can be readily obtained. However, certain devices have even higher densities ranging, for example, between 100 to 4000 reaction sites/cm$^2$, or any integral density value therebetween. For instance, some devices have densities of at least 100, 150, 200, 250, 300, 400, 500, 600, 700, 800, 900 or 1000 sites/cm$^2$. Devices with very high densities of at least, 2000, 3000, or 4000 sites/cm$^2$ are also obtainable. Such high densities directly translate into a very large number of reaction sites on the device. Devices utilizing the blind channel architecture typically have at least 10-100 reaction sites, or any integral number of sites therebetween. More typically, the devices have at least 100-1,000 reaction sites, or any integral number of sites therebetween. Higher density devices can have even more reaction sites, such as at least 1,000-100,000 reaction sites, or any integral number of sites therebetween. Thus, certain devices have at least 100; 500; 1,000; 2,000; 3,000; 4,000; 5,000; 6,000; 7,000; 8,000; 9,000; 10,000; 20,000; 30,000; 40,000; 50,000; or 100,000 reaction sites depending upon the overall size of the device.

The large number of reaction sites and densities that can be obtained is also a consequence of the ability to fabricate very small wells or cavities. For example, the cavities or wells typically have a volume of less than 50 nL; in other instances less than 40 nL, 30 nL, 20 nL or 10 nL; and in still other instances less than 5 nL or 1 nL. As a specific example, certain devices have wells that are 300 microns long, 300 microns wide and 10 microns deep.

The blind channel devices provided herein can utilize certain design features and methodologies discussed in PCT Applications PCT/US01/44549 (published as WO 02/43615) and PCT/US02/10875 (published as WO 02/082047), including, for example, strategies for filling dead-ended channels, liquid priming, pressurized outgas priming, as well as various strategies for displacing gas during the filling of microfluidic channels. Both of these PCT publications are incorporated herein by reference in their entirety for all purposes.

VI. Hybrid Designs

Still other devices are hybrids of the matrix and blind fill designs. The design of devices of this type is similar to the blind channel device shown in FIG. 3A, except that each horizontal flow channel is connected to its own sample inlet port(s) and the horizontal flow channels are not interconnected via vertical flow channels. Consequently, sample introduced into any given horizontal flow channel fills only that horizontal flow channel and reaction sites attached thereto. Whereas, in the blind flow channel device shown in FIG. 3A, sample can flow between the horizontal flow channels 304 via vertical flow channels 302.

Figure 4:
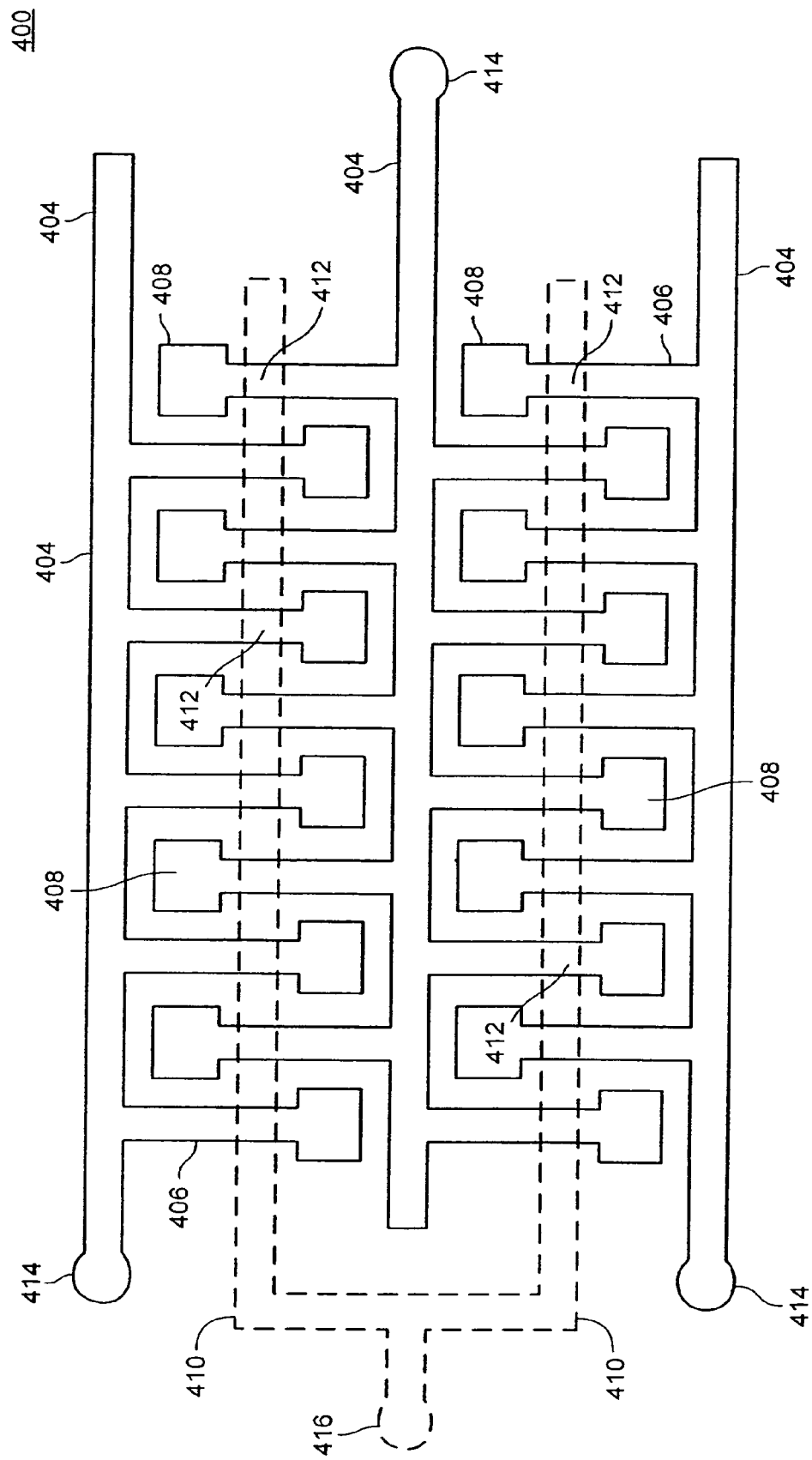
FIG. 4 is a plan view of a device utilizing the hybrid design.

An example of devices of this general device is shown in FIG. 4. Device 400 comprises a plurality of horizontal flow channels 404, each of which has a plurality of branch flow channels 406 extending from it and its own sample inlet 414. A control channel 410 overlays each of the branch flow channels 406 and membrane (valve) 412 separates the control channel 410 from the underlying branch flow channel 406. As with the blind flow channel design, actuation of the control channel at inlet 416 causes deflection of membranes 412 into the branch flow channels 406 and isolation of reaction sites 408. In a variation of this design, each horizontal flow channel 404 can include an inlet 414 at each end, thus allowing sample to be introduced from both ends.

In some instances, reagents are deposited at the reaction sites during manufacture of the device. This enables a large number of samples to be tested under a relatively large number of reaction conditions in a short period of time without requiring time-consuming additions of reagents as required with the matrix devices. Alternatively, reaction mixtures can be prepared prior to injection on the chip. Once the mixtures are injected, they can be analyzed or further treated (e.g., heated).

By injecting different samples into each of the horizontal flow channels, a large number of samples can be rapidly analyzed. Assuming reagents have been previously deposited at the reaction sites, the presence of the same reagent at each reaction site associated with any given horizontal flow channel provides a facile way to conduct a number of replicate reactions with each sample. If instead, the reagent at the reaction sites differ for any given flow channel, then each sample is essentially simultaneously exposed to a variety of different reaction conditions.

Thus, the devices provided herein are tailored for a variety of different types of investigations. If an investigation involves screening of a relatively large number of different samples under user controlled conditions (e.g., 100 samples against 100 user selected reagents), then the matrix devices provide a useful solution. If, however, the investigation involves analyzing one or a limited number of samples under a wide variety of reaction conditions (e.g., one sample against 10,000 reaction conditions), then the blind channel design is useful. Finally, if one wants to examine a relatively large number of samples against defined reaction conditions without having to inject reagents (e.g., 100 samples against 100 previously defined reagents), then the hybrid devices are useful.

VII. Temperature Control

A. Devices and Components

A number of different options of varying sophistication are available for controlling temperature within selected regions of the microfluidic device or the entire device. Thus, as used herein, the term temperature controller is meant broadly to refer to a device or element that can regulate temperature of the entire microfluidic device or within a portion of the microfluidic device (e.g., within a particular temperature region or at one or more junctions in a matrix of blind channel-type microfluidic device).

Generally, the devices are placed on a thermal cycling plate to thermal cycle the device. A variety of such plates are readily available from commercial sources, including for example the ThermoHybaid Px2 (Franklin, Mass.), MJ Research PTC-200 (South San Francisco, Calif.), Eppendorf Part# E5331 (Westbury, N.Y.), Techne Part# 205330 (Princeton, N.J.).

To ensure the accuracy of thermal cycling steps, in certain devices it is useful to incorporate sensors detecting temperature at various regions of the device. One structure for detecting temperature is a thermocouple. Such a thermocouple could be created as thin film wires patterned on the underlying substrate material, or as wires incorporated directly into the microfabricated elastomer material itself.

Temperature can also be sensed through a change in electrical resistance. For example, change in resistance of a thermistor fabricated on an underlying semiconductor substrate utilizing conventional techniques can be calibrated to a given temperature change. Alternatively, a thermistor could be inserted directly into the microfabricated elastomer material. Still another approach to detection of temperature by resistance is described in Wu et al. in "MEMS Flow Sensors for Nano-fluidic Applications", Sensors and Actuators A 89 152-158 (2001), which is hereby incorporated by reference in its entirety. This paper describes the use of doped polysilicon structures to both control and sense temperature. For polysilicon and other semiconductor materials, the temperature coefficient of resistance can be precisely controlled by the identity and amount of dopant, thereby optimizing performance of the sensor for a given application.

Thermo-chromatic materials are another type of structure available to detect temperature on regions of an amplification device. Specifically, certain materials dramatically and reproducibly change color as they pass through different temperatures. Such a material could be added to the solution as they pass through different temperatures. Thermo-chromatic materials could be formed on the underlying substrate or incorporated within the elastomer material. Alternatively, thermo-chromatic materials could be added to the sample solution in the form of particles.

Another approach to detecting temperature is through the use of an infrared camera. An infrared camera in conjunction with a microscope could be utilized to determine the temperature profile of the entire amplification structure. Permeability of the elastomer material to radiation would facilitate this analysis.

Yet another approach to temperature detection is through the use of pyroelectric sensors. Specifically, some crystalline materials, particularly those materials also exhibiting piezoelectric behavior, exhibit the pyroelectric effect. This effect describes the phenomena by which the polarization of the material's crystal lattice, and hence the voltage across the material, is highly dependent upon temperature. Such materials could be incorporated onto the substrate or elastomer and utilized to detect temperature.

Other electrical phenomena, such as capacitance and inductance, can be exploited to detect temperature in accordance with embodiments of the present invention.

B. Verification of Accurate Thermocycling

As described in greater detail in the fabrication section infra, blind channel devices have a base layer onto which reagents are placed. The structure comprising the two layers containing the flow channels and control channels is overlayed on the base layer such that the flow channels are aligned with the deposited reagents. The other side of the base layer is then placed upon a substrate (e.g., glass). Usually, the reaction site at which reaction occurs is about 100-150 microns above the substrate/glass interface. Using known equations for thermal diffusivity and appropriate values for the elastomers and glass utilized in the device, one can calculate the time required for the temperature within the reaction site to reach the temperature the controller seeks to maintain. The calculated values shown in Table 1 demonstrate that temperature can rapidly be reached, even using elastomer and glass layers considerably thicker than utilized in devices in which the reaction site is approximately 100-150 microns (i.e., the typical distance for the devices described herein).

TABLE 1

Calculated heat diffusion lengths through PDMS and glass layers at the indicated time periods.

|  | 1 second | 10 seconds | 100 seconds |
|---|---|---|---|
| PDMS | 400 um | 1.26 mm | 4.0 mm |
| Glass | 640 um | 2.0 mm | 6.4 mm |

Figure 5:
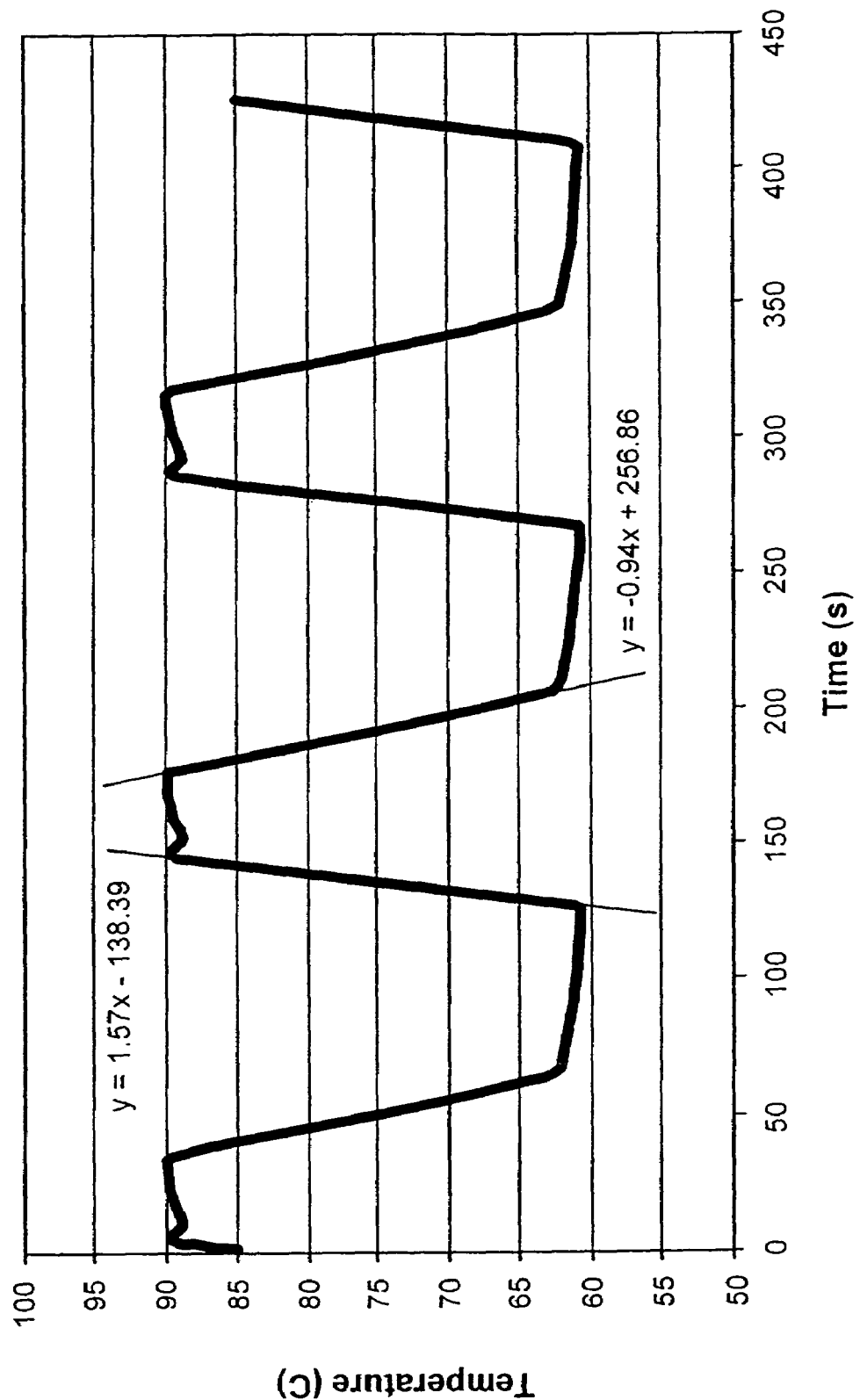
FIG. 5 is a chart showing ramp up and down times to conduct a thermocycling reaction.

FIG. 5 illustrates the rapidity at which the desired temperature is achieved using a blind channel device.

In another embodiment, temperature may be measured by using double stranded oligonucleotide polymers having known tms wherein an intercollating dye whose intercollation indicates the whether the oligonucleotide is hybridized or denatured, such as SYBR Green(™) or ethidium bromide for example, wherein by introducing a solution containing the oligonucleotide with the dye into the chambers of the microfluidic device having an array of reaction chambers can be used to determine the extent to which the temperature of each chamber is consistent across the array. In this embodiment, as the temperature is raised above the tm, the intercalating dye changes its relation to the oligonucleotide upon it sdenataturation into a single stranded oligonucleotide. Alternatively, the if the temperature is above the tm and is lowered, an the intercollation of the dye into the now annealed oligonucleotide may be monitored. The use of the dye in essence provides for an "oligonucleotide thermometer" which changes a property, such as fluorescence, in response to a temperature change relative to the tm of the oligonucleotide. By designing or using oligonucleotides of a selected tm, the extent to which an array of reaction chambers change temperature in a similar manner can be determined.

VIII. Detection

A. General

A number of different detection strategies can be utilized with the microfluidic devices that are provided herein. Selection of the appropriate system is informed in part on the type of event and/or agent being detected. The detectors can be designed to detect a number of different signal types including, but not limited to, signals from radioisotopes, fluorophores, chromophores, electron dense particles, magnetic particles, spin labels, molecules that emit chemiluminescence, electrochemically active molecules, enzymes, cofactors, enzymes linked to nucleic acid probes and enzyme substrates.

Illustrative detection methodologies suitable for use with the present microfluidic devices include, but are not limited to, light scattering, multichannel fluorescence detection, UV and visible wavelength absorption, luminescence, differential reflectivity, and confocal laser scanning. Additional detection methods that can be used in certain application include scintillation proximity assay techniques, radiochemical detection, fluorescence polarization, fluorescence correlation spectroscopy (FCS), time-resolved energy transfer (TRET), fluorescence resonance energy transfer (FRET) and variations such as bioluminescence resonance energy transfer (BRET). Additional detection options include electrical resistance, resistivity, impedance, and voltage sensing.

Detection occurs at a "detection section," or "detection region." These terms and other related terms refer to the portion of the microfluidic device at which detection occurs. As indicated above, with devices utilizing the blind channel design, the detection section is generally the reaction site as isolated by the valve associated with each reaction site. The detection section for matrix-based devices is usually within regions of flow channels that are adjacent an intersection, the intersection itself, or a region that encompasses the intersection and a surrounding region.

The detection section can be in communication with one or more microscopes, diodes, light stimulating devices (e.g., lasers), photomultiplier tubes, processors and combinations of the foregoing, which cooperate to detect a signal associated with a particular event and/or agent. Often the signal being detected is an optical signal that is detected in the detection section by an optical detector. The optical detector can include one or more photodiodes (e.g., avalanche photodiodes), a fiber-optic light guide leading, for example, to a photomultiplier tube, a microscope, and/or a video camera (e.g., a CCD camera).

Detectors can be microfabricated within the microfluidic device, or can be a separate element. If the detector exists as a separate element and the microfluidic device includes a plurality of detection sections, detection can occur within a single detection section at any given moment. Alternatively, scanning systems can be used. For instance, certain automated systems scan the light source relative to the microfluidic device; other systems scan the emitted light over a detector, or include a multichannel detector. As a specific illustrative example, the microfluidic device can be attached to a translatable stage and scanned under a microscope objective. A signal so acquired is then routed to a processor for signal interpretation and processing. Arrays of photomultiplier tubes can also be utilized. Additionally, optical systems that have the capability of collecting signals from all the different detection sections simultaneously while determining the signal from each section can be utilized.

External detectors are usable because the devices that are provided are completely or largely manufactured of materials that are optically transparent at the wavelength being monitored. This feature enables the devices described herein to utilize a number of optical detection systems that are not possible with conventional silicon-based microfluidic devices.

A particularly preferred detector uses a CCD camera and an optical path that provides for a large field of view and a high numerical aperture to maximize the amount of light collected from each reaction chamber. In this regard, the CCD is used as an array of photodetectors wherein each pixel or group of pixels corresponds to a reaction chamber rather than being used to produce an image of the array. Thus, the optics may be altered such that image quality is reduced or defocused to increase the depth of field of the optical system to collect more light from each reaction chamber.

A detector can include a light source for stimulating a reporter that generates a detectable signal. The type of light source utilized depends in part on the nature of the reporter being activated. Suitable light sources include, but are not limited to, lasers, laser diodes and high intensity lamps. If a laser is utilized, the laser can be utilized to scan across a set of detection sections or a single detection section. Laser diodes can be microfabricated into the microfluidic device itself. Alternatively, laser diodes can be fabricated into another device that is placed adjacent to the microfluidic device being utilized to conduct a thermal cycling reaction such that the laser light from the diode is directed into the detection section.

Detection can involve a number of non-optical approaches as well. For example, the detector can also include, for example, a temperature sensor, a conductivity sensor, a potentiometric sensor (e.g., pH electrode) and/or an amperometric sensor (e.g., to monitor oxidation and reduction reactions).

A number of commercially-available external detectors can be utilized. Many of these are fluorescent detectors because of the ease in preparing fluorescently labeled reagents. Specific examples of detectors that are available include, but are not limited to, Applied Precision ArrayWoRx (Applied Precision, Issaquah, Wash.)).

B. Detection of Amplified Nucleic Acids

1. Intercalation Dyes

Certain intercalation dyes that only fluoresce upon binding to double-stranded DNA can be used to detect double-stranded amplified DNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., *Anal. Chem.* 66:1941-1948 (1994), which is incorporated by reference in its entirety.

2. FRET Based Detection Methods

Detection methods of this type involve detecting a change in fluorescence from a donor (reporter) and/or acceptor (quencher) fluorophore in a donor/acceptor fluorophore pair. The donor and acceptor fluorophore pair are selected such that the emission spectrum of the donor overlaps the excitation spectrum of the acceptor. Thus, when the pair of fluorophores are brought within sufficiently close proximity to one another, energy transfer from the donor to the acceptor can occur. This energy transfer can be detected.

FRET and template extension reactions. These methods generally utilize a primer labeled with one member of a donor/acceptor pair and a nucleotide labeled with the other member of the donor/acceptor pair. Prior to incorporation of the labeled nucleotide into the primer during an template-dependent extension reaction, the donor and acceptor are spaced far enough apart that energy transfer cannot occur. However, if the labeled nucleotide is incorporated into the primer and the spacing is sufficiently close, then energy transfer occurs and can be detected. These methods are particularly useful in conducting single base pair extension reactions in the detection of single nucleotide polymorphisms (see infra) and are described in U.S. Pat. No. 5,945,283 and PCT Publication WO 97/22719.

Quantitative RT-PCR. A variety of so-called "real time amplification" methods or "real time quantitative PCR" methods can also be utilized to determine the quantity of a target nucleic acid present in a sample by measuring the amount of amplification product formed during or after the amplification process itself. Fluorogenic nuclease assays are one specific example of a real time quantitation method which can be used successfully with the devices described herein. This method of monitoring the formation of amplification product involves the continuous measurement of PCR product accumulation using a dual-labeled fluorogenic oligonucleotide probe—an approach frequently referred to in the literature as the "TaqMan" method.

The probe used in such assays is typically a short (ca. 20-25 bases) polynucleotide that is labeled with two different fluorescent dyes. The 5' terminus of the probe is typically attached to a reporter dye and the 3' terminus is attached to a quenching dye, although the dyes can be attached at other locations on the probe as well. The probe is designed to have at least substantial sequence complementarity with the probe binding site on the target nucleic acid. Upstream and downstream PCR primers that bind to regions that flank the probe binding site are also included in the reaction mixture.

When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector.

One detector which is specifically adapted for measuring fluorescence emissions such as those created during a fluorogenic assay is the ABI 7700 manufactured by Applied Biosystems, Inc. in Foster City, Calif. Computer software provided with the instrument is capable of recording the fluorescence intensity of reporter and quencher over the course of the amplification. These recorded values can then be used to calculate the increase in normalized reporter emission intensity on a continuous basis and ultimately quantify the amount of the mRNA being amplified.

Additional details regarding the theory and operation of fluorogenic methods for making real time determinations of the concentration of amplification products are described, for example, in U.S. Pat. No. 5,210,015 to Gelfand, U.S. Pat. No. 5,538,848 to Livak, et al., and U.S. Pat. No. 5,863,736 to Haaland, as well as Heid, C. A., et al., *Genome Research,* 6:986-994 (1996); Gibson, U. E. M, et al., *Genome Research* 6:995-1001 (1996); Holland, P. M., et al., *Proc. Natl. Acad. Sci. USA* 88:7276-7280, (1991); and Livak, K. J., et al., *PCR Methods and Applications* 357-362 (1995), each of which is incorporated by reference in its entirety.

Thus, as the amplification reaction progresses, an increasing amount of dye becomes bound and is accompanied by a concomitant increase in signal.

Intercalation dyes such as described above can also be utilized in a different approach to quantitative PCR methods. As noted above, these dyes preferentially bind to double stranded DNA (e.g., SYBR GREEN) and only generate signal once bound. Thus, as an amplification reaction progresses, an increasing amount of dye becomes bound and is accompanied by a concomitant increase in signal that can be detected.

Molecular Beacons: With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye.

In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use is described further, for example, by Piatek, A. S., et al., Nat. Biotechnol. 16:359-63 (1998); Tyagi, S. and Kramer, F. R., Nature Biotechnology 14:303-308 (1996); and Tyagi, S. et al., Nat. Biotechnol. 16:49-53 (1998), each of which is incorporated by reference herein in their entirety for all purposes.

Invader: Invader assays (Third Wave Technologies, (Madison, Wis.)) are used for SNP genotyping and utilize an oligonucleotide, designated the signal probe, that is complementary to the target nucleic acid (DNA or RNA) or polymorphism site. A second oligonucleotide, designated the Invader Oligo, contains the same 5' nucleotide sequence, but the 3' nucleotide sequence contains a nucleotide polymorphism. The Invader Oligo interferes with the binding of the signal probe to the target nucleic acid such that the 5' end of the signal probe forms a "flap" at the nucleotide containing the polymorphism. This complex is recognized by a structure specific endonuclease, called the Cleavase enzyme. Cleavase cleaves the 5' flap of the nucleotides. The released flap binds with a third probe bearing FRET labels, thereby forming another duplex structure recognized by the Cleavase enzyme. This time the Cleavase enzyme cleaves a fluorophore away from a quencher and produces a fluorescent signal. For SNP genotyping, the signal probe will be designed to hybridize with either the reference (wild type) allele or the variant (mutant) allele. Unlike PCR, there is a linear amplification of signal with no amplification of the nucleic acid. Further details sufficient to guide one of ordinary skill in the art is provided by, for example, Neri, B. P., et al., *Advances in Nucleic Acid and Protein Analysis* 3826:117-125, 2000).

Nasba: Nucleic Acid Sequence Based Amplification (NASBA) is a detection method using RNA as the template. A primer complementary to the RNA contains the sequence for the T7 promoter site. This primer is allowed to bind with the template RNA and Reverse Transcriptase (RT) added to generate the complementary strand from 3' to 5'. RNase H is subsequently added to digest away the RNA, leaving single stranded cDNA behind. A second copy of the primer can then bind the single stranded cDNA and make double stranded cDNA. T7 RNA polymerase is added to generate many copies of the RNA from the T7 promoter site that was incorporated into the cDNA sequence by the first primer. All the enzymes mentioned are capable of functioning at 41° C. (See, e.g., Compton, J. Nucleic Acid Sequence-based Amplification, Nature 350: 91-91, 1991.)

Figure 20:
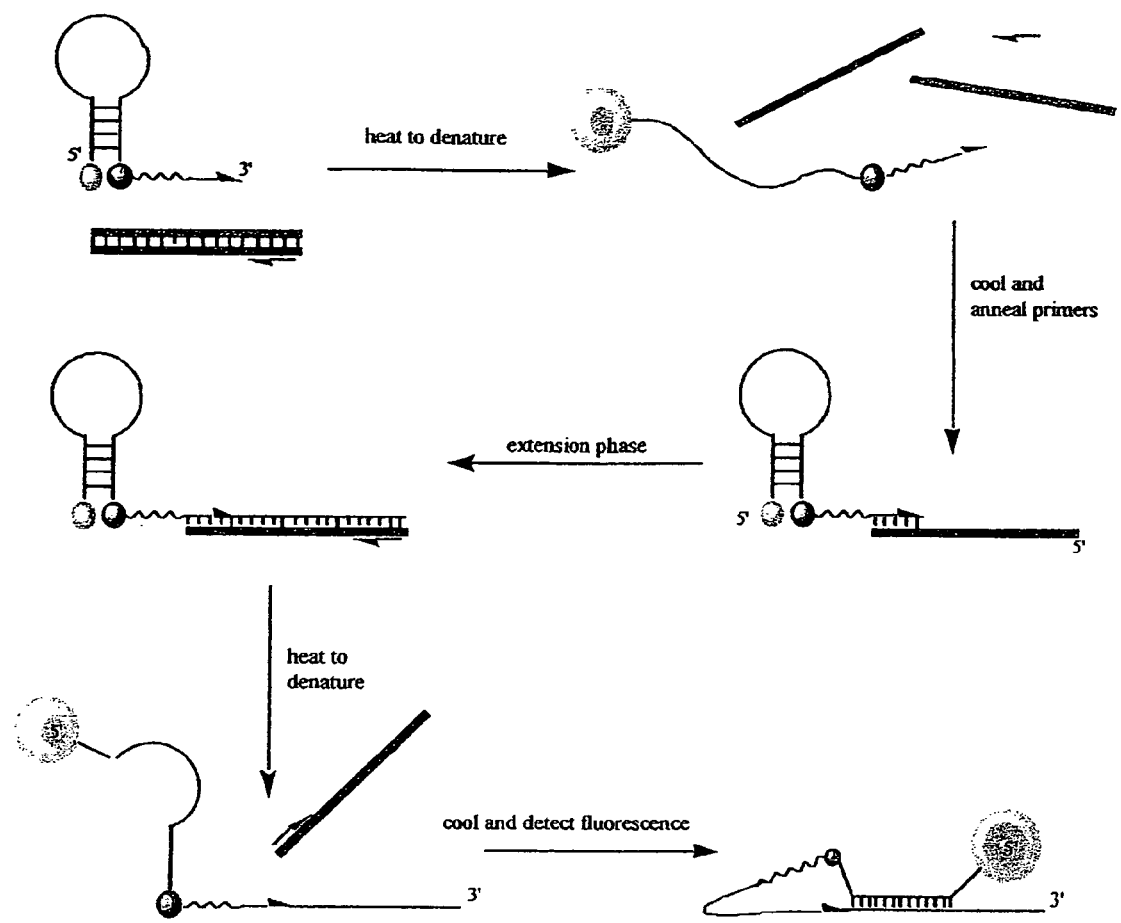
FIG. 20 depicts an isothermic amplification scheme— SCORPION
Figure 24:
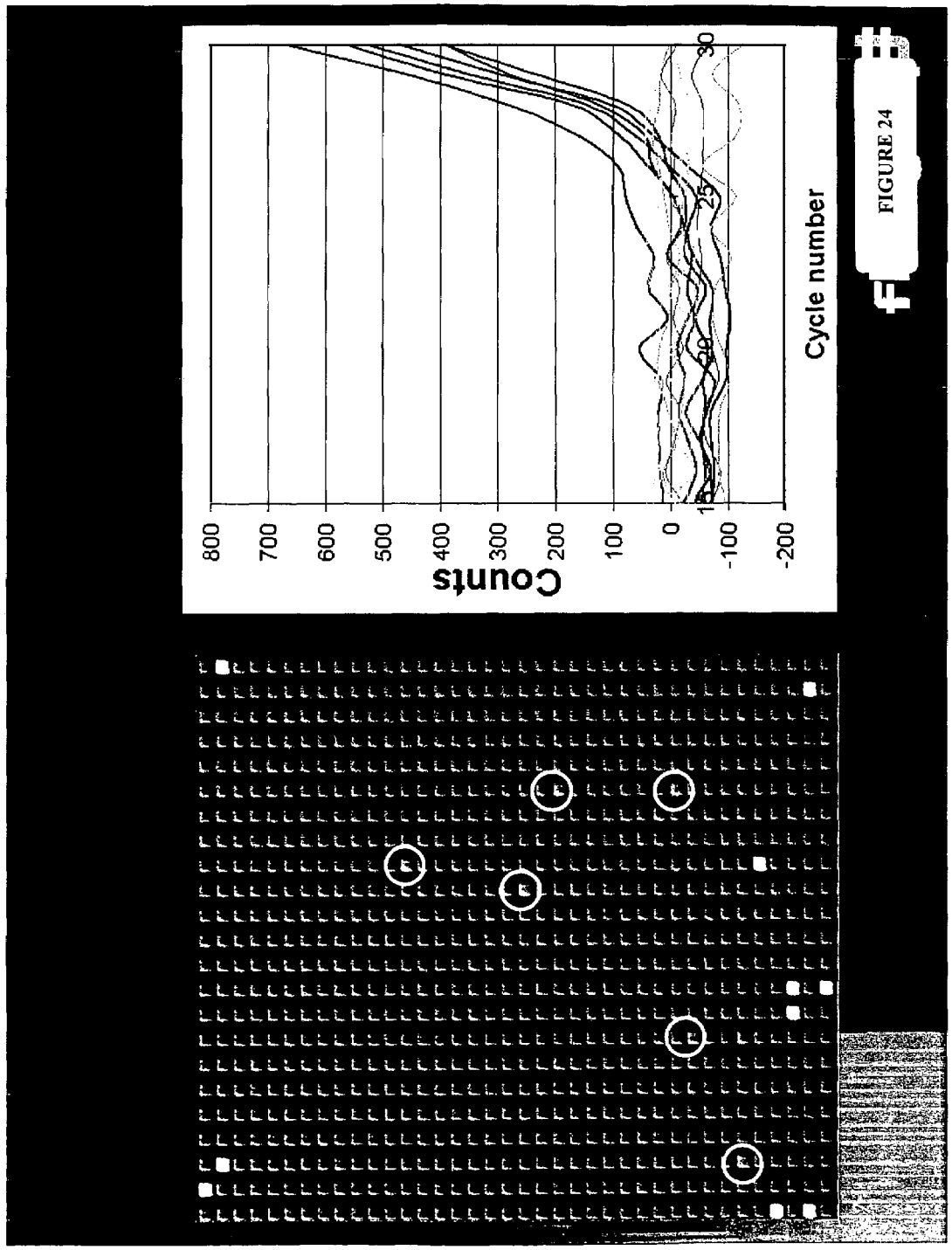
FIG. 24 depicts detection of rare targets among high background genetic material samples.

Scorpion. This method is described, for example, by Thelwell N., et al. Nucleic Acids Research, 28:3752-3761, 2000, which is hereby incorporated by reference in its entirety for all purposes, and which FIG. 20 depicts the scheme thereof, wherein Scorpion probing mechanism is as follows. Step 1: initial denaturation of target and Scorpion stem sequence. Step 2: annealing of Scorpion primer to target. Step 3: extension of Scorpion primer produces double-stranded DNA. Step 4: denaturation of double-stranded DNA produced in step 3. This gives a single-stranded target molecule with the Scorpion primer attached. Step 5: on cooling, the Scorpion probe sequence binds to its target in an intramolecular manner. This is favoured over the intermolecular binding of the complementary target strand A Scorpion (as shown in FIG. 24) consists of a specific probe sequence that is held in a hairpin loop configuration by complementary stem sequences on the 5' and 3' sides of the probe. The fluorophore attached to the 5'-end is quenched by a moiety (normally methyl red) joined to the 3'-end of the loop. The hairpin loop is linked to the 5'-end of a primer via a PCR stopping sequence (stopper). After extension of the primer during PCR amplification, the specific probe sequence is able to bind to its complement within the same strand of DNA. This hybridization event opens the hairpin loop so that fluorescence is no longer quenched and an increase in signal is observed. The PCR stoping sequence prevents read-through, that could lead to opening of the hairpin loop in the absence of the specific target sequence. Such read-through would lead to the detection of non-specific PCR products, e.g. primer dimers or mispriming events.

3. Capacitive DNA Detection

There is a linear relationship between DNA concentration and the change in capacitance that is evoked by the passage of nucleic acids across a 1-kHz electric field. This relationship has been found to be species independent. (See, e.g., Sohn, et al. (2000) Proc. Natl. Acad. Sci. U.S.A. 97:10687-10690). Thus, in certain devices, nucleic acids within the flow channel (e.g., the substantially circular flow channel of FIG. 1 or the reaction chambers of FIG. 2) are subjected to such a field to determine concentration of amplified product. Alternatively, solution containing amplified product is withdrawn and then subjected to the electric field.

IX. Composition of Mixtures for Conducting Reactions

Reactions conducted with the microfluidic devices disclosed herein are typically conducted with certain additives to enhance the reactions. So, for example, in the case of devices in which reagents are deposited, these additives can be spotted with one or more reactants at a reaction site, for instance. One set of additives are blocking reagents that block protein binding sites on the elastomeric substrate. A wide variety of such compounds can be utilized including a number of different proteins (e.g., gelatin and various albumin proteins, such as bovine serum albumin) and glycerol.

A detergent additive can also be useful. Any of a number of different detergents can be utilized. Examples include, but are not limited to SDS and the various Triton detergents.

In the specific case of nucleic acid amplification reactions, a number of different types of additives can be included. One category are enhancers that promote the amplification reaction. Such additives include, but are not limited to, reagents that reduce secondary structure in the nucleic acid (e.g., betaine), and agents that reduce mispriming events (e.g., tetramethylammonium chloride).

It has also been found in conducting certain amplification reactions that some polymerases give enhanced results. For example, while good results were obtained with AmpliTaq Gold polymerase (Applied Biosystems, Foster City, Calif.) from *Thermus aquaticus*, improved reactions were in some instances obtained using DyNAzyme polymerase from Finnzyme, Espoo, Finland. This polymerase is from the thermophilic bacterium, *Thermus brockianus*. Other exemplary polymerases that can be utilized include, but are not limited to, rTH polymerase XL, which is a combination of *Thermus thermophilus* (Tth) and *Thermococcus litoralis* (Tli), hyperthermo-philic archaebacterium *Pyrosoccus woesei* (Pwo), and Tgo DNA Polymerase.

Further details regarding additives useful in conducting reactions with certain of the devices disclosed herein, including nucleic acid amplification reactions, are provided in Example 1 infra.

X. Exemplary Applications

Because the microfluidic devices provided herein can be manufactured to include a large number of reaction sites, the devices are useful in a wide variety of screening and analytical methods. In general, the devices can be utilized to detect reactions between species that react to form a detectable signal, or a product that upon interaction with another species generates a detectable signal. In view of their use with various types of temperature control systems, the devices can also be utilized in a number of different types of analyses or reactions requiring temperature control.

A. Nucleic Acid Amplification Reactions

The devices disclosed herein can be utilized to conduct essentially any type of nucleic acid amplification reaction. Thus, for example, amplification reactions can be linear amplifications, (amplifications with a single primer), as well as exponential amplifications (i.e., amplifications conducted with a forward and reverse primer set).

When the blind channel type devices are utilized to perform nucleic acid amplification reactions, the reagents that are typically deposited within the reaction sites are those reagents necessary to perform the desired type of amplification reaction. Usually this means that some or all of the following are deposited, primers, polymerase, nucleotides, metal ions, buffer, and cofactors, for example. The sample introduced into the reaction site in such cases is the nucleic acid template. Alternatively, however, the template can be deposited and the amplification reagents flowed into the reaction sites. As discussed supra, when the matrix device is utilized to conduct an amplification reaction, samples containing nucleic acid template are flowed through the vertical flow channels and the amplification reagents through the horizontal flow channels or vice versa.

While PCR is perhaps the best known amplification technique. The devices are not limited to conducting PCR amplifications. Other types of amplification reactions that can be conducted include, but are not limited to, (i) ligase chain reaction (LCR) (see Wu and Wallace, *Genomics* 4:560 (1989) and Landegren et al., *Science* 241:1077 (1988)); (ii) transcription amplification (see Kwoh et al., *Proc. Natl. Acad. Sci. USA* 86:1173 (1989)); (iii) self-sustained sequence replication (see Guatelli et al., *Proc. Nat. Acad. Sci. USA*, 87:1874 (1990)); and (iv) nucleic acid based sequence amplification (NASBA) (see, Sooknanan, R. and Malek, L., *BioTechnology* 13:563-65 (1995)). Each of the foregoing references are incorporated herein by reference in their entirety for all purposes.

Detection of the resulting amplified product can be accomplished using any of the detection methods described supra for detecting amplified DNA.

B. SNP Analysis and Genotyping

1. General

Many diseases linked to genome modifications, either of the host organism or of infectious organisms, are the consequence of a change in a small number of nucleotides, frequently involving a change in a single nucleotide. Such single nucleotide changes are referred to as single nucleotide polymorphisms or simply SNPs, and the site at which the SNP occurs is typically referred to as a polymorphic site. The devices described herein can be utilized to determine the identify of a nucleotide present at such polymorphic sites. As an extension of this capability, the devices can be utilized in genotyping analyses. Genotyping involves the determination of whether a diploid organism (i.e., an organism with two copies of each gene) contains two copies of a reference allele (a reference-type homozygote), one copy each of the reference and a variant allele (i.e., a heterozygote), or contains two copies of the variant allele (i.e., a variant-type homozygote). When conducting a genotyping analysis, the methods of the invention can be utilized to interrogate a single variant site. However, as described further below in the section on multiplexing, the methods can also be used to determine the genotype of an individual in many different DNA loci, either on the same gene, different genes or combinations thereof.

Devices to be utilized for conducting genotyping analyses are designed to utilize reaction sites of appropriate size to ensure from a statistical standpoint that a copy of each of the two alleles for a diploid subject are present in the reaction site at a workable DNA concentrations. Otherwise, an analysis could yield results suggesting that a heterozygote is a homozygote simply because a copy of the second allele is not present at the reaction site. Table 2 below indicates the number of copies of the genome present in a 1 nl reaction volume at various exemplary DNA concentrations that can be utilized with the devices described herein.

TABLE 2

Number of genome copies present in a 1 nL volume at the indicated DNA concentration.

| Volume (nL) | [DNA] (ug/uL) | N |
|---|---|---|
| 1 | 0.33 | 100 |
| 1 | 0.10 | 32 |
| 1 | 0.05 | 16 |
| 1 | 0.01 | 3 |
| 1 | 0.003 | 1 |

As a general matter, due to stochastic proportioning of the sample, the copy number present before an amplification reaction is commenced determines the likely error in the measurement. Genotyping analyses using certain devices are typically conducted with samples having a DNA concentration of approximately 0.10 ug/uL, although the current inventors have run successful TaqMan reactions at concentrations in which there is a single genome per reaction site.

2. Methods

Genotyping analyses can be conducted using a variety of different approaches. In these methods, it is generally sufficient to obtain a "yes" or "no" result, i.e., detection need only be able to answer the question whether a given allele is present. Thus, analyses can be conducted only with the primers or nucleotides necessary to detect the presence of one allele potentially at a polymorphic site. However, more typically, primers and nucleotides to detect the presence of each allele potentially at the polymorphic site are included. Examples of suitable approaches follow.

Single Base Pair Extension (SBPE) Reactions. SBPE reactions are one technique specifically developed for conducting genotyping analyses. Although a number of SPBE assays have been developed, the general approach is quite similar. Typically, these assays involve hybridizing a primer that is complementary to a target nucleic acid such that the 3' end of the primer is immediately 5' of the variant site or is adjacent thereto. Extension is conducted in the presence of one or more labeled non-extendible nucleotides that are complementary to the nucleotide(s) that occupy the variant site and a polymerase. The non-extendible nucleotide is a nucleotide analog that prevents further extension by the polymerase once incorporated into the primer. If the added non-extendible nucleotide(s) is(are) complementary to the nucleotide at the variant site, then a labeled non-extendible nucleotide is incorporated onto the 3' end of the primer to generate a labeled extension product. Hence, extended primers provide an indication of which nucleotide is present at the variant site of a target nucleic acid. Such methods and related methods are discussed, for example, in U.S. Pat. Nos. 5,846,710; 6,004,744; 5,888,819; 5,856,092; and 5,710,028; and in WO 92/16657.

Detection of the extended products can be detected utilizing the FRET detection approach described for extension reactions in the detection section supra. Thus, for example, using the devices described herein, a reagent mixture containing a primer labeled with one member of a donor/acceptor fluorophore, one to four labeled non-extendible nucleotides (differentially labeled if more than one non-extendible nucleotide is included), and polymerase are introduced (or previously spotted) at a reaction site. A sample containing template DNA is then introduced into the reaction site to allow template extension to occur. Any extension product formed is detected by the formation of a FRET signal (see, e.g., U.S.

Pat. No. 5,945,283 and PCT Publication WO 97/22719.). The reactions can optionally be thermocycled to increase signal using the temperature control methods and apparatus described above.

Quantitative PCR. Genotyping analyses can also be conducted using the quantitative PCR methods described earlier. In this case, differentially labeled probes complementary to each of the allelic forms are included as reagents, together with primers, nucleotides and polymerase. However, reactions can be conducted with only a single probe, although this can create ambiguity as to whether lack of signal is due to absence of a particular allele or simply a failed reaction. For the typical biallelic case in which two alleles are possible for a polymorphic site, two differentially labeled probes, each perfectly complementary to one of the alleles are usually included in the reagent mixture, together with amplification primers, nucleotides and polymerase. Sample containing the target DNA is introduced into the reaction site. If the allele to which a probe is complementary is present in the target DNA, then amplification occurs, thereby resulting in a detectable signal as described in the detection above. Based upon which of the differential signal is obtained, the identity of the nucleotide at the polymorphic site can be determined. If both signals are detected, then both alleles are present. Thermocycling during the reaction is performed as described in the temperature control section supra.

B. Gene Expression Analysis

1. General

Gene expression analysis involves determining the level at which one or more genes is expressed in a particular cell. The determination can be qualitative, but generally is quantitative. In a differential gene expression analysis, the levels of the gene(s) in one cell (e.g., a test cell) are compared to the expression levels of the same genes in another cell (control cell). A wide variety of such comparisons can be made. Examples include, but are not limited to, a comparison between healthy and diseased cells, between cells from an individual treated with one drug and cells from another untreated individual, between cells exposed to a particular toxicant and cells not exposed, and so on. Genes whose expression levels vary between the test and control cells can serve as markers and/or targets for therapy. For example, if a certain group of genes is found to be up-regulated in diseased cells rather than healthy cells, such genes can serve as markers of the disease and can potentially be utilized as the basis for diagnostic tests. These genes could also be targets. A strategy for treating the disease might include procedures that result in a reduction of expression of the up-regulated genes.

The design of the devices disclosed herein is helpful in facilitating a variety of gene expression analyses. Because the devices contain a large number of reaction sites, a large number of genes and/or samples can be tested at the same time. Using the blind flow channel devices, for instance, the expression levels of hundreds or thousands of genes can be determined at the same time. The devices also facilitate differential gene expression analyses. With the matrix design, for example, a sample obtained from a healthy cell can be tested in one flow channel, with a sample from a diseased cell run in an immediately adjacent channel. This feature enhances the ease of detection and the accuracy of the results because the two samples are run on the same device at the same time and under the same conditions.

2. Sample Preparation and Concentration

To measure the transcription level (and thereby the expression level) of a gene or genes, a nucleic acid sample comprising mRNA transcript(s) of the gene(s) or gene fragments, or nucleic acids derived from the mRNA transcript(s) is obtained. A nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, DNA amplified from the genes, RNA transcribed from amplified DNA.

In some methods, a nucleic acid sample is the total MRNA isolated from a biological sample; in other instances, the nucleic acid sample is the total RNA from a biological sample. The term "biological sample", as used herein, refers to a sample obtained from an organism or from components of an organism, such as cells, biological tissues and fluids. In some methods, the sample is from a human patient. Such samples include sputum, blood, blood cells (e.g., white cells), tissue or fine needle biopsy samples, urine, peritoneal fluid, and fleural fluid, or cells therefrom. Biological samples can also include sections of tissues such as frozen sections taken for histological purposes. Often two samples are provided for purposes of comparison. The samples can be, for example, from different cell or tissue types, from different individuals or from the same original sample subjected to two different treatments (e.g., drug-treated and control).

Any RNA isolation technique that does not select against the isolation of mRNA can be utilized for the purification of such RNA samples. For example, methods of isolation and purification of nucleic acids are described in detail in WO 97/10365, WO 97/27317, Chapter 3 of Laboratory Techniques in Biochemistry and Molecular Biology: Hybridization With Nucleic Acid Probes, Part I. Theory and Nucleic Acid Preparation, (P. Tijssen, ed.) Elsevier, N.Y. (1993); Chapter 3 of Laboratory Techniques in Biochemistry and Molecular Biology: Hybridization With Nucleic Acid Probes, Part 1. Theory and Nucleic Acid Preparation, (P. Tijssen, ed.) Elsevier, N.Y. (1993); and Sambrook et al., Molecular Cloning: A Laboratory Manual, Cold Spring Harbor Press, N.Y., (1989); Current Protocols in Molecular Biology, (Ausubel, F. M. et al., eds.) John Wiley & Sons, Inc., New York (1987-1993). Large numbers of tissue samples can be readily processed using techniques known in the art, including, for example, the single-step RNA isolation process of Chomczynski, P. described in U.S. Pat. No. 4,843,155.

In gene expression analyses utilizing the devices that are described, a significant factor affecting the results is the concentration of the nucleic acid in the sample. At low copy number, noise is related to the square root of copy number. Thus, the level of error that is deemed acceptable governs the copy number required. The required copy number in the particular sample volume gives the required DNA concentration. Although not necessarily optimal, quantitation reactions can be conducted with an error level of up to 50%, but preferably is less. Assuming a 1 nanoliter volume, the DNA concentrations required to achieve a particular error level are shown in Table 3. As can be seen, 1 nanoliter volumes such as used with certain of the devices have sufficient copies of gene expression products at concentrations that are workable with microfluidic devices.

TABLE 3

| | Gene Expression—DNA Quantity | | |
| Error (%) | N (Copy No.) | Volume (nL) | [DNA] ($10^{-12}$ M) |
| --- | --- | --- | --- |
| 2 | 2500 | 1 | 4.2 |
| 10 | 100 | 1 | 0.17 |
| 25 | 16 | 1 | 0.027 |
| 50 | 4 | 1 | 0.0066 |

A further calculation demonstrates that the certain of the devices provided herein which utilize a 1 nanoliter reaction site contain sufficient DNA to achieve accurate expression results. Specifically, a typical mRNA preparation procedure yields approximately 10 ug of mRNA. It has been demonstrated that typically there are 1 to 10,000 copies of each mRNA per cell. Of the mRNAs that are expressed within any given cell, approximately the four most common messages comprise about 13% of the total mRNA levels. Thus, such highly expressed messages comprise 1.3 ug of mRNA (each is $4\times10^{-12}$ mole or approximately $2.4\times10^{12}$ copies). In view of the foregoing expression ranges, rare messages are expected to be present at a level of about $2\times10^{-8}$ copies. If in a standard analysis the mRNA sample is dissolved in 10 ul, the concentration of a rare message is approximately $2\times10^{7}$ copies/ul; this concentration corresponds to 20,000 copies per 1 nl well (or $4\times10^{11}$ M).

3. Methods

Because expression analysis typically involves a quantitative analysis, detection is typically achieved using one of the quantitative real time PCR methods described above. Thus, if a TaqMan approach is utilized, the reagents that are introduced (or previously spotted) in the reaction sites can include one or all of the following: primer, labeled probe, nucleotides and polymerase. If an intercalation dye is utilized, the reagent mixture typically includes one or all of the following: primer, nucleotides, polymerase, and intercalation dye.

D. Multiplexing

The array-based devices described herein (see, e.g., FIGS. 1A, 1F, 2, 3A and 3B and accompanying text) are inherently designed to conduct a large number of amplification reactions at the same time. This feature, however, can readily be further expanded upon by conducting multiple analyses (e.g., genotyping and expression analyses) within each reaction site.

Multiplex amplifications can even be performed within a single reaction site by, for example, utilizing a plurality of primers, each specific for a particular target nucleic acid of interest, during the thermal cycling process. The presence of the different amplified products can be detected using differentially labeled probes to conduct a quantitative RT-PCR reaction or by using differentially labeled molecular beacons (see supra). In such approaches, each differentially labeled probes is designed to hybridize only to a particular amplified target. By judicious choice of the different labels that are utilized, analyses can be conducted in which the different labels are excited and/or detected at different wavelengths in a single reaction. Further guidance regarding the selection of appropriate fluorescent labels that are suitable in such approaches include: *Fluorescence Spectroscopy* (Pesce et al., Eds.) Marcel Dekker, New York, (1971); White et al., *Fluorescence Analysis: A Practical Approach*, Marcel Dekker, New York, (1970); Berlman, *Handbook of Fluorescence Spectra of Aromatic Molecules*, $2^{nd}$ ed., Academic Press, New York, (1971); Griffiths, *Colour and Constitution of Organic Molecules*, Academic Press, New York, (1976); *Indicators* (Bishop, Ed.). Pergamon Press, Oxford, 19723; and Haugland, *Handbook of Fluorescent Probes and Research Chemicals*, Molecular Probes, Eugene (1992).

Multiple genotyping and expression analyses can optionally be conducted at each reaction site. If quantitative PCR methods such as TaqMan is utilized, then primers for amplifying different regions of a target DNA of interest are included within a single reaction site. Differentially labeled probes for each region are utilized to distinguish product that is formed.

E. Non-Nucleic Acid Analyses

While useful for conducting a wide variety of nucleic acid analyses, the devices can also be utilized in a number of other applications as well. As indicated earlier, the devices can be utilized to analyze essentially any interaction between two or more species that generates a detectable signal or a reaction product that can reacted with a detection reagent that generates a signal upon interaction with the reaction product.

Thus, for example, the devices can be utilized in a number of screening applications to identify test agents that have a particular desired activity. As a specific example, the devices can be utilized to screen compounds for activity as a substrate or inhibitor of one or more enzymes. In such analyses, test compound and other necessary enzymatic assay reagents (e.g., buffer, metal ions, cofactors and substrates) are introduced (if not previously deposited) in the reaction site. The enzyme sample is then introduced and reaction (if the test compound is a substrate) or inhibition of the reaction (if the test compound is an inhibitor) is detected. Such reactions or inhibition can be accomplished by standard techniques, such as directly or indirectly monitoring the loss of substrate and/or appearance of product.

Devices with sufficiently large flow channels and reaction sites can also be utilized to conduct cellular assays to detect interaction between a cell and one or more reagents. For instance, certain analyses involve determination of whether a particular cell type is present in a sample. One example for accomplishing this is to utilize cell-specific dyes that preferentially reaction with certain cell types. Thus, such dyes can be introduced into the reaction sites and then cells added. Staining of cells can be detected using standard microscopic techniques. As another illustration, test compounds can be screened for ability to trigger or inhibit a cellular response, such as a signal transduction pathway. In such an analysis, test compound is introduced into a site and then the cell added. The reaction site is then checked to detect formation of the cellular response.

Further discussion of related devices and applications of such devices is set forth in copending and commonly owned U.S. Provisional application Ser. No. 60/335,292, filed Nov. 30, 2001, which is incorporated herein by reference in its entirety for all purposes.

XI. Fabrication

A. General Aspects

As alluded to earlier, the microfluidic devices that are provided are generally constructed utilizing single and multilayer soft lithography (MSL) techniques and/or sacrificial-layer encapsulation methods. The basic MSL approach involves casting a series of elastomeric layers on a micro-machined mold, removing the layers from the mold and then fusing the layers together. In the sacrificial-layer encapsulation approach, patterns of photoresist are deposited wherever a channel is desired. These techniques and their use in producing microfluidic devices is discussed in detail, for example, by Unger et al. (2000) Science 288:113-116, by Chou, et al. (2000) "Integrated Elastomer Fluidic Lab-on-a-chip-Surface Patterning and DNA Diagnostics, in Proceedings of the Solid State Actuator and Sensor Workshop, Hilton Head, S.C.; and in PCT Publication WO 01/01025, each of which is incorporated herein by reference in their entirety for all purposes.

In brief, the foregoing fabrication methods initially involve fabricating mother molds for top layers (e.g., the elastomeric layer with the control channels) and bottom layers (e.g., the elastomeric layer with the flow channels) on silicon wafers by photolithography with photoresist (Shipley SJR 5740). Channel heights can be controlled precisely by the spin coating rate. Photoresist channels are formed by exposing the photoresist to UV light followed by development. Heat reflow process and protection treatment is typically achieved as described by M. A. Unger, H. -P. Chou, T. Throsen, A. Scherer and S. R. Quake, Science (2000) 288:113, which is incorporated herein by reference in its entirety. A mixed two-part-silicone elastomer (GE RTV 615) is then spun into the bottom mold and poured onto the top mold, respectively. Here, too, spin coating can be utilized to control the thickness of bottom polymeric fluid layer. The partially cured top layer is peeled off from its mold after baking in the oven at 80° C. for 25 minutes, aligned and assembled with the bottom layer. A 1.5-hour final bake at 80° C. is used to bind these two layers irreversibly. Once peeled off from the bottom silicon mother mold, this RTV device is typically treated with HCL (0.1N, 30 min at 80° C.). This treatment acts to cleave some of the Si—O—Si bonds, thereby exposing hydroxy groups that make the channels more hydrophilic.

The device can then optionally be hermetically sealed to a support. The support can be manufactured of essentially any material, although the surface should be flat to ensure a good seal, as the seal formed is primarily due to adhesive forces. Examples of suitable supports include glass, plastics and the like.

The devices formed according to the foregoing method result in the substrate (e.g., glass slide) forming one wall of the flow channel. Alternatively, the device once removed from the mother mold is sealed to a thin elastomeric membrane such that the flow channel is totally enclosed in elastomeric material. The resulting elastomeric device can then optionally be joined to a substrate support.

B. Devices Utilizing Blind Channel Design

1. Layer Formation

Microfluidic devices based on the blind channel design in which reagents are deposited at the reaction sites during manufacture are typically formed of three layers. The bottom layer is the layer upon which reagents are deposited. The bottom layer can be formed from various elastomeric materials as described in the references cited above on MLS methods. Typically, the material is polydimethylsiloxane (PMDS) elastomer. Based upon the arrangement and location of the reaction sites that is desired for the particular device, one can determine the locations on the bottom layer at which the appropriate reagents should be spotted. Because PMDS is hydrophobic, the deposited aqueous spot shrinks to form a very small spot. The deposited reagents are deposited such that a covalent bond is not formed between the reagent and the surface of the elastomer because, as described earlier, the reagents are intended to dissolve in the sample solution once it is introduced into the reaction site.

The other two layers of the device are the layer in which the flow channels are formed and the layer in which the control and optionally guard channels are formed. These two layers are prepared according to the general methods set forth earlier in this section. The resulting two layer structure is then placed on top of the first layer onto which the reagents have been deposited. A specific example of the composition of the three layers is as follows (ration of component A to component B): first layer (sample layer) 30:1 (by weight); second layer (flow channel layer) 30:1; and third layer (control layer) 4:1. It is anticipated, however, that other compositions and ratios of the elastomeric components can be utilized as well.

Figure 6:
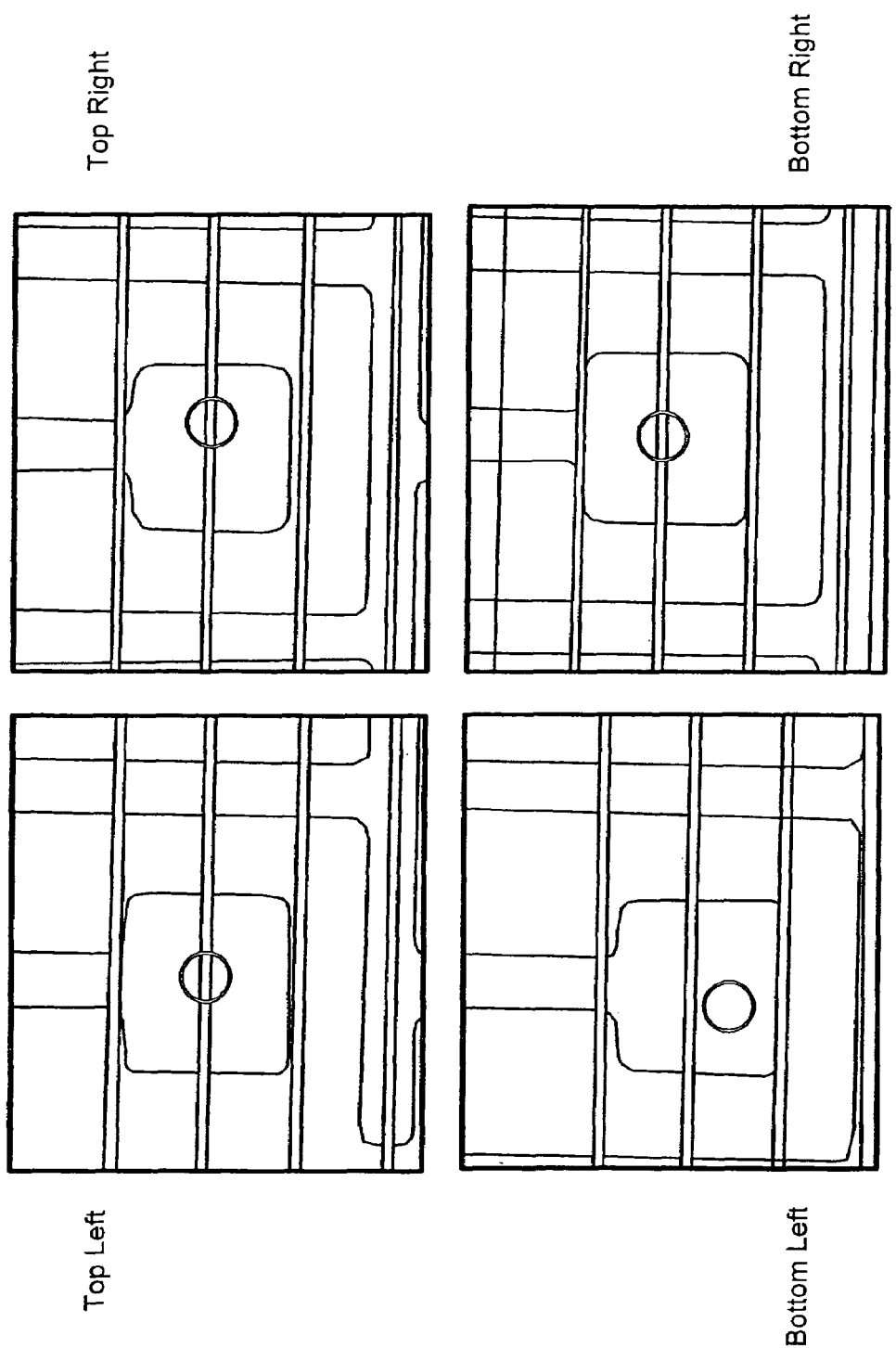
FIG. 6 shows the location of spotted reagents within reaction sites in a blind channel type device illustrating proper alignment of the reagents within reaction sites at the corners of the device.

During this process, the reaction sites are aligned with the deposited reagents such that the reagents are positioned within the appropriate reaction site. FIG. 6 is a set of photographs taken from the four corners of a device; these photographs demonstrate that the deposited reagents can be accurately aligned within the reaction sites utilizing the foregoing approach. These photographs show guard channels and reaction site located at the end of branch flow channel. The white circle indicates the location of the deposited reagent relative to the reaction site. As indicated, each reagent spot is well within the confines of the reaction site.

2. Spotting

The reagents can be deposited utilizing any of a number of commercially available reagent spotters and using a variety of established spotting techniques. Examples of suitable spotter that can be utilized in the preparation of the devices include pin spotters, acoustic spotters, automated micropipettors, electrophoretic pumps, ink jet printer devices, ink drop printers, and certain osmotic pumps. Examples of commercially available spotters include: Cartesian Technologies MicroSys 5100 (Irvine, Calif.), Hitach SPBIO (Alameda, Calif.), Genetix Q-Array (United Kingdom), Affymetrix 417 (Santa Clara, Calif.) and Packard Bioscience SpotArray (Meriden, Conn.). In general, very small spots of reagents are deposited; usually spots of less than 10 nl are deposited, in other instances less than 5 nl, 2 nl or 1 nl, and in still other instances, less than 0.5 nl, 0.25 nl, or 0.1 nl.

Arrays of materials may also be formed by the methods described in Foder, et al., U.S. Pat. No. 5,445,934:titled "Array of oligonucleotides on a solid substrate", which is herein incorporated by reference, wherein oligonucleotide probes, such as SNP probes, are synthesized in situ using spatial light directed photolithography. Such arrays would be used as the substrate or base of the microfluidic devices of the present invention such that the regions of the substrate corresponding to the reaction sites, for example, blind fill chambers, would be contain one, or preferably more than one, oligonucleotide probes arrayed in known locations on the substrate. In the case of a partitioning microfluidic structure, such as the one depicted in FIG. 15 herein, the reaction sites, depicted as square boxes along the serpentine, fluid channel, would contain a plurality of different SNP probes, preferably a collection of SNP probes suitable for identifying an individual from a population of individuals, and preferably wherein a plurality of reaction sites along the serpentine fluid channel, such that if a fluid sample containing nucleic acid sequences from a plurality of individuals where introduced into the serpentine flow channel, and a plurality of valve in communication with the serpentine flow channel such that when actuated causes the serpentine flow channel to be partitioned thereby isolating each reaction site from one another to contain a fraction of the fluid sample in each reaction site. Amplification of the components of the sample may be performed to increase the number of molecules, for example nucleic acid molecules, for binding to the array of SNP probes located within each reaction site. In some embodiments, each of the reaction sites along the serpentine fluid channel would be the same array, that is, have the same SNP probes arrayed, and in other embodiments, two or more of the reaction sites along the serpentine t fluid channel would have a different set of SNP probes. Other partitioning fluid channel architectures could also be used, for example, branched and/or branched branch systems, and so forth. Other arraying techniques, such as spotting described herein, may likewise be used to form the arrays located within the partitionable reactions sites along a serpentine or common, such as in branched, fluid channel(s).

The following examples are presented to further illustrate certain aspects of the devices and methods that are disclosed herein. The examples are not to be considered as limiting the invention.

EXAMPLE 1

Signal Strength Evaluations

I. Introduction

The purpose of this set of experiments was to demonstrate that successful PCR reactions can be conducted with a microfluidic device of the design set forth herein with signal strength greater than 50% of the Macro TaqMan reaction.

II. Microfluidic Device

Figure 7A:
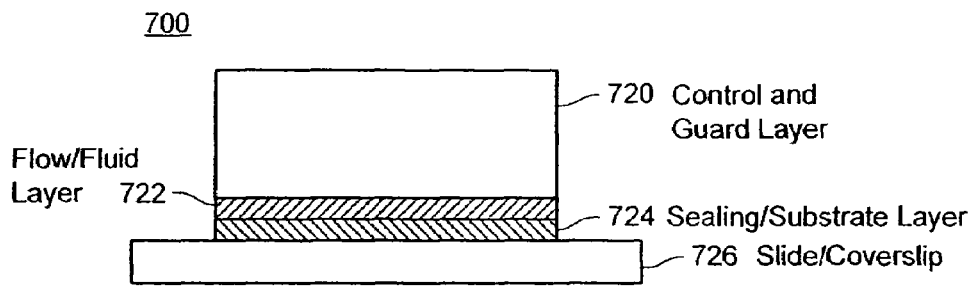
FIGS. 7A and 7B respectively are a cross-sectional view and a schematic diagram of another hybrid type microfluidic device and represents the type of device used to conduct the experiments described in Examples 1-4.

A three layer microfluidic device, fabricated using the MSL process, was designed and fabricated for conducting the experiments described in the following example. FIG. 7A shows a cross-sectional view of the device. As shown, the device 700 includes a layer 722 into which is formed the flow channels. This fluid layer 722 is sandwiched between an overlaying layer 720 that includes the control and guard layers and an underlying sealing layer 724. The sealing layer 724 forms one side of the flow channels. The resulting three-layer structure is affixed to a substrate 726 (in this example, a slide or coverslip), which provides structural stiffness, increases thermal conductivity, and helps to prevent evaporation from the bottom of microfluidic device 700.

Figure 7B:
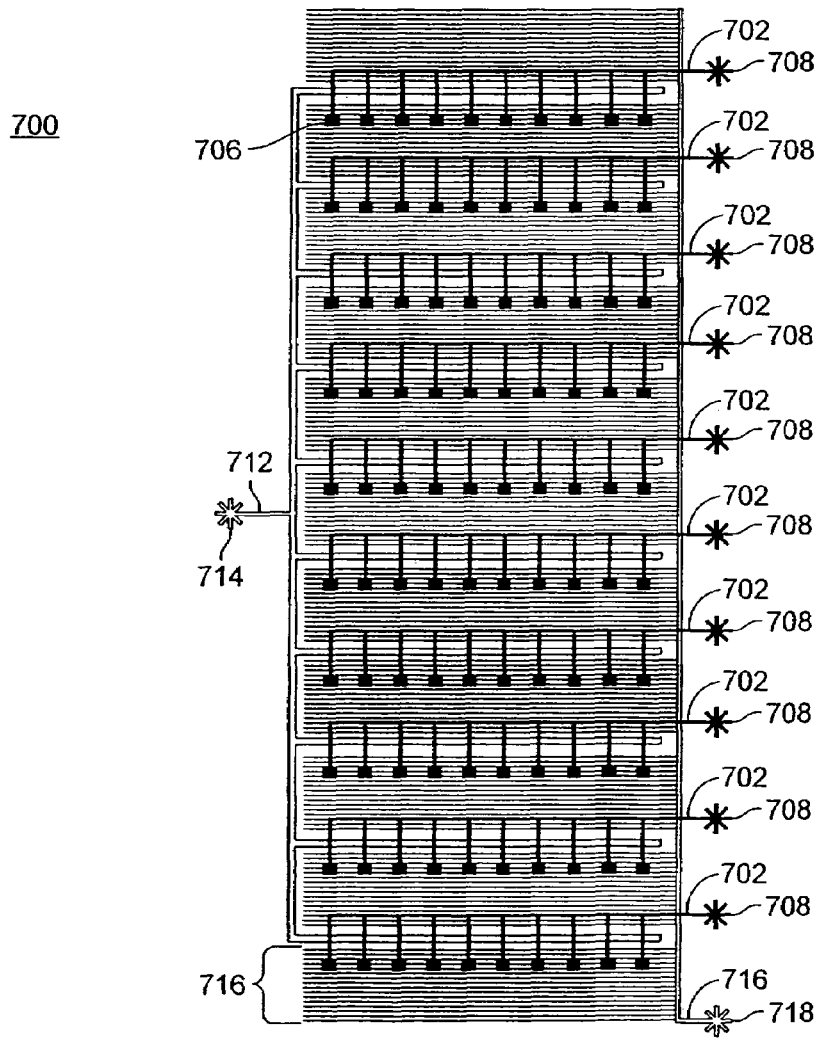

FIG. 7B shows a schematic view of the design of the flow channels in flow layer 722 and of the control channels and guard channel in control/guard layer 720. Device 700 consists of ten independent flow channels 702, each with its own inlet 708, and branching blind channels 704, each blind channel 704 having a 1 nl reaction site 706. Device 700 contains a network of control lines 712, which isolate the reaction sites 706 when sufficient pressure is applied. A series of guard channels 716 are also included to prevent liquid from evaporating out of the reaction sites 706; fluid is introduced via inlet 718.

II. Experimental Setup

A PCR reaction using β-actin primers and TaqMan probe to amplify exon 3 of the β-actin gene from human male genomic DNA (Promega, Madison Wis.) was conducted in device 700. The TaqMan reaction consists of the following components: lx TaqMan Buffer A (50 mM KCl, 10 mM Tris-HCl, 0.01M EDTA, 60 nM Passive Reference 1 (PR1), pH 8.3); 3.5-4.0 mM MgCl; 200 nM dATP, dCTP, dGTP, 400 nM dUTP; 300 nM β-actin forward primer and reverse primer; 200 nM FAM-labeled β-actin probe; 0.01 U/ul AmpEraseUNG (Applied Biosystems, Foster City, Calif.); 0.1-0.2U/ul DyNAzyme (Finnzyme, Espoo, Finland); 0.5%Triton-x-100 (Sigma, St. Louis, Mo.); 0.8 ug/ul Gelatin (Calbiochem, San Diego, Calif.); 5.0% Glycerol (Sigma, St. Louis, Mo.); deionized $H_2O$ and male genomic DNA. The components of the reaction were added to produce a total reaction volume of 25 μl. Negative controls (Control) composed of all the TaqMan reaction components, except target DNA were included in each set of PCR reactions.

Once the TaqMan reaction samples and Control were prepared, they were injected into microfluidic device 700 by using a gel loading pipet tip attached to a 1 ml syringe. The pipet tip was filled with the reaction samples and then inserted into the fluid via 708. The flow channels 702 were filled by manually applying backpressure to the syringe until all the entire blind channels 704 and reaction sites 706 were filled. Control lines 712 were filled with deionized water and pressurized to 15-20 psi after all of the samples were loaded into the flow lines 702, 704. The pressurized control lines 712 were actuated to close the valves and isolate the samples in the 1 nl wells 706. The guard channels 716 were then filled with deionized water and pressurized to 5-7 psi. Mineral oil (15 ul) (Sigma) was placed on the flatplate of a thermocycler and then the microfluidic device/coverglass 700 was placed on the thermocycler. Micro fluidic device 700 was then thermocycled using an initial ramp and either a three-step or two-step thermocycling profile:

1. Initial ramp to 95° C. and maintain for 1 minute (1.0° C./s to 75° C., 0.1° C./sec to 95° C.).
2. Three step thermocycling for 40 cycles (92° C. for 30 sec., 54° C. for 30 sec., and 72° C. for 1 min) or;
3. Two step thermocycling for 40 cycles (92° C. for 30 seconds and 60° C. for 60 sec.)

MicroAmp tubes (Applied Biosystems, Foster City, Calif.) with the remaining reaction mixture, designated Macro TaqMan reactions to distinguish them from reactions performed in the microfluidic device, were placed in the GeneAmp PCR System 9700 (Applied Biosystems, Foster City, Calif.) and thermocycled in the 9600 mode. The Macro TaqMan reactions served as macroscopic controls for the reactions performed in the micro fluidic device. The thermocycling protocol was set to match that of the microfluidic device, except that the initial ramp rate was not controlled for the Macro TaqMan reactions.

Once thermocycling was completed, the control and guard lines were depressurized and the chip was transferred onto a glass slide (VWR, West Chester, Pa.). The chip was then placed into an Array WoRx Scanner (Applied Precision, Issaquah, Wash.) with a modified carrier. The fluorescence intensity was measured for three different excitation/emission wavelengths: 475/510 nm (FAM), 510/560 nm (VIC), and 580/640 nm (Passive Referencel (PR1)). The Array Works Software was used to image the fluorescence in the micro fluidic device and to measure the signal and background intensities of each 1 nl well. The results were then analyzed using a Microsoft Excel file to calculate the FAM/PR1 ratio for β-actin TaqMan reactions. For conventional Macro TaqMan, positive samples for target DNA were determined using calculations described in the protocol provided by the manufacturer (TaqMan PCR Reagent Kit Protocol). The signal strength was calculated by dividing the FAM/PR1 ratio of the samples by the FAM/PR1 ratio of the controls. A successful reaction was defined as a sample ratio above the 99% confidence threshold level.

III. Results

Figure 8:
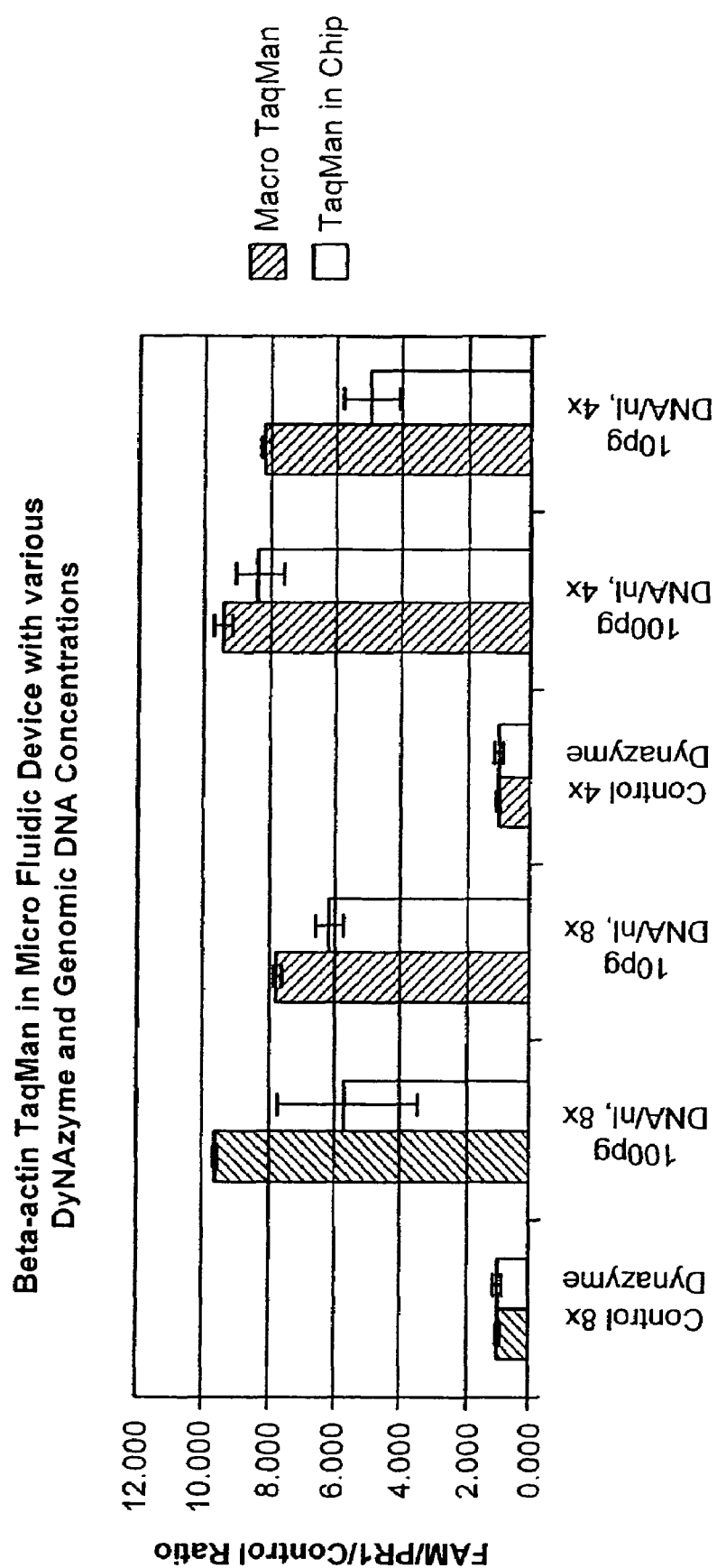
FIG. 8 is a bar graph in which the average FAM/PRI/Control ratios are plotted for six different β-actin TaqMan reactions. The reactions were thermocycled in the micro fluidic device (chip) shown in FIG. 7B (solid bars) and Macro TaqMan reactions (striped bars). The controls are the first and fourth bar sets that have no DNA. The error bars are the standard deviation of the ratios.

Initially, AmpliTaq Gold (Applied Biosystems, Foster City, Calif.) was used in TaqMan reactions and FAM/PR1/Control ratios of 1.5-2.0 were produced, compared to Macro TaqMan reaction ratios of 5.0-14.0. Although results were positive, increased signal strength was desired. Therefore, the AmpliTaq Gold polymerase was substituted with DyNAzyme polymerase due to its increased thermostability, proofreading, and resistance to impurities. The standard Macro TaqMan DyNAzyme concentration of 0.025 U/ul was used in the microfluidic experiments. This polymerase change to DyNAzyme produced FAM/ROX/Control ratios of 3.5-5.8. The signal strength was improved, but it was difficult to achieve consistent results. Because it is know that some proteins stick to PDMS, the concentration of the polymerase was increased and surface modifying additives were included. Two increased concentrations of DyNAzyme were tested, 8× (0.2 U/ul) and 4× (0.1 U/ul) the standard concentration for Macro TaqMan, with 100 μg or 10 μg of genomic DNA per nl in the micro fluidic device. Gelatin, Glycerol, and 0.5%Triton-x-100 were added to prevent the polymerase from attaching to the PDMS. The results of the reactions in the micro fluidic device (chip) and the Macro TaqMan controls are shown in FIG. 8.

The microfluidic TaqMan reaction ratios range from 4.9-8.3, while the Macro TaqMan reactions range from 7.7-9.7. Therefore, the signal strength of the TaqMan reactions in chip is up to 87% of the Macro TaqMan reactions. There was no significant difference between 4× or 8× DyNAzyme. The results demonstrate that PCR reactions can be done with greater than 50% signal strength, when compared to the Macro TaqMan reactions, in the microfluidic devices. The results have been consistent through at least four attempts.

EXAMPLE 2

Spotting Reagents

I. Introduction

The purpose of the experiment was to demonstrate successful spotted PCR reactions in a microfluidic device. The term "spotted" in this context, refers to the placement of small droplets of reagents (spots) on a substrate that is then assembled to become part of a microfluidic device. The spotted reagents are generally a subset of the reagent mixture required for performing PCR.

II. Procedure

A. Spotting of Reagents

Figure 9:
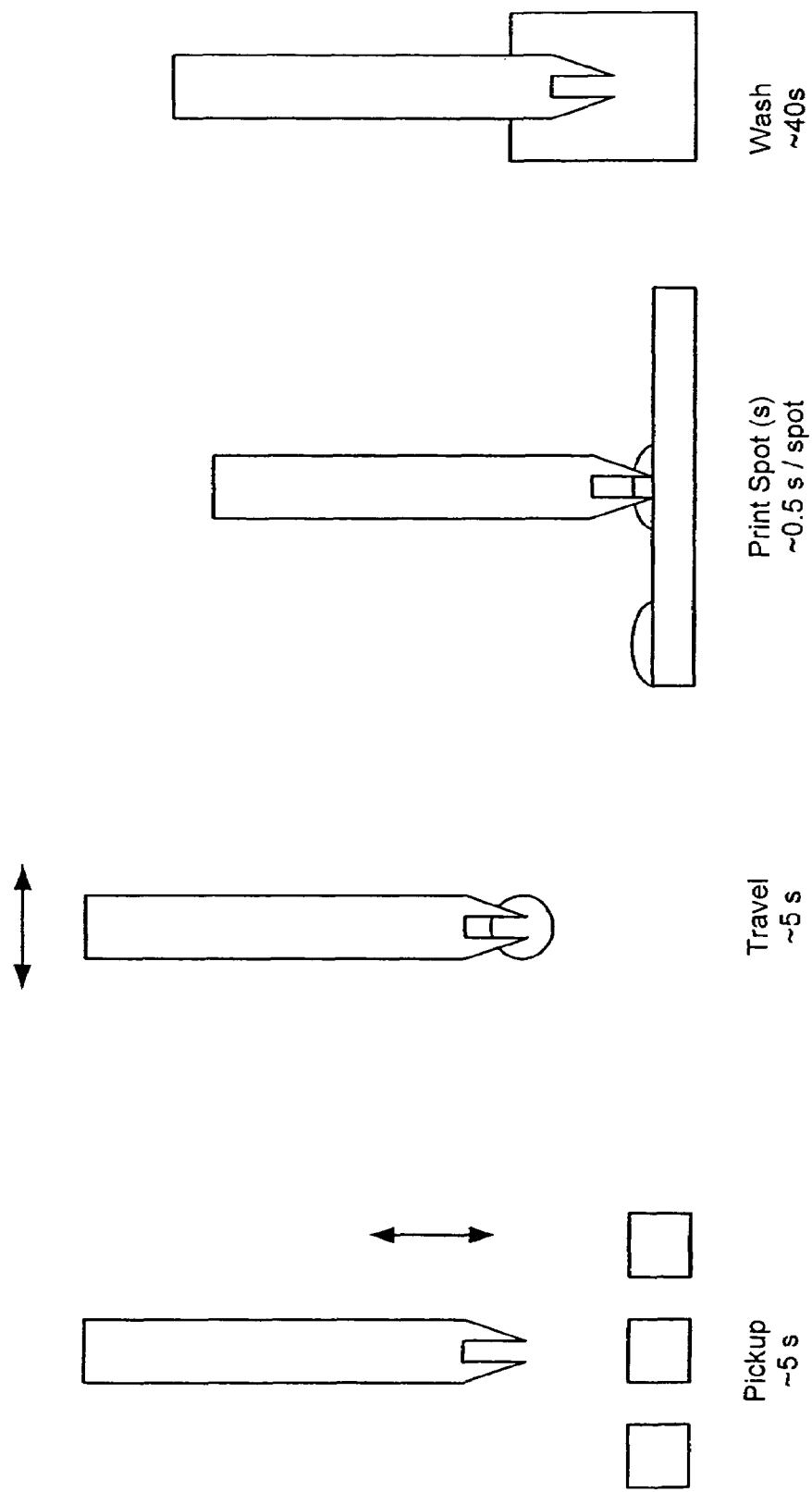
FIG. 9 is a diagram depicting an exemplary pin spotting process. Reagents are picked up from a source (e.g., a microtiter plate) and then printed by bringing the loaded pin into contact with the substrate. The wash step consists of agitation in deionized water followed by vacuum drying.

Routine spotting of reagents was performed via a contact printing process. Reagents were picked up from a set of source wells on metal pins, and deposited by contacting the pins to a target substrate. This printing process is further outlined in FIG. 9. As shown, reagents were picked up from a source (e.g., microtiter plates), and then printed by bringing the loaded pin into contact with the substrate. The wash step consists of agitation in deionized water followed by vacuum drying. The system used to print the reagent spots is a Cartesian Technologies MicroSys 5100 (Irvine, Calif.), employing TeleChem "ChipMaker" brand pins, although other systems can be used as described supra.

Pins employed are Telechem ChipMaker 4 pins, which incorporate an electro-milled slot (see FIG. 9) to increase the uptake volume (and hence the number of printable spots). Under the operating conditions employed (typically, 75% relative humidity and temperature approximately 25° C.), in excess of one hundred spots were printed per pin, per loading cycle. Under the conditions above, the volume of reagents spotted onto the PDMS substrate is on the order of 0.1 nL.

The dimensions of the pin tip are 125×125 μm. The final spot of dried reagent is substantially smaller than this (as small as 7 μm in diameter), yet the pin size defines a lower limit to the readily achievable spot spacing. The achievable spacing determines the smallest well-to-well pitch in the final device. Using such a device and the foregoing methods, arrays with spacings of 180 μm have been achieved. Arrays built into working chips tend to have spacings from 600 to 1300 microns.

Spotting was done using only one pin at a time. The system in use, however, has a pin head which can accommodate up to 32 pins. Printing a standard-size chip (array dimensions of order 20×25 mm) takes under 5 minutes.

B. Assembly of Spotted Chips

The flow and control layers of the PCR devices are assembled according to the normal MSL process described above. The microfluidic device design is the same as the one described in Example 1. In parallel, a substrate layer composed of 150 μm -thick PDMS with component ratio A:B of 30:1 is formed via spin-coating a blank silicon wafer, and then cured for 90 minutes at 80° C.

The cured blank substrate layer of PDMS (sealing/substrate layer 724 of FIG. 7A) serves as the target for reagent spotting. Patterns of spots are printed onto the substrate, which is still on the blank wafer. The reagents spotted for PCR reactions were primers and probes, specific to the particular gene to be amplified.

The spotted reagent included a 1:1:1 volume ratio of 300 nM β-actin forward primer (FP), 300 nM β-actin reverse primer (RP), and 200 nM β-actin probe (Prb). In some cases, it is useful to further tune the chemistry via concentrating the spotted mixture.

It has been found that adjusting the concentrations such that primer and probe concentrations are equal to, or slightly higher than, the normal macroscopic recipe value yields consistently good results. Therefore, the spotted reagent is concentrated to be 3 times and 4 times the concentration of the macro reaction. Concentration of the reagents is performed in a Centrivap heated and evacuated centrifuge and does not alter relative FP:RP:Prb ratios. The increased spot concentration results in the correct final concentration when the reagents are resuspended in a 1 nL reaction volume. Spotted reagents need not be limited to primers and probes; nor must all three (FP, RP and Prb) be spotted. Applications where only the probe, or even one of the primers, is spotted can be performed. Experiments have been conducted in which the sample primer/probe sets spotted were TaqMan β-actin and TaqMan RNAse-P.

Following the spotting process onto the substrate layer, the combined flow and control layers (i.e., layers 720 and 722 of FIG. 7A) were aligned with the spot pattern and brought into contact. A further bake at 80° C., for 60-90 minutes, was used to bond the substrate to the rest of the chip. After the chip has been assembled, the remaining components of the PCR reaction (described in Example 1) are injected into the flow channels of the chip and the chip is thermocycled as described in Example 1.

III. Results

Figure 10:
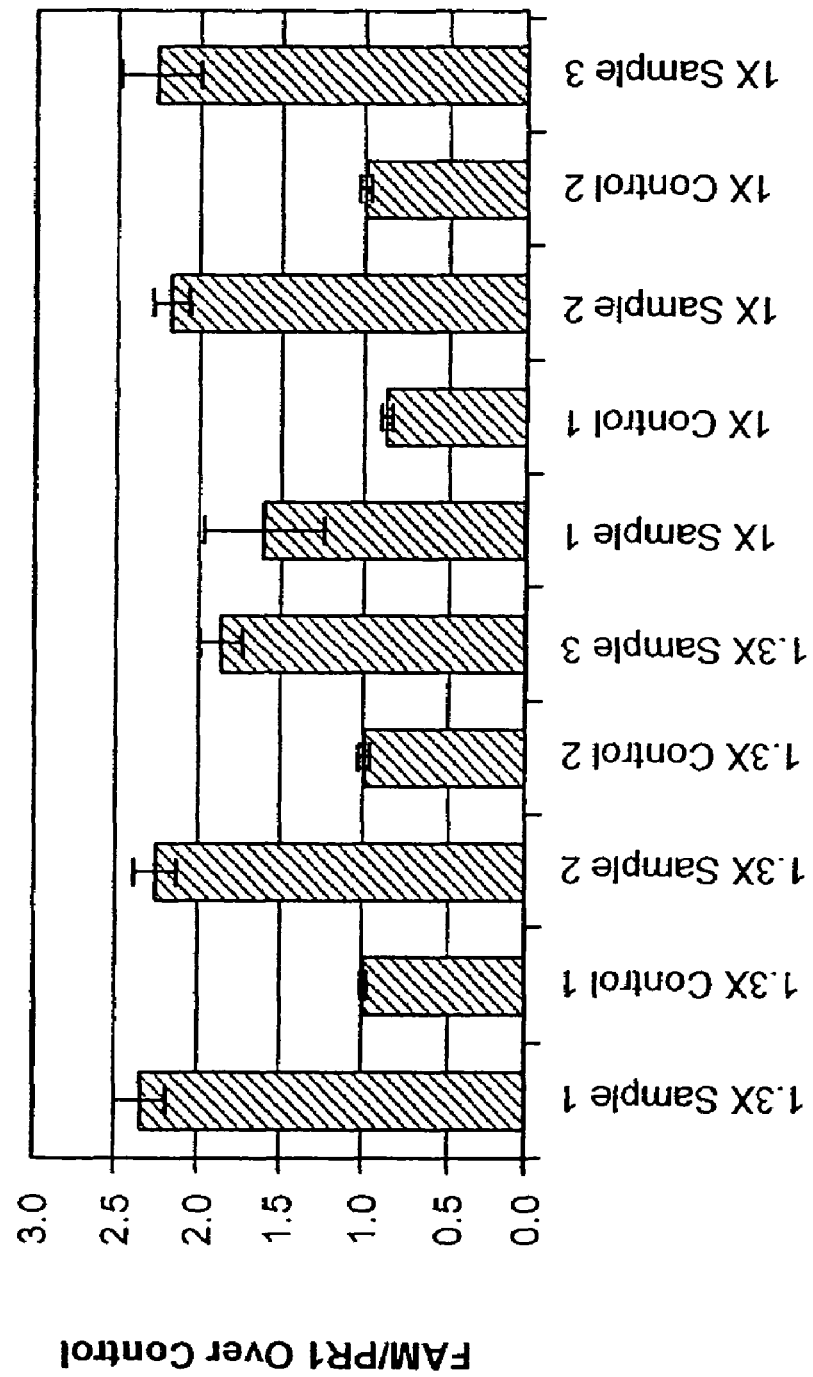
FIG. 10 is a bar graph depicting FAM signal strength for the microfluidic device (chip) described in Example 1 (see FIG. 7B) based on the experiments described in Example 2. The data are in the form of (FAM signal/PRI signal) scaled by the FAM/PRI ratio for the reference lanes. Error bars are the standard deviation along a lane. The "1.3×" and "1×" designations refer to the concentration of the spotted primers and probes, in relation to their nominal values.

PCR reactions have been successfully and repeatably performed using devices where primer (forward and reverse primers) and probe molecules are spotted. An example of data from a chip in which a reaction has been successfully performed is shown in FIG. 10. The spotted reagents have resulted in successful PCR reactions as defined in Example 1. Successful reactions have been performed using 2-stage and 3-stage thermocycling protocols.

EXAMPLE 3

Genotyping

I. Introduction

The purpose of the following experiments was to demonstrate that genotyping experiments can be conducted utilizing a microfluidic device or chip such as described herein. Specifically, these experiments were designed to determine if reactions conducted in the device have sufficient sensitivity and to ensure that other primer/probe sets, besides β-actin, can be performed in the microfluidic device.

II. Methods/Results

A. RNase P Experiment

Figure 11:
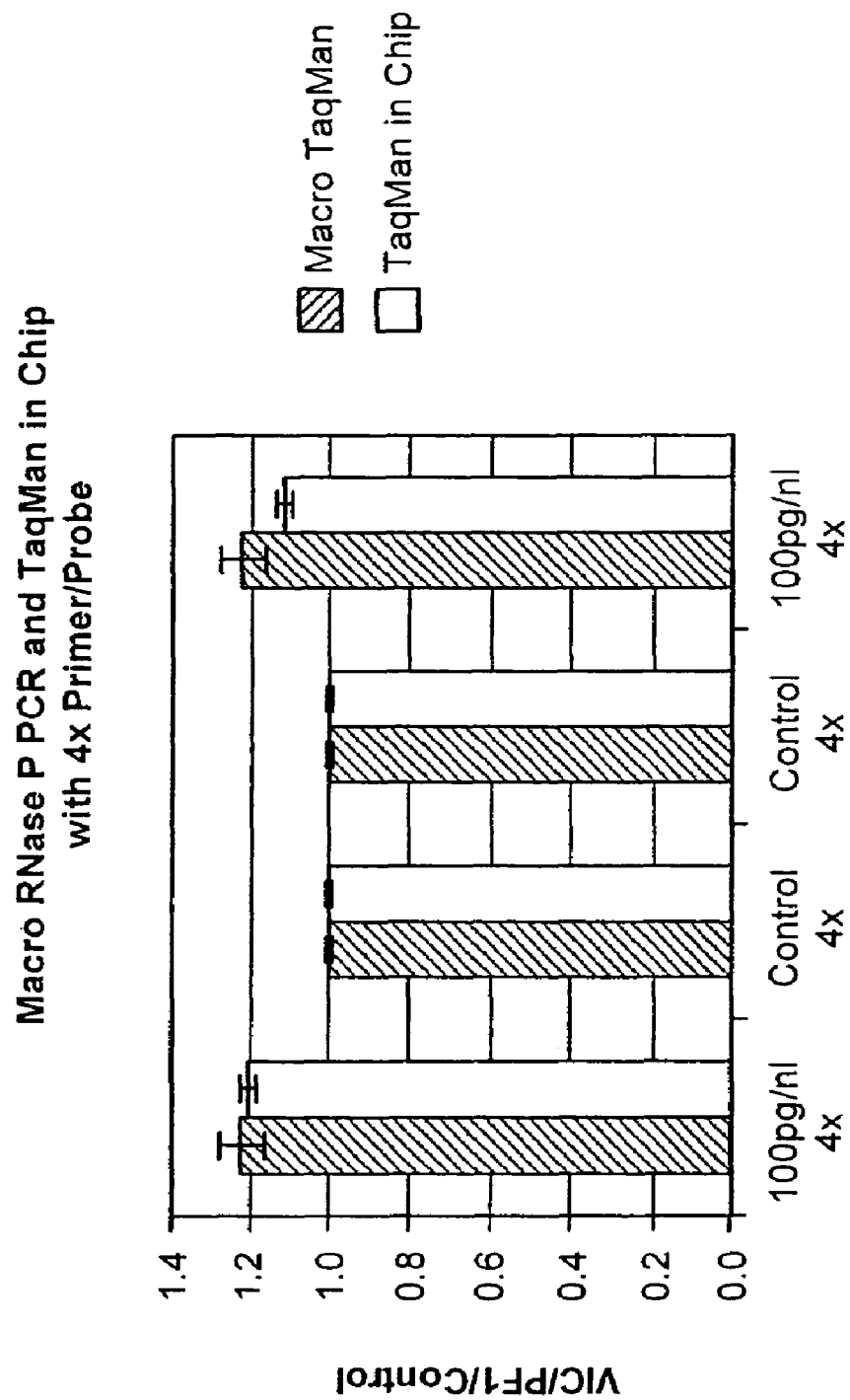
FIG. 11 is a bar graph showing average VIC/PF1/Control ratios for 9-10 wells for Macro TaqMan (striped bars), and TaqMan reactions in the microfluidic device (solid bars). Two negative controls (Control) and two samples with 100 pg/nl genomic DNA were thermocycled with reaction components as described above with 4× the standard amount of primer/probe. The error bars represent the standard deviation of the average ratios.

RNase P TaqMan reactions (Applied Biosystems; Foster City, Calif.) were performed in a microfluidic device as described in Example 1 to demonstrate that other primer/probe sets produce detectable results. RNaseP reactions also require a higher level of sensitivity because the RNaseP primer/probe set detects a single copy gene (2 copies/genome) in contrast to the β-actin primer/probe set. The β-actin set detects a single copy β-actin gene and several pseudogenes, which collectively total approximately 17 copies per genome. The RNase P reactions were run with the same components as described in Example 1, with the exception that the β-actin primer/probe set was replaced with the RNase P primer/probe set. Further, the RnaseP primer/probe set was used at 4x the manufacturer's recommended value to enhance the fluorescence signal. The VIC dye was conjugated to the probe for RNase P and the analysis focused on VIC/PRI ratios. The results of one of four experiments are shown in FIG. 11.

The VIC/PR1/Control ratios for the Macro TaqMan reactions are 1.23. The corresponding ratios for the TaqMan reactions in the microfluidic device are 1.11 and 1.21. The ratios of the genomic DNA samples in the microfluidic device are above the 99% confidence threshold level. Further, the signal strength of the TaqMan reactions in the microfluidic device is 50% and 93.7% of the Macro TaqMan reactions. The control TaqMan reactions in the microfluidic device have standard deviations of 0.006 and 0.012, demonstrating consistency in the reactions across the micro fluidic device. Therefore, it is determined that the TaqMan reactions in the chip are sensitive enough to detect 2 copies per genome.

B. DNA Dilution Experiment

Figure 12:
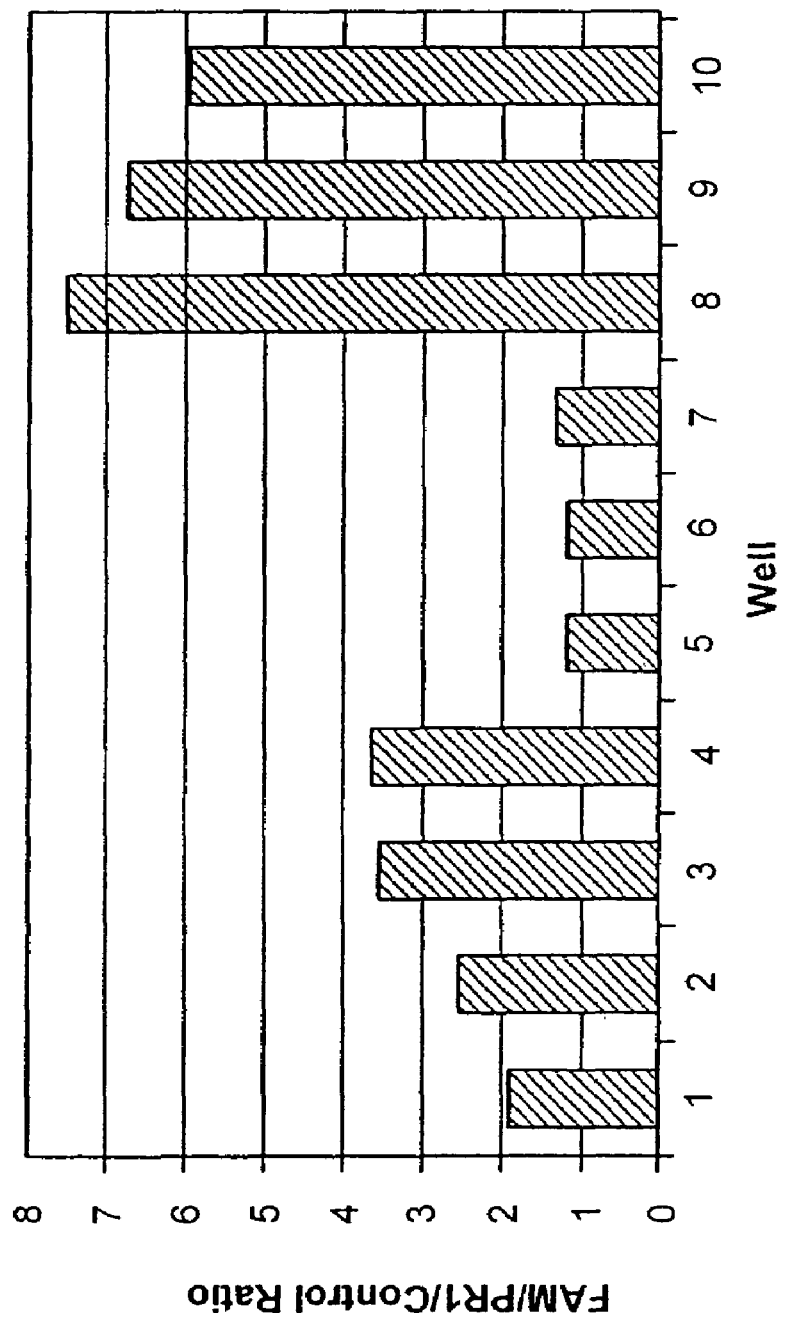
FIG. 12 is a bar graph that shows FAM/PRI/Control ratios for each of 10-1 nl wells branching from a single flow channel of a microfluidic device (see FIG. 7B). The amount of genomic DNA was 0.25 pg/nl, which results in an average of one target copy per well.

To further determine the sensitivity of TaqMan reactions in the microfluidic device, dilutions of genomic DNA were tested using the β-actin primer/probe set. Reaction compositions were generally composed as described in Example 1 using 4x DyNAzyme and dilutions of genomic DNA. The genomic DNA was diluted down to 0.25 µg/nl, which corresponds to approximately 1 copy per nl. The result of one dilution series is shown in FIG. 12.

According to a Poisson distribution, 37% of the total number of wells should be negative if the average target number is one. Well numbers 5, 6 and 7 are below the calculated threshold and, therefore, negative. This suggests that the β-actin TaqMan reactions in micro fluidic chip can detect an average of one copy per nl. Therefore, the sensitivity of the reactions in the microfluidic device is sufficient to perform genotyping experiments.

C. Genotyping Experiment

Figure 13:
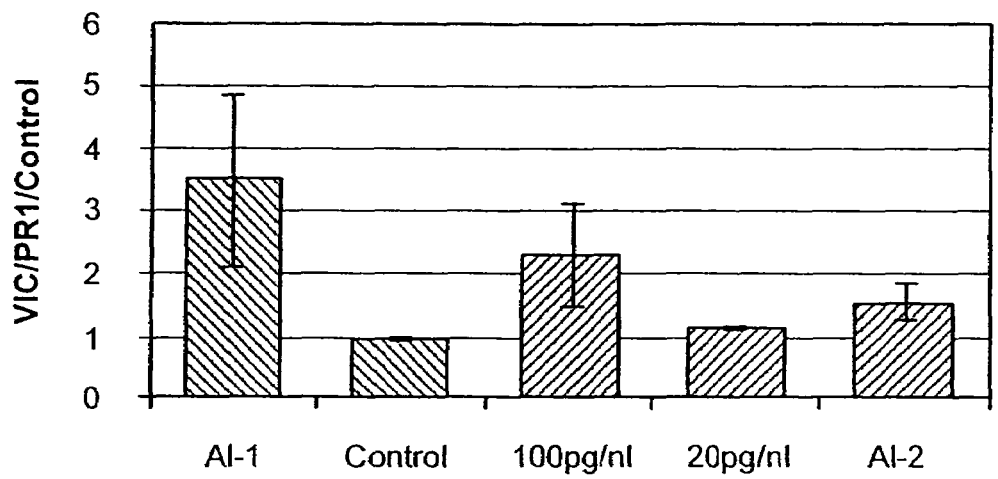
FIG. 13 is a bar graph depicting the average VIC/PRI/Control ratios for CYP2D6 SNP reactions using the microfluidic device shown in FIG. 7B. Allele 1 (Al-1) is the positive control for the VIC probe against the reference or wild type allele CYP2D6*1. Allele 2 (Al-2) is the positive control for the FAM probe against the variant or mutant allele, CYP2D6*3. The control has no DNA template. Genomic DNA was used at either 100 pg/nl or 20 pg/nl. The error bars are the standard deviation of the ratios.
Figure 14:
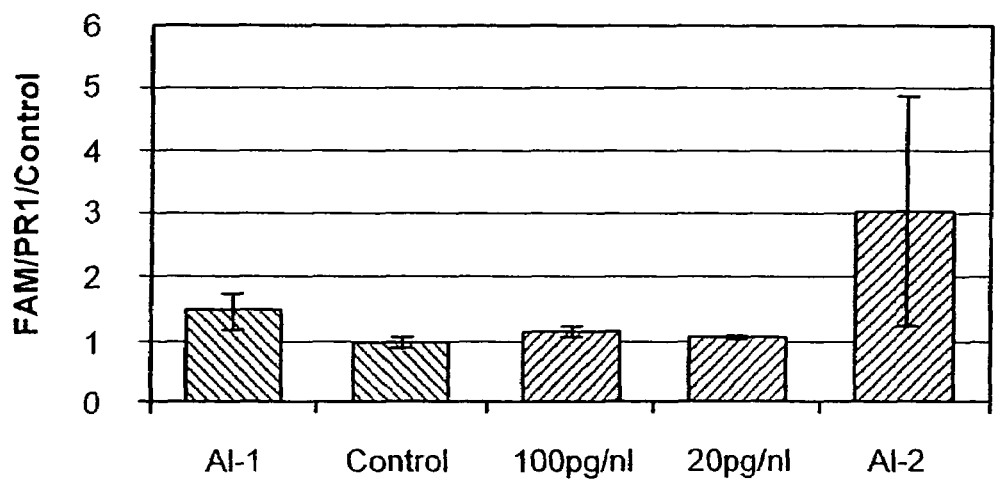
FIG. 14 is a bar graph showing the average FAM/PR1/Control ratios for CYP2D6 SNP reactions in the microfluidic device shown in FIG. 7B. The samples are the same as described with respect to FIG. 13 and in Example 3.

Because TaqMan in the microfluidic device is capable of detecting low target numbers, preliminary testing of SNP (Single Nucleotide Polymorphism) genotyping was performed using the Predetermined Allelic Discrimination kit (Applied Biosystems; Foster City, Calif.) against the CYP2D6 P450 cytochrome gene. The kit contains one primer set and two probes; FAM labeled for the wildtype or reference allele, CYP2D6*1, and VIC labeled for the CYP2D6*3 mutant or variant allele. Positive controls, PCR products, for each allele along with genomic DNA were tested in the device using the same conditions as described in Example 1. The results from one experiment are shown in FIGS. 13 and 14. The experiment has been repeated at least three times to validate the results and to demonstrate reliability.

As shown in FIG. 13, the Al-1 (Allele 1, CYP2D6*1 wild type allele) and genomic DNA (100 µg/nl) produced an average VIC/PR1/Control ratio of 3.5 and 2.2, respectively, indicating that the genomic DNA was positive for the CYP2D6*1, wild type allele. These values are above the threshold limit for the reactions. The signal strength of the TaqMan reactions in the microfluidic device is 59% and 40% of the Macro TaqMan controls, respectively. Al-2 (Allele 2, CYP2D6*3 mutant or variant allele), which should be negative in the VIC channel, showed some signal over control (1.5), possibly due to FAM fluorescence leaking into the VIC channel of the detector. The leakage can be minimized with an improved detection process.

The Al-2 positive control gave an average FAM/PRI/Control ratio of 3.0, which was 37% of the Macro TaqMan signal and above the calculated threshold limit (see FIG. 14). The genomic samples were negative for the CYP2D6*3 mutant allele, an expected result since the frequency of the CYP2D6*3 allele is low. Again, it appears that there is some leakage of the Al-1, VIC probe into the FAM channel of the detector. Overall, the SNP detection reactions were successful in the microfluidic device.

EXAMPLE 4

Verification of PCR by Gel Electrophoresis

I. Introduction

As an alternative method to prove amplification of DNA was occurring in the microfluidic device, an experiment to detect PCR product by gel electrophoresis was performed. PCR reactions compositions were as described in Example 1, except the TaqMan probe was omitted and the β-actin forward primer was conjugated to FAM.

II. Procedure

A. Microfluidic Device

Figure 15:
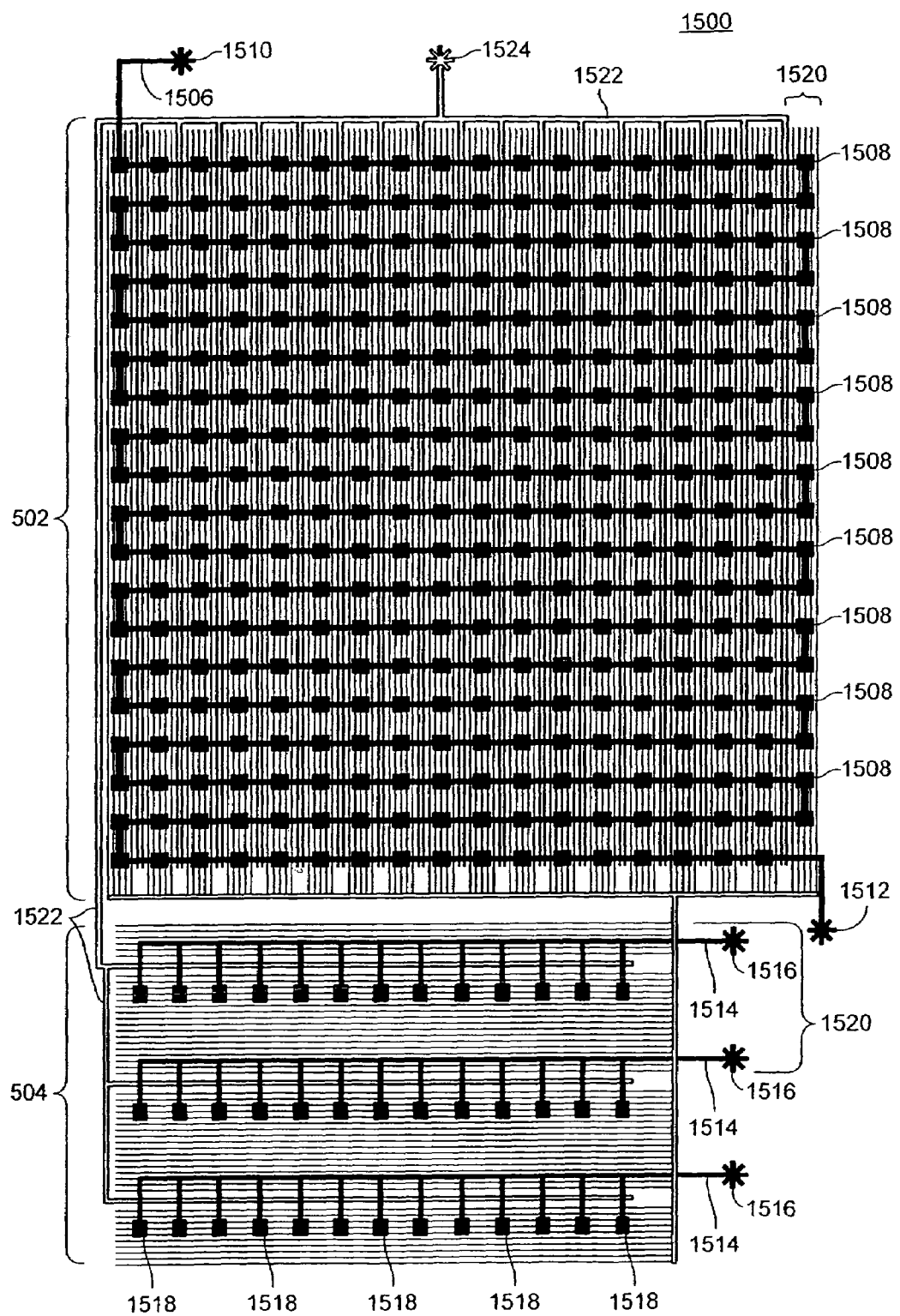
FIGS. 15 is a schematic diagram of the microfluidic device used for the experiments in Example 4.

A three layer microfluidic device, fabricated using the MSL process, was designed and fabricated for conducting the experiments described in this example; FIG. 15 shows a schematic view of the design. The device 1500 generally consists of a sample region 1502 and a control region 1504. Sample region 1502 contains three hundred and forty-one 1 nl reaction sites 1508 represented by the rectangles arrayed along flow channel 1506, which includes inlet via 1510 and outlet via 1512. Control region 1504 contains three control flow channels 1514 each containing ten 1 nl reaction sites 1518, also represented by the rectangles and an inlet via 1516. A network of control lines 1522 isolate each reaction site 1508, 1518 when sufficient pressure is applied to inlet via 1524. A series of guard channels 1520 are included to prevent liquid from evaporating out of the reaction sites 1508, 1518. The device is a three-layer device as described in Example 1 (see FIG. 7A). The entire chip is placed onto a coverslip.

B. Experimental Setup

Microfluidic device 1500 was loaded and thermocycled using the 3 temperature profile described in Example 1. The remaining reaction sample was thermocycled in the GeneAmp 9700 with the same thermocycling profile as for microfluidic device 1500. The reaction products were recovered after thermocycling was completed. To recover the amplified DNA, 3 µl of water was injected into sample input via 1506 and 3-4 µl of product were removed from outlet via 1512. The reaction products from device 1500 and the Macro reaction were treated with 2 µl of ExoSAP-IT (USB, Cleveland, Ohio), which is composed of DNA Exonuclease I and Shrimp Alkaline Phosphatase, to remove excess nucleotides and primers.

The Macro product was diluted from 1:10 to 1:106. The product from device 1500 was dehydrated and resuspended in 4 μl of formamide.

III. Results

Figure 16:
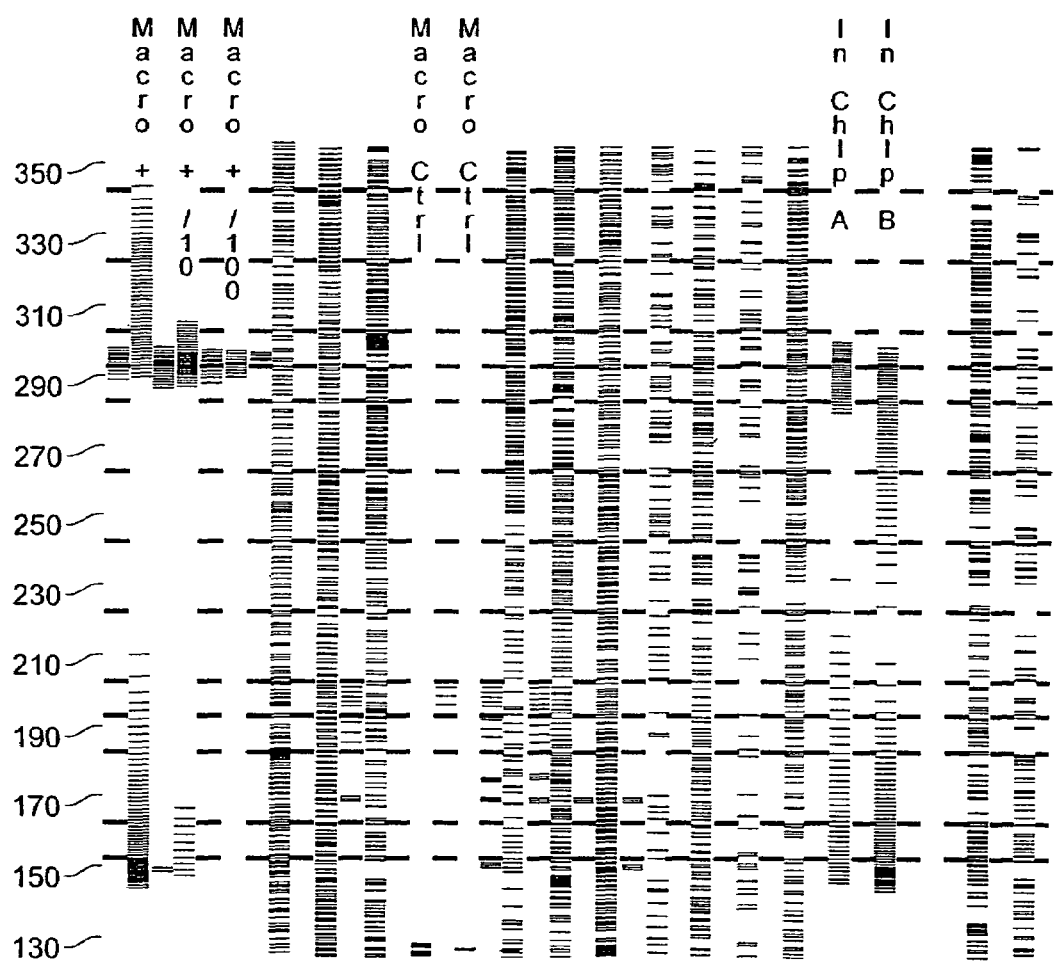
FIG. 16 is a polyacrylamide gel containing PCR product from Macro PCR and PCR reactions in the microfluidic device shown in FIG. 7B. The results on the left show the approximate migration of different DNA base pair lengths. The lanes containing interspersed bands are molecular weight markers. The lanes labeled "Macro" are the PCR products from the Macro reactions at different dilutions. The lanes labeled "In chip" are PCR products generated in the chip. The lanes containing many bands throughout the gel are nonspecific background signals.
Figure 17A:
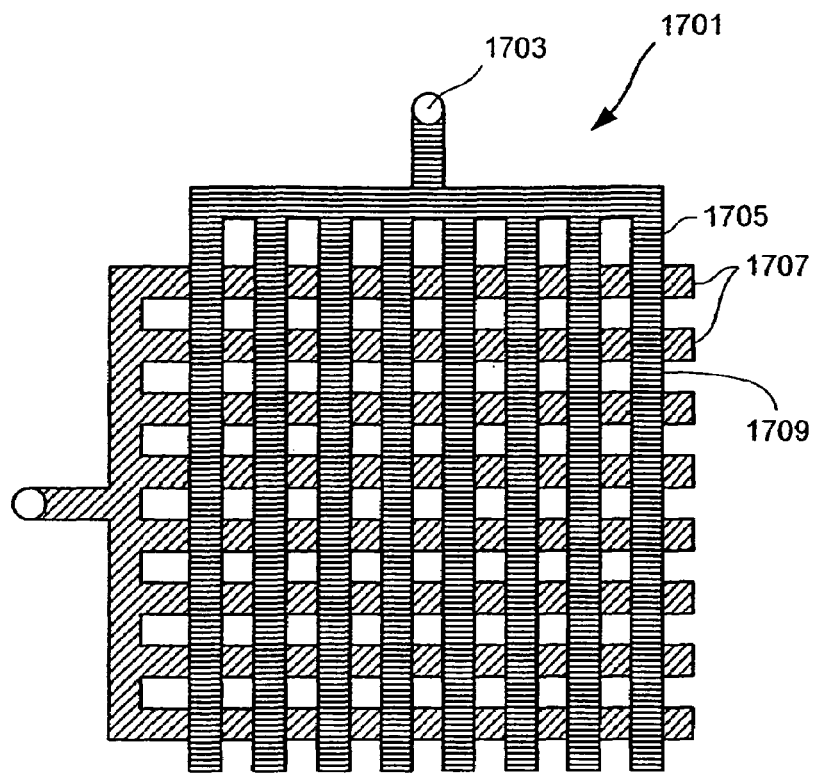
FIGS. 17a-17d depict two preferred designs of a partitioning microfluidic device in a valve off and valve actuated state.
Figure 17B:
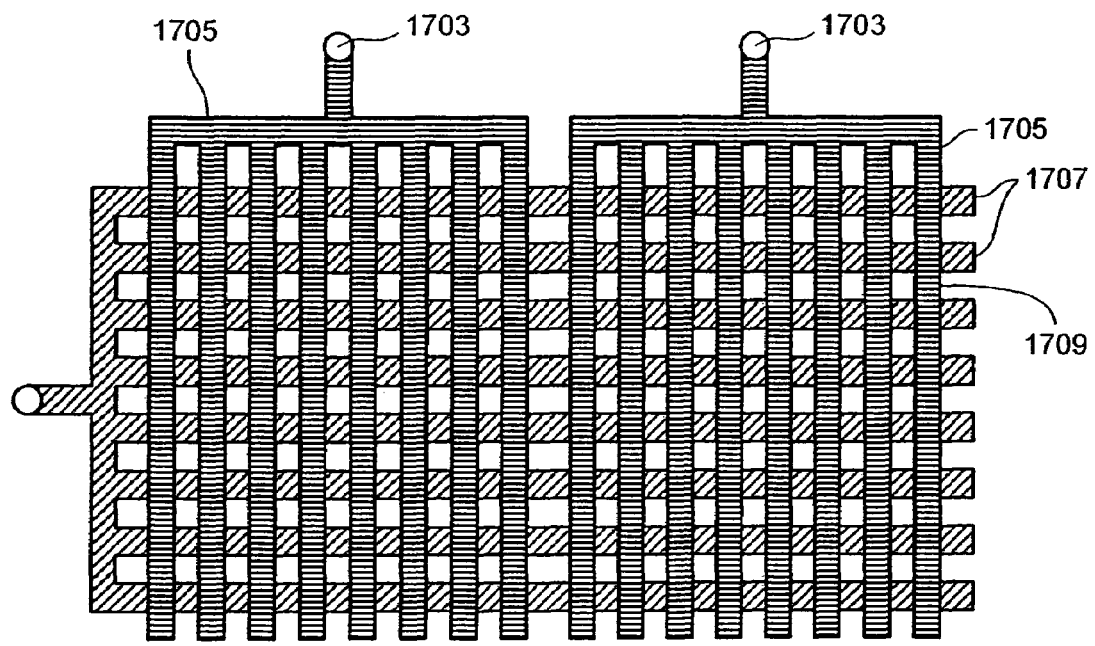
Figure 17C:
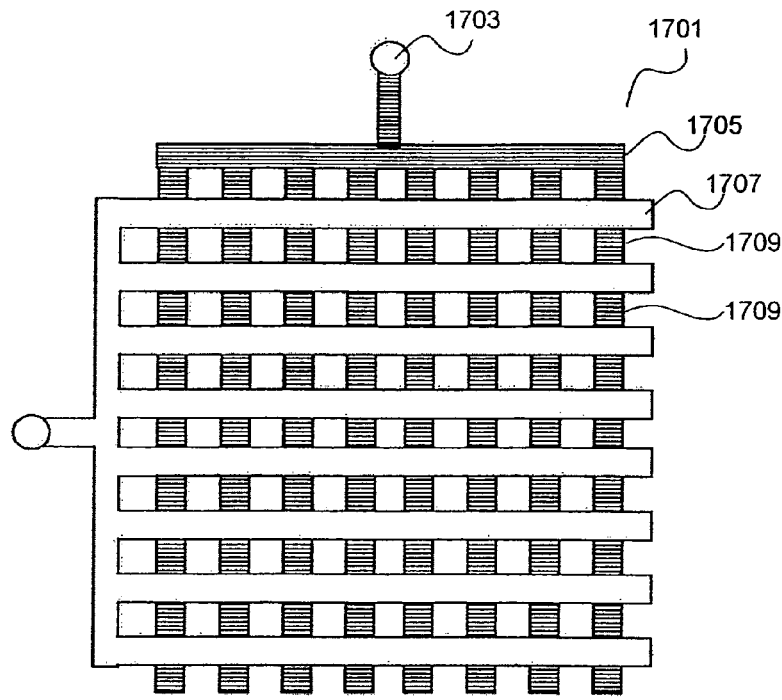
Figure 17D:
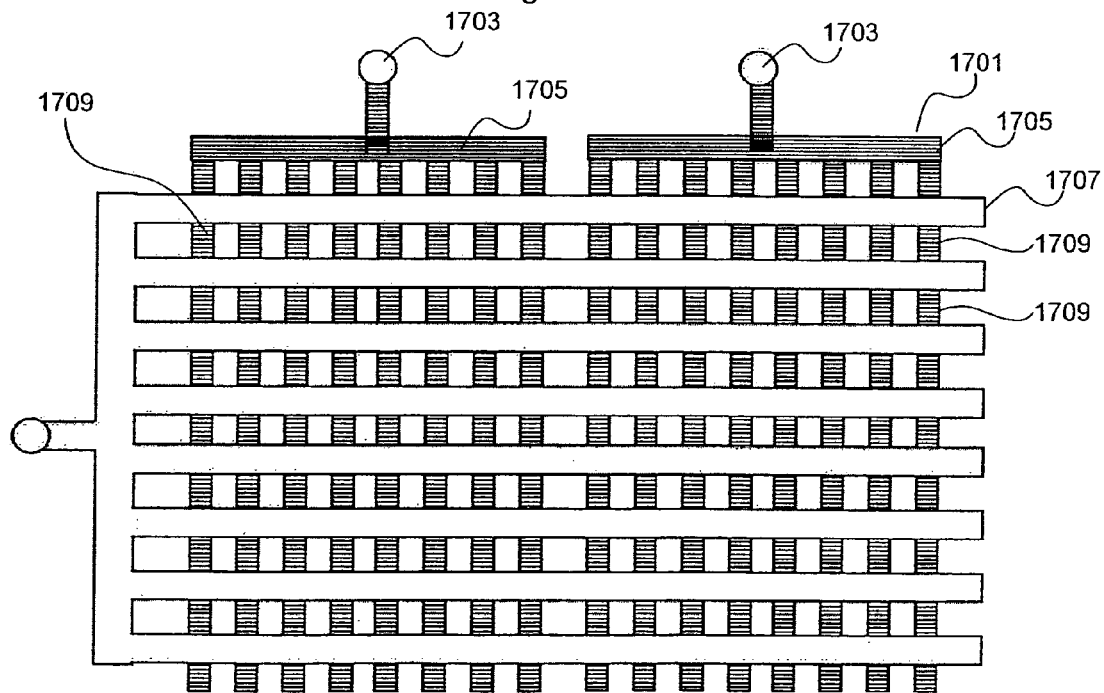

Both products, along with negative controls were analyzed, on a polyacrylamide gel. FIG. 15 shows the gel electrophoresis results. The appropriate size DNA band of 294 base pairs in length is observed in FIG. 16.

The products from the Macro reactions are shown on the left hand side of the gel and correspond to about 294 base pairs, the expected size of the β-actin PCR product. The negative controls lack the PCR product. Similarly, the product derived from the device gave the expected β-actin PCR product. Therefore, target DNA was amplified in the micro fluidic device.

EXAMPLE 5

Massive Partitioning

The polymerase chain reaction (PCR) has become an essential tool in molecular biology. Its combination of sensitivity (amplification of single molecules of DNA), specificity (distinguishing single base mismatches) and dynamic range ($10^5$ with realtime instrumentation) make it one of the most powerful analytical tools in existence. We demonstrate here that PCR performance improves as the reaction volume is reduced: we have performed 21,000 simultaneous PCR reactions in a single microfluidic chip, in a volume of 90 pL per reaction and with single template molecule sensitivity.

FIGS. 17a-17d depict a single bank and dual bank partitioning microfluidic device. where multilayer soft lithography (MSL) (Unger et al, *Science* 288, 113-116 (2000)),was used to create elastomeric microfluidic chips which use active valves to massively partition each of several liquid samples into a multitude of isolated reaction volumes. After injection of the samples into inlet 1703 which is in communication with branched partitioning channel system 1705 of microfluidic device 1701 (FIG. 17b), 2400 90 pL volumes 1709 of each sample are isolated by closing valves 1707 spaced along (FIG. 17d) simple microfluidic channels. The chip device is then thermocycled on a flat plate thermocycler and imaged in a commercially available fluorescence reader.

Figure 18A:
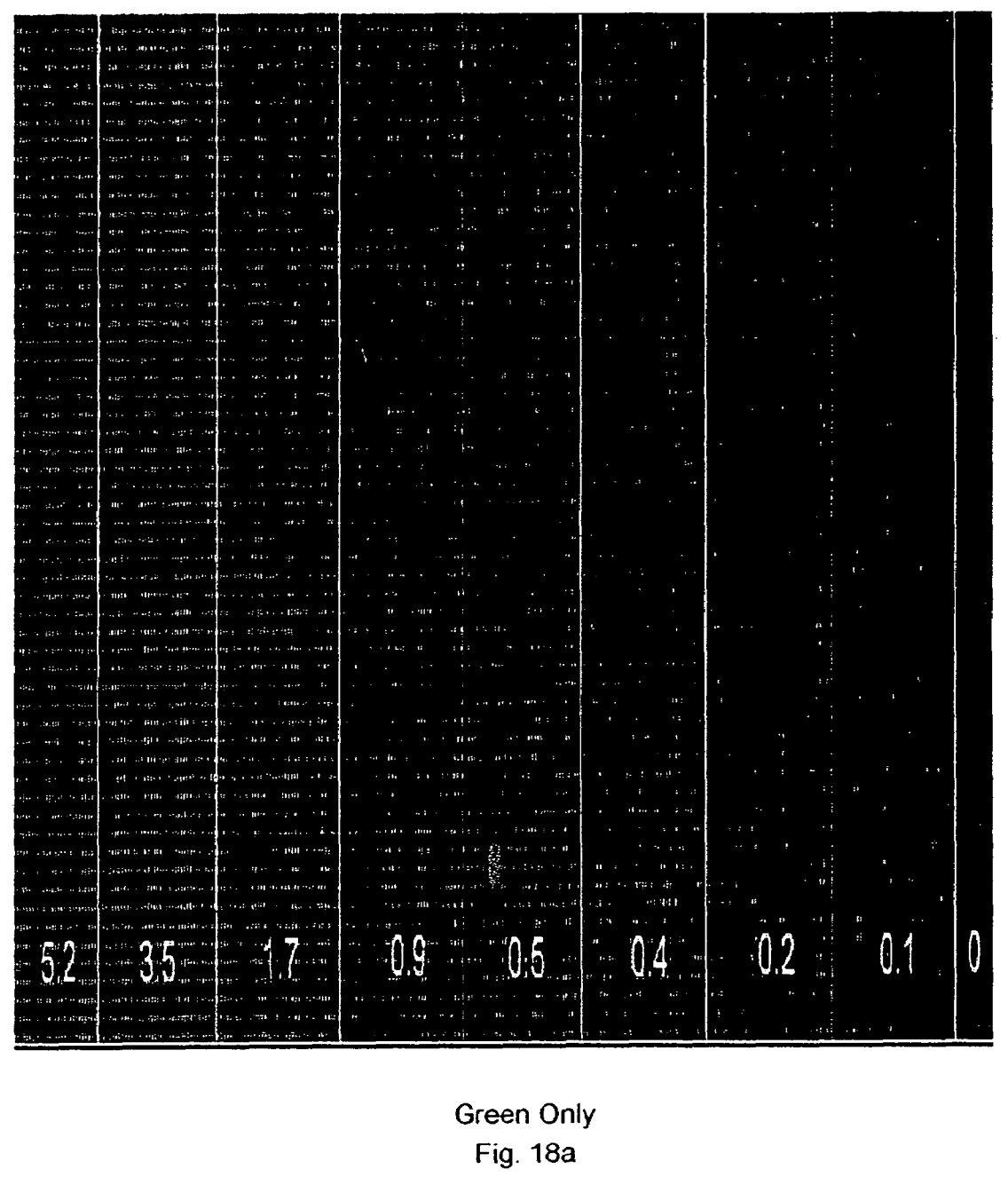
Figure 18B:
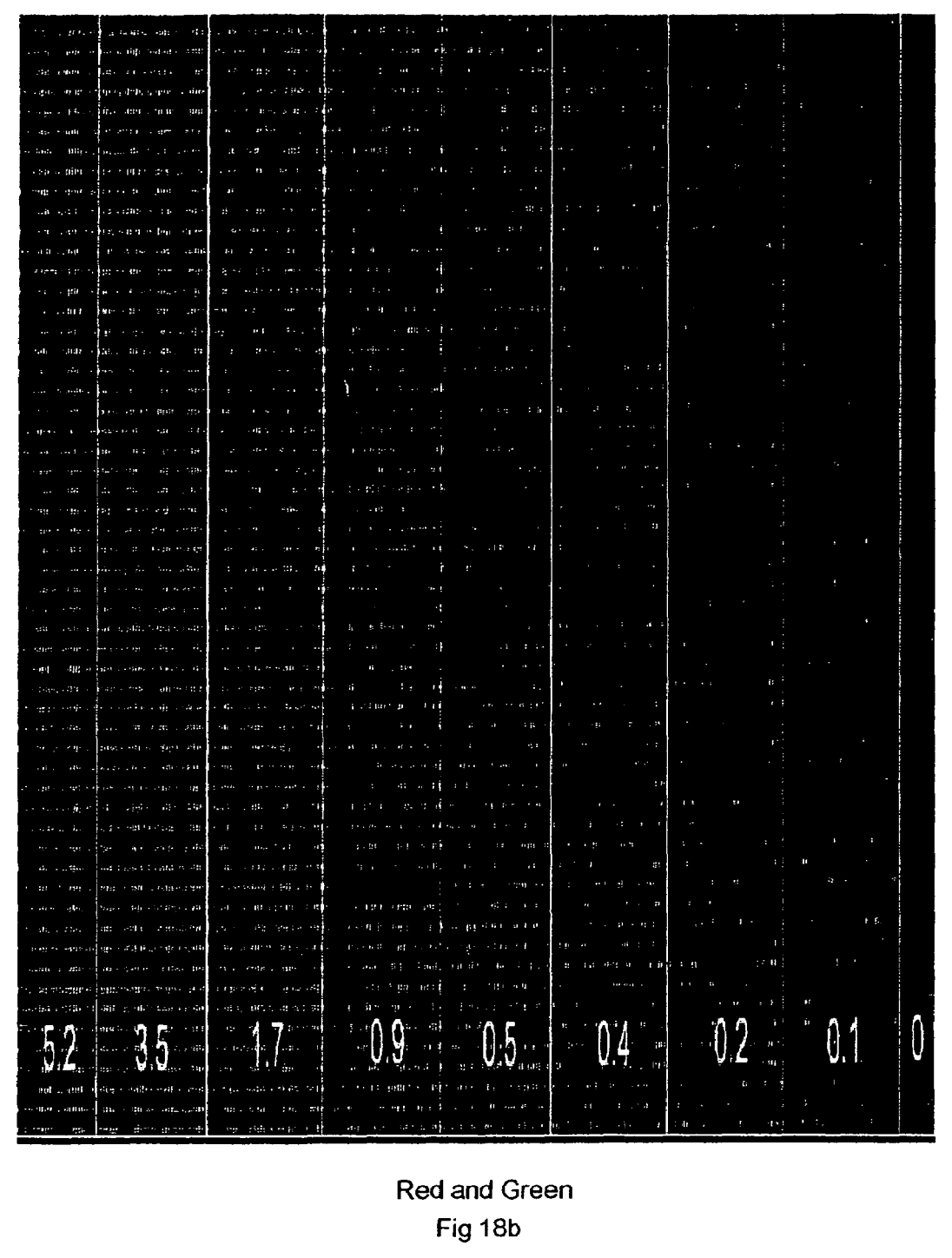
Figure 19:
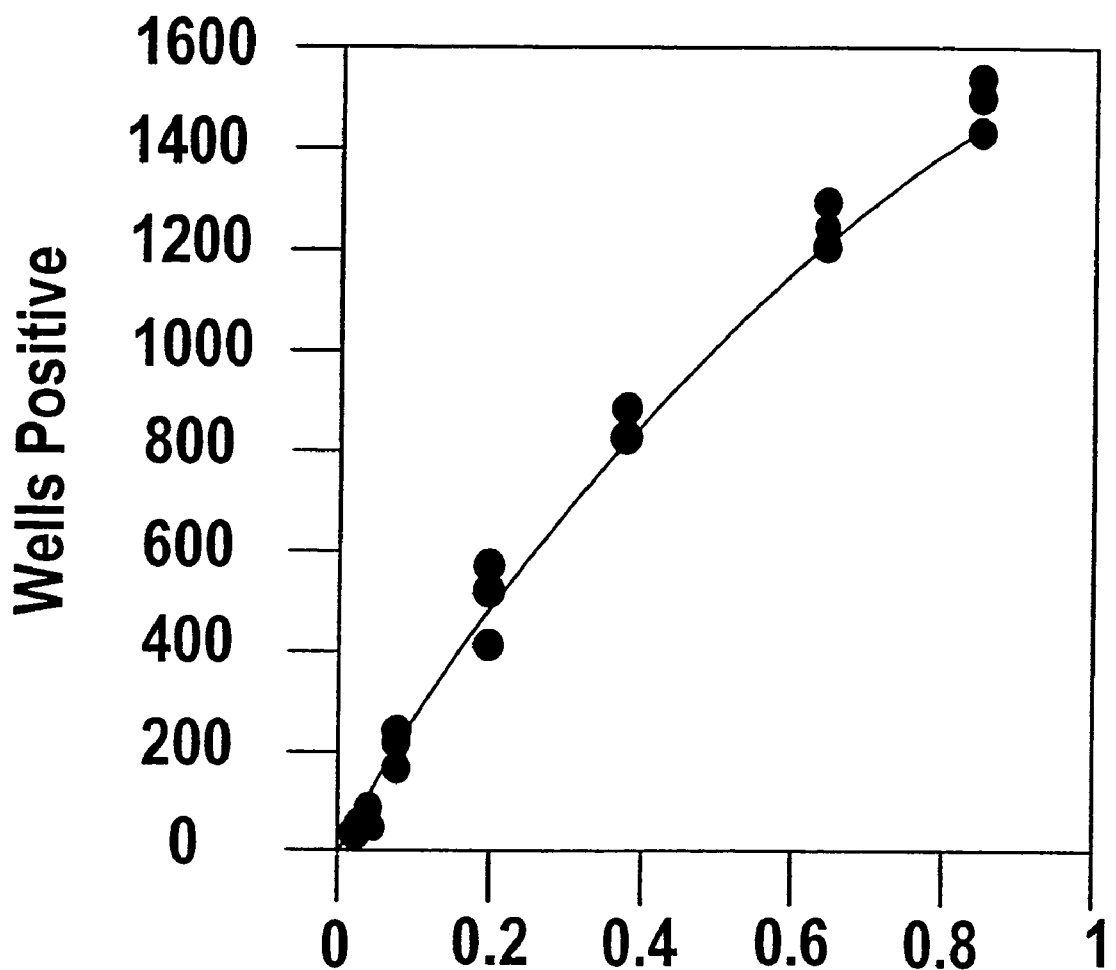
FIG. 19 depicts a graph of comparing the average number of copies per well to the number of positive wells.

We assessed the performance of PCR in the chips by varying the concentration of template DNA and measuring the number of wells that gave a positive Taqman™ signal. We found that a digital amplification is observed when the average number of copies per well is low (FIGS. 18a and 18b). A mixture of robust positive and clearly negative signals is observed even when the average number of copies per well is below 1; this implies that even a single copy of target can give good amplification. The number of positive wells was consistent with the number of wells calculated to have $\geq 1$ copy of target by the Poisson distribution (FIG. 19.). This result validates that this system gives amplification consistently even from a single copy of target. Fluorescent signal strengths from microfluidic Taqman™ PCR were comparable to macroscopic PCR reactions with the same DNA concentration—even though the macroscopic reactions contained >$10^4$ more template copies per reaction.

We believe that the primary source of this remarkable fidelity is the effective concentration of the target: a single molecule in a 90 μL volume is 55,000 times more concentrated than a single molecule in a 5 uL volume. Since the number of molecules of target, $n_t$, does not change (i.e. $n_t$=1) and the number of molecules that can produce side reactions, $n_s$, (i.e. primer-dimers and non-complementary DNA sequences in the sample) is linearly proportional to volume (i.e. $n_s$, $\propto$V), the ratio of target to side reactions is inversely proportional to volume: $n_t/n_s \propto 1/V$. Since side reactions are a primary cause of PCR failure (4), the advantage to reducing the volume of the reaction is clear.

PCR amplification from single copies of template has been previously reported (See E. T. Lagally, I. Medintz, R. A. Mathies, *Anal Chem* 73(3), 565-570 (2001), as well as B. Vogelstein, K. W. Kinzler, *PNAS* 96, 9236-9241 (1999)). However, current methods that achieve reliable amplification from single copies in a macroscopic volumes often require altered thermocycling protocols (e.g. long extension times, many cycles), precautions against mispriming and non-specific amplification (e.g. "hot start" PCR (thermal activation of the polymerase), "booster" PCR, additives to reduce nonspecific hybridization, etc), and are almost always done with two rounds of PCR, where an aliquot of the first PCR is used as template in the second reaction. In contrast, this system achieves reliable amplification from single copies using standard conditions—off-the-shelf primers and probes and a single-round, standard thermocycling protocol. Being completely enclosed, it is also nearly invulnerable to environmental contamination. The ability to do massive numbers of PCR reactions simultaneously provides definite logistical, cost and time advantages compared to macroscopic volumes (1 chip with 21,000 reactions vs. 219 separate 96 well plates, and the associated time, equipment, and tracking infrastructure).

This principle of massive partitioning with a digital PCR readout may be used for absolute quantification of the concentration of target in a sample. It can be used, for example, to genotype a pooled sample of genomic DNA simply by counting the numbers of wells that give a positive for a particular allele, or plurality of alleles as described above. Due to the enhanced resistance to side reactions, it should also be useful in quantifying mutants in a background of wild-type DNA—a problem relevant in cancer detection. The general principle of concentration by partitioning may also be useful in other reactions where detection of single molecules, bacteria, viruses or cells is of interest (e.g. ELISA reactions for protein detection). Digital PCR is described by Brown, et al., U.S. Pat. No. 6,143,496, titled "Method of sampling, amplifying and quantifying segment of nucleic acid, polymerase chain reaction assembly having nanoliter-sized chambers and methods of filling chambers", and by Vogelstein, et al, U.S. Pat. No. 6,446,706, titled "Digital PCR", both of which are hereby incorporated by reference in their entirety. The small volumes achievable using microfluidics allow both a massive degree of parallelization and very high target-to-background concentration ratios. High target-to-background ratios allow single-molecule amplification fidelity. These factors suggest that for PCR, smaller really is better.

The invention provides for methods and devices for conducting digital PCR in a microfluidic environment comprising the steps of: providing a microfluidic device having a fluid channel therein, said fluid channel having two or more valves associated therewith, the valves, when actuated, being capable of partitioning the fluid channel into two or more reaction sites or chambers; introducing a sample containing at least one target nucleic acid polymer, actuating the valves to partition the fluid sample into two or more portions, wherein at least one portion contains a target nucleic acid polymer and another portion does not contain a target nucleic acid polymer, amplifying the target nucleic acid polymer, and, determining the number of portions of the fluid channel that contained the target molecule. In preferred embodiments, the microfluidic device comprises an elastomeric material, and more preferably, comprises at least one layer comprising an elastomeric material. In certain preferred embodiments, the microfluidic device further comprises a deflectable membrane wherein the deflectable membrane is deflectable into and out of the fluid channel to control fluid flow within the fluid channel and/or to partition one portion of the fluid channel from another, preferably wherein the deflectable membrane is integral to a layer of the microfluidic device having a channel or recess formed therein, and preferably wherein the deflectable membrane is formed where a first channel in a first layer is overlapped by a second channel in a second layer of the microfluidic device. In some embodiments, the sample fluid contains all of the components needed for conducting an amplification reaction, while in other embodiments, the microfluidic device contains at least one component of an amplification reaction prior to the introduction of the sample fluid. In some embodiments, the microfluidic device further comprises a detection reagent, preferably one or more nucleic acid polymers complimentary to a least a portion of the target nucleic acid polymer, preferably a plurality of different nucleic acid polymers spatially arrayed within a reaction site or chamber of the microfluidic device.

Amplification may be achieved by thermocycling reactions such as PCR, or by isothermal reactions, such as described by Van Ness et al., in U.S. patent application Ser. No. 10/196,740 which has publishes as U.S. Ser. No. 2003/0138800 A1, which is herein incorporated by reference in its entirety for the purpose of teaching an isothermic amplification scheme.

The invention further provides for a protein microcalorimetry assay using a fluorescent dye, for example SYBER green (™), to measure the conformational changes of a protein, such as denaturation, especially if a protein's denaturation temperature changes when the protein interacts with another moiety such as a ligand or compound or other protein. An additional benefit of using SYBR Green (™) is that it us used at lower wavelengths than other UV range dyes thus reducing background problems typically associated with many plastic materials.

EXAMPLE 6

Detection of rare targets among high background genetic material samples

K-ras Experiment:

K-ras codon 12 mutant genomic DNA was obtained from MIA PaCa2 cell line was obtained from the Allan Balmain Laboratory at the University of California, San Francisco. The mutant genomic DNA was extracted using standard extraction protocols. For controls, one cell line, HELA (ATCC) was cultured and its DNA extracted per standard protocol, and a second control was obtained as purified human genomic DNA from PROMEGA™ corporation.

Reaction cocktails contained 50% of 2X master mix from a TAQMAN™ kit sold by ABI™corporation, a final concentration of 0.25% TWEEN™ 20 from SIGMA™ corporation, mutation specific primers at a concentration of 800 nM, wild-type non-extendible primer at 500 nM, a universal probe at 200 nM designed to function in accordance with the TAQMAN™ protocol specific for the present application, the balance being made up with DI water. The above-mentioned cocktail was divided into several different aliquots, to which each received an amount of target genomic DNA and/or "background" DNA. Specifically, the first reaction was a no-template control which received no DNA to establish a baseline signal. The second aliquot received 100 μg of mutant target DNA to serve as a positive control. The third aliquot received 100 μg of mutant DNA along with 500 ng of wild-type (from PROMEGA™) DNA. The forth aliquot received 100 μg of mutant DNA along with 1 μg of HELA (ATCC) wildtype DNA. The fifth aliquot received 100 μg of mutant DNA along 1 μg of wild type (PROMEGA™) DNA. The forth and fifth aliquots were to demonstrate the ability of the system to discern low concentrations of target among two different types of relatively high concentration "background" DNA. And, the sixth aliquot received 1 μg of wild type (PROMEGA™) DNA only as negative control.

A chip was made in accordance as described above in the present application, and, the chip used a silicon wafer as a substrate, and the elastomeric block comprised a third lower lever used to form channels from the recesses in the lower recess bearing layer of the elastomeric block, wherein the chip had twelve sample channels, each channel having 1,200 partitioning valves to create approximately 1,200 isolated chambers from each sample loaded into each sample channel through blind filling. Once each sample had been loaded into its respective sample channel, the sample channels were partitioned by applying a hydraulic force to the control channels that formed the partitioning valves along each sample channel. In this particular instance, the hydraulic fluid comprised water and PEG 3,350 mw average (from HAMPTON RESEARCH™ corporation) at a concentration of 25%w/v. The hydraulic fluidic was pressurized to a pressure of 35 PSI and held closed during the PCR reaction.

Amplification by PCR was performed in a real-time manner, as described in the TAQMAN™ kit using a modified EPPENDORF™ thermocycler that had a suction metallic block having a tortuous channel system thereon, the metallic block being disposed between the side of the silicon wafer opposite the elastomeric block and the thermal control surface of the thermocycler, wherein a vacuum source was applied to the tortuous channel system to urged the silicon wafer into near homogeneous thermal contact between the silicon wafer and the thermocycler thermal control surface as described in copending patent application Ser. No. 11/043,895, filed on Feb. 14, 2005, which is herein incorporated by reference in its entirety. As an alternative to using the vacuum chuck to hold down the chip and to establish thermal contact, a film of oil, such as mineral oil, may be used to achieve thermal conduction between the thermal control surface and the exposed silicon portion of the chip.

A thermocycling profile comprising 2 minute UNG clean up step at 52 degrees C., followed by a "hot start" at 95 degrees C. for ten minutes, followed by forty cycles of ramping between 25 seconds at 95 degrees C. to 40 seconds at 58 degrees C., operating the thermocycler at its fastest ramp rate between each temperature change.

Figure 22:
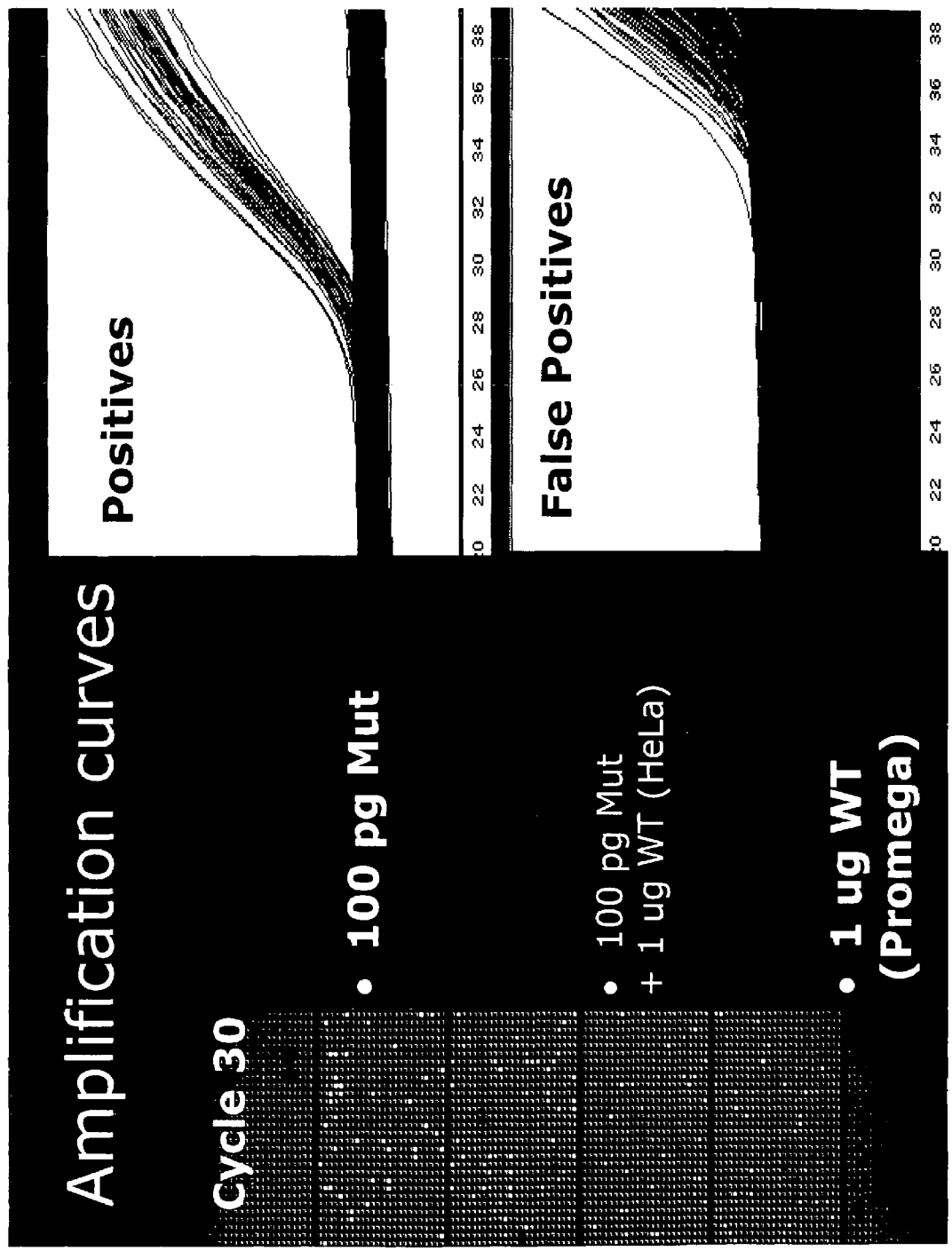
FIG. 22 depicts detection of rare targets among high background genetic material samples.

At the end of each 58 degree C. round, an two different images were taken of the chip using white light source that was filtered in accordance with the two different fluorophores used for the two color analysis. Ratio analysis was conducted between the two different color images to produce real-time amplification curves as shown in FIG. 22.

Figure 23:
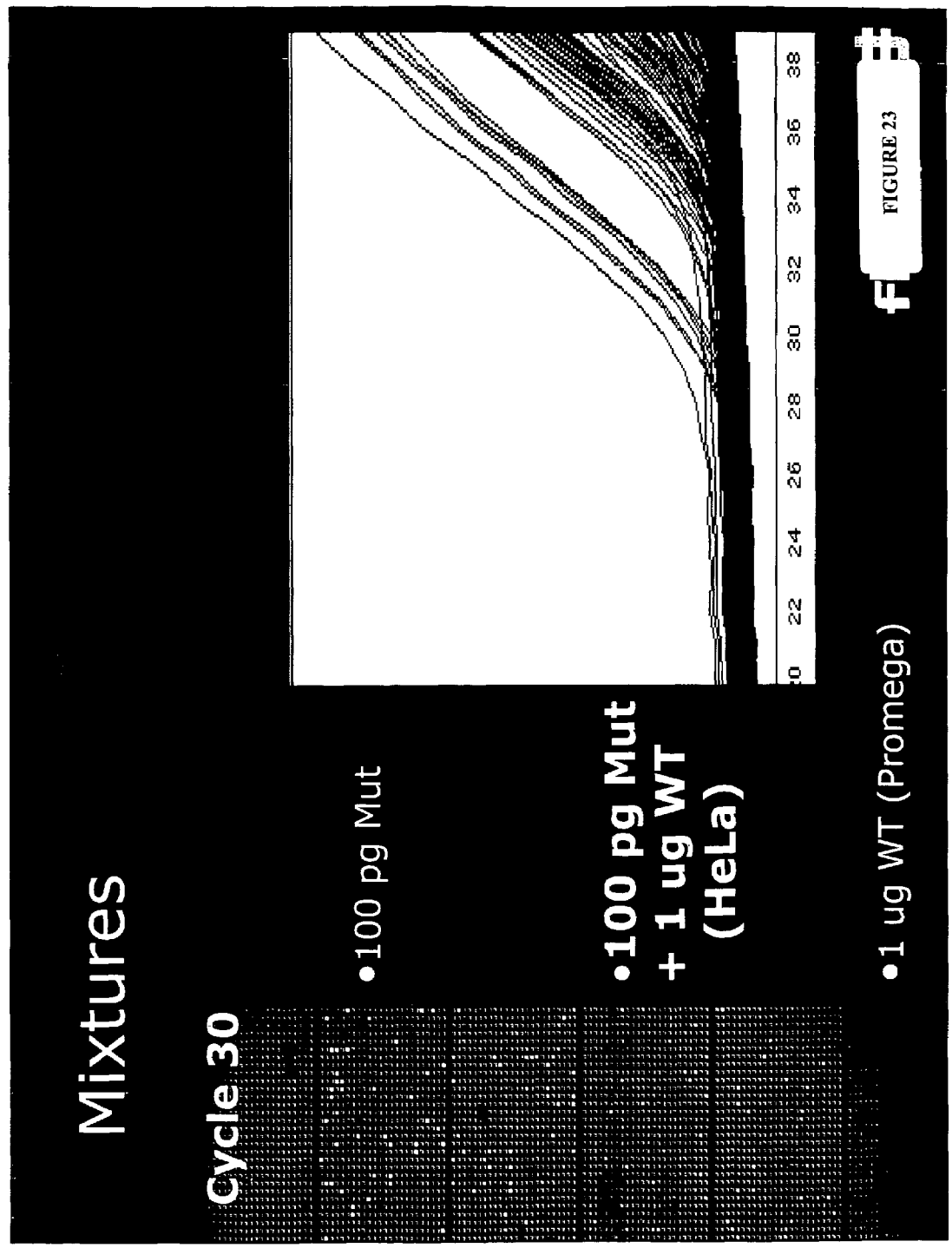
FIG. 23 detection of rare targets among high background genetic material samples.

Another experiment was performed using a chip similar to the above-mentioned chip, however, this chip one sample channel able to partition the sample channel into approximately 10,000 separate chambers. The sample comprises a cocktail as described above, and further including 100 μg of mutant DNA and 7 μg of wild type HELA DNA. The results of which are depicted in FIGS. 23 and 24. The number of cycles of amplification in this instance was only 30, of which the last cycle included an extension period of five minutes at 72 degrees C. Although the experiment was monitored in real-time as described above, it was appreciated that the assay could be performed as an end-point type assay.

REFERENCES:

1. Unger et al, *Science* 288, 113-116 (2000).
2. The sample channels and control lines are loaded by "blind filling" -PDMS is sufficiently gas permeable that liquid pressurized at a few psi drives the gas out of the channels, leaving them completely filled with liquid. See Hansen et al, *PNAS* 99, 16531-16536 (2002)
3. A 294 bp segment of the human β-actin gene was amplified using a 5'-exonuclease assay (Taqman). Forward and reverse primer sequences were 5'-TCACCCACACTGT-GCCCATCTACGA3' and 5'-CAGCGGAACCGCTCAT-TGCCAATGG3', respectively. FIG. 1b was taken with a TAMRA-based FRET probe, sequence 5'-(FAM)AT-GCCC-X(TAMRA) CCCCCATGCCATCCTGCGTp-3'. The data in FIG. 1c was taken with a dark-quencher based probe, as large numbers of these primer-probe sets are becoming commercially available. Reactions contained 1× Taqman buffer A (50 mM KCl, 10 mM Tris-HCl, 0.01 M EDTA, 60 nM Passive Reference 1, pH 8.3), 4 mM MgCl$_2$, 200 nM dATP, dCTP, dTTP, 400 nM dUTP, 300 nM forward primer, 300 nM reverse primer, 200 nM probe, 0.01 U/uL Amperase UNG (all from Applied Biosystems, Foster City, Calif.), 0.2 U/uL DyNAzyme (Finnzyme, Espoo, Finland), 0.5% Triton-x-100, 0.8 ug/ul Gelatin (Calbiochem, San Diego, Calif.), 5.0% Glycerol, deionized H$_2$O and human male genomic DNA (Promega).
4. *Quantitative PCR Technology*, Chapter on "Gene Quantification", L J McBride, K Livak, M Lucero, et al, Editor, Francois Ferre, Birkauser, Boston, MA p 97-110, 1998.
5. See E. T. Lagally, I. Medintz, R. A. Mathies, *Anal Chem* 73(3), 565-570 (2001), as well as B. Vogelstein, K. W. Kinzler, *PNAS* 96, 9236-9241 (1999)

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are incorporated by reference in their entirety for all purposes to the same extent as if each individual publication, patent or patent application were specifically and individually indicated to be so incorporated by reference.

What is claimed is:

1. A method for performing an analysis of a sample comprising the steps of:
   a) providing a microfluidic device comprising:
   a sample channel having cross-sectional dimensions between 0.1 and 1000 μm,
   valves positioned such that the sample channel is partitioned into a plurality of fluidically isolated chambers by activation of said valves, said valves being formed in said microfluidic device by one or more deflectable membrane(s) that can be deflected into said sample channel,
   wherein said deflectable membrane is formed from an elastomeric material having a Young's modulus in the range 20 Pa to 1 GPa,
   wherein said fluidically isolated chambers are not located at junctions formed by the sample channel and other flow channels that are in fluid communication with the sample channel, and
   wherein said sample channel has an entrance for introduction of a fluid, but does not have a separate exit
   b) introducing a sample fluid comprising reagents for nucleic acid amplification and at least one amplifiable target into said sample channel,
   c) simultaneously actuating said valves to produce at least 500 fluidically isolated chambers, wherein at least one amplifiable target is present in at least one chamber,
   d) conducting amplification steps simultaneously in said at least 500 fluidically isolated chambers wherein an amplified target is produced in at least one chamber, and
   e) detecting said amplified target.

2. The method of claim 1, wherein said amplification steps are polymerase chain reaction (PCR) steps which result in a PCR product being formed.

3. The method of claim 2, wherein said PCR is digital PCR.

4. The method of claim 3, wherein said polymerase chain reaction produces two different color results.

5. The method of claim 1 wherein the sample channel is a branched partitioning channel system and said sample is introduced into said branched partitioning system and a plurality of valves are actuated to isolate said sample into a plurality of isolated reaction volumes.

6. The method of claim 1 wherein the analysis is single nucleotide polymorphism analysis.

7. The method of claim 1 wherein the analysis is genotyping.

8. The method of claim 1 wherein the analysis is real time PCR.

9. The method of claim 1 wherein the fluid capacity of each chamber is less than 20 nL.

10. The method of claim 9 wherein the fluid capacity of each chamber is less than 10 nL.

11. The method of claim 1 wherein sample channel is formed in an elastomeric substrate.

12. The method of claim 1 wherein the and step (c) comprises simultaneously actuating said valves to isolate at least 1000 separate chambers.

13. The method of claim 12 wherein step (c) comprises simultaneously actuating said valves to isolate at least 2000 separate chambers.

14. The method of claim 13 wherein step (c) comprises simultaneously actuating said valves to isolate at least 3000 separate chambers.

15. The method of claim 14 wherein step (c) comprises simultaneously actuating said valves to isolate at least 5000 separate chambers.

16. The method of claim 15 wherein step (c) comprises simultaneously actuating said valves to isolate at least 10,000 separate chambers.

17. The method of claim 1 wherein deflectable membrane is formed from an elastomeric material having a Young's modulus in the range 50 Pa to 10 MPa.

18. The method of claim 17 wherein deflectable membrane is formed from an elastomeric material having a Young's modulus in the range 100 Pa to 1 MPa.

19. The method of claim 1 wherein the deflectable membrane is formed from polydimethylsiloxane (PDMS).

20. The method of claim 1 wherein the sample fluid comprises at least one blocking reagent selected from the group consisting of a protein and a detergent.

21. The method of claim 1 wherein the amplification steps comprise isothermal amplification.

* * * * *